US008906916B2

(12) United States Patent
Heinrich et al.

(10) Patent No.: US 8,906,916 B2
(45) Date of Patent: Dec. 9, 2014

(54) PYRIMIDINE DERIVATIVES AS FAK INHIBITORS

(75) Inventors: Timo Heinrich, Gross-Umstadt (DE); Christina Esdar, Mainz (DE); Hartmut Greiner, Weiterstadt (DE)

(73) Assignee: Merck Patent GmbH, Darmstadt (DE)

( * ) Notice: Subject to any disclaimer, the term of this patent is extended or adjusted under 35 U.S.C. 154(b) by 16 days.

(21) Appl. No.: 13/817,251

(22) PCT Filed: Jul. 19, 2011

(86) PCT No.: PCT/EP2011/003597
§ 371 (c)(1),
(2), (4) Date: Feb. 15, 2013

(87) PCT Pub. No.: WO2012/022408
PCT Pub. Date: Feb. 23, 2012

(65) Prior Publication Data

US 2013/0158005 A1 Jun. 20, 2013

(30) Foreign Application Priority Data

Aug. 18, 2010 (DE) ........................ 10 2010 034 699

(51) Int. Cl.

| | |
|---|---|
| *C07D 233/88* | (2006.01) |
| *A61K 31/505* | (2006.01) |
| *C07D 401/14* | (2006.01) |
| *C07D 417/12* | (2006.01) |
| *C07D 401/12* | (2006.01) |
| *C07D 405/04* | (2006.01) |
| *C07D 413/14* | (2006.01) |
| *C07D 413/12* | (2006.01) |
| *C07D 239/42* | (2006.01) |
| *C07D 403/12* | (2006.01) |
| *C07D 401/06* | (2006.01) |
| *C07D 403/04* | (2006.01) |
| *C07D 403/14* | (2006.01) |
| *C07D 401/04* | (2006.01) |
| *C07D 417/04* | (2006.01) |

(52) U.S. Cl.
CPC ............ *C07D 239/42* (2013.01); *C07D 401/14* (2013.01); *C07D 417/12* (2013.01); *C07D 401/12* (2013.01); *C07D 405/04* (2013.01); *C07D 413/14* (2013.01); *C07D 413/12* (2013.01); *C07D 403/12* (2013.01); *C07D 233/88* (2013.01); *C07D 401/06* (2013.01); *C07D 403/04* (2013.01); *C07D 403/14* (2013.01); *C07D 401/04* (2013.01); *C07D 417/04* (2013.01)
USPC .................. 514/235.8; 514/252.02; 514/275; 544/122; 544/238; 544/330; 544/331

(58) Field of Classification Search
USPC ............... 544/122, 238, 330, 331; 514/235.8, 514/252.02, 275
See application file for complete search history.

(56) References Cited

U.S. PATENT DOCUMENTS

| | | | | |
|---|---|---|---|---|
| 7,109,335 | B2 | 9/2006 | Kath et al. | |
| 7,351,712 | B2 | 4/2008 | Kath et al. | |
| 7,674,796 | B2 | 3/2010 | Kath et al. | |
| 7,741,336 | B2 | 6/2010 | Kath et al. | |
| 2003/0171359 | A1* | 9/2003 | Dahmann et al. | 514/217.06 |
| 2005/0009853 | A1 | 1/2005 | Kath et al. | |
| 2006/0281774 | A1 | 12/2006 | Kath et al. | |
| 2008/0182840 | A1 | 7/2008 | Kath et al. | |
| 2008/0300234 | A1 | 12/2008 | Kath et al. | |
| 2009/0258888 | A1 | 10/2009 | Nagarathnam et al. | |
| 2013/0324532 | A1* | 12/2013 | Holmes et al. | 514/235.8 |
| 2013/0324546 | A1* | 12/2013 | Holmes et al. | 514/252.14 |

FOREIGN PATENT DOCUMENTS

| | | | |
|---|---|---|---|
| WO | 03/087087 | A2 | 10/2003 |
| WO | 2004/056807 | A1 | 7/2004 |
| WO | 2006/110763 | A1 | 10/2006 |

OTHER PUBLICATIONS

Simone, Oncology: Introduction, Cecil Textbook of Medicine, 20th Edition, vol. 1, pp. 1004-1010, 1996.*

Gura, Systems for identifying New Drugs Are Often Faulty, Cancer Models, Science, vol. 278, No. 5340, pp. 1041-1042, Nov. 1997.*

Johnson et al., Relationships between drug activity in NCI preclinical in vitro and in vivo models and early clinical trials, British Journal of Cancer (2001) 64(10): 1424-1431.*

Pearce et al., Failure modes in anticancer drug discovery and development, Cancer Drug Design and Discovery Edited by Stephen Neidle, Chapter 18, pp. 424-435 (2008).*

Layzer, Degenerative Diseases of the Nervous System, Cecil Textbook of Medicine, 20th Edition, vol. 2, pp. 2050-2057 (1996).*

Damasio, Alzheimer's Disease and Related Dementias, Cecil Textbook of Medicine, 20th Edition, vol. 2, pp. 1992-1996 (1996).*

Traxler, Protein Tyrosine Kinase inhibitors in cancer treatment, Expert Opinion on Therapeutic Patents, 7(6): 571-588, 1997.*

International Search Report for PCT/EP2011/003597 (Sep. 15, 2011).

International Preliminary Report on Patentability for PCT/EP2011/003597 (Feb. 19, 2013).

B. Blank et al., "Catalytic Alkylation of Methyl-N-Heteroaromatics with Alcohols", Journal of the American Chemical Society, vol. 132, No. 3 (Jan. 27, 2010) pp. 924-925.

T. Matsukawa et al., "Reactions of 2-Aminopyrimidines with Aromatic Aldehydes. I", Journal of the Pharmaceutical Society of Japan, vol. 72, No. 7 (Jan. 1, 1952) pp. 909-912.

A. Schultze et al., "Therapeutic Potential and Limitations of New FAK Inhibitors in the Treatment of Cancer", Expert Opinion on Investigational Drugs, vol. 19, No. 6 (Jun. 1, 2010) pp. 777-788.

* cited by examiner

*Primary Examiner* — Deepak Rao
(74) *Attorney, Agent, or Firm* — Millen, White, Zelano & Branigan, P.C.

(57) ABSTRACT

Compounds of the formula (I), in which $R^1$, $R^2$ and $R^3$ have the meanings indicated in Claim 1, are kinase inhibitors and can be employed, inter alia, for the treatment of tumors.

3 Claims, No Drawings

PYRIMIDINE DERIVATIVES AS FAK INHIBITORS

BACKGROUND OF THE INVENTION

The invention had the object of finding novel compounds having valuable properties, in particular those which can be used for the preparation of medicaments.

The present invention relates to compounds in which the inhibition, regulation and/or modulation of signal transduction by kinases, in particular tyrosine kinases, plays a role, furthermore to pharmaceutical compositions which comprise these compounds, and to the use of the compounds for the treatment of tyrosine kinase-induced diseases.

Specifically, the present invention relates to compounds which inhibit, regulate and/or modulate tyrosine kinase signal transduction, to compositions which comprise these compounds, and to methods for the use thereof for the treatment of tyrosine kinase-induced diseases and conditions, such as cancer, tumour growth, arteriosclerosis, age-related macular degeneration, diabetic retinopathy, inflammatory diseases and the like, in mammals.

Tyrosine kinases are a class of enzymes which catalyse the transfer of the terminal phosphate of adenosine triphosphate to tyrosine residues in protein substrates. It is thought that tyrosine kinases, through substrate phosphorylation, play a crucial role in signal transduction for a number of cellular functions. Although the precise mechanisms of signal transduction are still unclear, tyrosine kinases have been shown to be important contributing factors in cell proliferation, carcinogenesis and cell differentiation. Tyrosine kinases can be categorised as receptor-type tyrosine kinases or non-receptor-type tyrosine kinases. Receptor-type tyrosine kinases have an extracellular portion, a transmembrane portion and an intracellular portion, while non-receptor-type tyrosine kinases are exclusively intracellular. Non-receptor-type tyrosine kinases consist of a multiplicity of subfamilies, including Src, Frk, Btk, Csk, Abl, Zap70, Fes/Fps, Fak, Jak, Ack and LIMK. Each of these subfamilies is further sub-divided into different receptors. For a more detailed discussion of non-receptor-type tyrosine kinases, see thepaper by Bolen *Oncogene,* 8:2025-2031 (1993), which is hereby incorporated by way of reference.

Both receptor-type tyrosine kinases and non-receptor-type tyrosine kinases are involved in cellular signalling pathways leading to numerous pathogenic conditions, including cancer, psoriasis and hyperimmune responses.

The present invention relates to the compounds as inhibitors of FAK (focal adhesion kinase).

FAK (encoded by the PTK2 gene) is a non-receptor tyrosine kinase which integrates signals from integrins and growth factor receptors. FAK has been reported to play a role in the regulation of cell survival, growth, spread, migration and invasion (McLean et al 2005, Nat Rev Cancer 5:505-515). Furthermore, FAK is regulated and activated by phosphorylation on multiple tyrosine residues. Overexpression of FAK mRNA and/or protein has been documented in many human tumours, including cancers of the breast, colon, thyroid, and prostate (Owens et al. 1995, Cancer Research 55: 2752-2755; Agochiya et al. 1999, Oncogene 18: 5646-5653; Gabarro-Niecko et al. 2003, Cancer Metastasis Rev. 22:359-374). More importantly, there is evidence that phosphorylated FAK is increased in malignant tissues compared with normal tissues (Grisaru-Granovsky et al. 2005, Int. J. Cancer 113: 372-378).

Inhibition of FAK by RNAi or expression of a dominant-negative FAK has been shown to induce loss of adhesion and cell death in human breast and melanoma cell lines and to increase docetaxel-mediated apoptosis in ovarian cancer cells (Beviglia et al 2003, Biochem J. 373:201-210, Smith et al 2005, Melanoma Res. 15:357-362, Haider et al 2005, Clin. Cancer Res. 11:8829-8836). However, inhibition of FAK in normal human fibroblasts or immortalized mammalian cells (MCFIOA) was found not to cause loss of attachment or apoptosis (Xu et al. 1996 Cell Growth and Diff 7:413-418). Inhibition of FAK by dominant-negative expression has also been shown to reduce tumour growth and eliminate lung metastasis of mammalian adenocarcinoma cells in a syngenetic rat model (van Nimwegen et al 2005, Cancer Res. 65:4698-4706). Likewise, inhibition of FAK by shRNA inhibited lung metastasis and reduced lethality by 40% in a syngenetic mouse model (Mitra et al 2006, Oncogene 25: 4429-4440). In this study, transient re-expression of wild-type, but not kinase-inactive FAK resulted in re-mutation of the shRNA phenotypes. Inhibition of FAK by dominant-negative expression in mouse 4TI carcinoma cells reduced tumour growth and angiogenesis in mice (Mitra et al 2006, Oncogene 25:5969-5984).

In addition, loss of FAK catalytic activity (reconstitution of FAK−/− cells with kinase-inactive FAK) reduced growth of v-Src tumours in mice and decreased angiogenesis.

Thus, there is strong evidence to suggest that inhibition of FAK activity induces apoptosis, loss of adhesion, inhibition of cell growth and migration and that such inhibition reduces angiogenesis. Accordingly, compounds which inhibit FAK activity would be useful for the treatment of cancer.

The identification of small compounds which specifically inhibit, regulate and/or modulate FAK signal transduction is therefore desirable and an aim of the present invention.

It has been found that the compounds of the formula I and salts thereof have very valuable pharmacological properties while being well tolerated. In particular, they exhibit FAK inhibiting properties.

The present invention furthermore relates to the use of one or more compounds according to the invention in the treatment and/or prophylaxis of diseases, preferably the diseases described herein, that are caused, mediated and/or propagated by Raf kinases and in particular diseases that are caused, mediated and/or propagated by FAK.

The diseases discussed herein are usually divided into two groups, hyperproliferative and non-hyperproliferative diseases. In this connection, psoriasis, arthritis, inflammation, endometriosis, scarring, benign prostatic hyperplasia, immunological diseases, autoimmune diseases and immunodeficiency diseases are to be regarded as non-cancerous diseases, of which arthritis, inflammation, immunological diseases, autoimmune diseases and immunodeficiency diseases are usually regarded as non-hyperproliferative diseases. In this connection, brain cancer, lung cancer, squamous cell cancer, bladder cancer, gastric cancer, pancreatic cancer, hepatic cancer, renal cancer, colorectal cancer, breast cancer, head cancer, neck cancer, oesophageal cancer, gynaecological cancer, thyroid cancer, lymphoma, chronic leukaemia and acute leukaemia are to be regarded as cancerous diseases, all of which are usually regarded as hyperproliferative diseases. In particular, cancerous cell growth is a disease which is a target of the present invention. The present invention therefore relates to compounds according to the invention as medicaments and/or medicament active compounds in the treatment and/or prophylaxis of the said diseases and to the use of compounds according to the invention for the preparation of a pharmaceutical for the treatment and/or prophylaxis of the said diseases as well as to a method for the treatment of the said diseases which comprises the administration of one or more compounds according to the invention to a patient in need of such an administration.

It can be shown that the compounds according to the invention have an antiproliferative action in vivo. The compounds according to the invention are administered to a patient having a hyperproliferative disease, for example to inhibit tumour growth, to reduce inflammation associated with a lymphoproliferative disease, to inhibit transplant rejection or neurological damage due to tissue repair, etc. The present compounds are suitable for prophylactic or therapeutic purposes. As used herein, the term “treatment” is used to refer to both prevention of diseases and treatment of pre-existing conditions. The prevention of proliferation is achieved by administration of the compounds according to the invention prior to the development of overt disease, for example to prevent the growth of tumours, prevent metastatic growth, diminish restenosis associated with cardiovascular surgery, etc. Alternatively, the compounds are used for the treatment of ongoing diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow the active agents to induce cell death or to inhibit migration, usually between about one hour and one week. In vitro testing can be carried out using cultivated cells from a biopsy sample. The viable cells remaining after the treatment are then counted.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

For the identification of kinase inhibitors, various assay systems are available. In scintillation proximity assay (Sorg et al., J. of. Biomolecular Screening, 2002, 7, 11-19) and flashplate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. of Biomolecular Screening, 2002, 191-214).

Other non-radioactive ELISA assay methods use specific phospho-anti-bodies (phospho-ABs). The phospho-AB binds only the phosphorylated substrate. This binding can be detected by chemiluminescence using a second peroxidase-conjugated anti-sheep antibody (Ross et al., 2002, Biochem. J., just about to be published, manuscript BJ20020786).

There are many diseases associated with deregulation of cellular proliferation and cell death (apoptosis). The conditions of interest include, but are not limited to, the following. The compounds according to the invention are suitable for the treatment of a number of conditions where there is proliferation and/or migration of smooth muscle cells and/or inflammatory cells into the intimal layer of a vessel, resulting in restricted blood flow through that vessel, for example in the case of neointimal occlusive lesions. Occlusive vascular diseases of interest include atherosclerosis, graft coronary vascular disease after transplantation, vein graft stenosis, peri-anastomatic prosthetic restenosis, restenosis after angioplasty or stent placement, and the like.

PRIOR ART

Pyridine derivatives are described as FAK inhibitors in WO 2009/105498 and in WO 2008/115369.

Other pyrimidine derivatives for combating cancer are described in WO 2004/056807 and in WO 2010/055117.

SUMMARY OF THE INVENTION

The invention relates to compounds of the formula I

I

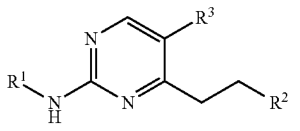

in which $R^1$ denotes $(CH_2)_nAr^1$ or $(CH_2)_nHet^1$, $R^2$ denotes $Ar^2$ or $Het^2$, $R^3$ denotes H, Hal, A, $Het^4$ or CN, $Ar^1$ denotes phenyl which is unsubstituted or mono-, di-, tri-, tetra or pentasubstituted by Hal, A, $(CH_2)_nOH$, $(CH_2)_nOA$, $(CH_2)_nCN$, $NO_2$, $SO_2A$, COOH, COOA, $NH_2$, NHA, $NA_2$, $NHCH_2Ar^1$, CHO, COA, $(CH_2)_nCONH_2$, $(CH_2)_nCONHA$, $(CH_2)_nCONA_2$, $Het^3$, $NHCOHet^3$, $SO_2NH_2$, $SO_2NHA$ and/or NHCOA, $Ar^2$ denotes phenyl which is unsubstituted or mono-, di-, tri-, tetra or pentasubstituted by Hal, A, $(CH_2)_nOH$, $(CH_2)_nOA$, $(CH_2)_nCN$, $NO_2$, $SO_2A$, COOH, COOA, $NH_2$, NHA, $NA_2$, $NHCH_2Ar^1$, CHO, COA, $(CH_2)_nCONH_2$, $(CH_2)_nCONHA$, $(CH_2)_nCONA_2$, $SO_2NH_2$, $NHSO_2A$, $SO_2NHA$, $NA'SO_2A$, $C(R^4R^5)CN$ and/or NHCOA, $Het^1$ denotes a mono- or bicyclic aromatic, unsaturated or saturated heterocycle having 1 to 4 N, O and/or S atoms, which may be unsubstituted or mono-, di-, tri- or tetrasubstituted by Hal, A, $NH_2$, NHA, $NA_2$, COOH, CN, NHCOA, COA, OAr, COOA, $CONH_2$, CONHA, $CONA_2$, CONHAr and/or =O, $Het^2$ denotes a mono- or bicyclic aromatic heterocycle having 1 to 4 N, O and/or S atoms, which may be unsubstituted or mono-, di-, tri- or tetrasubstituted by Hal, A, $NH_2$, NHA, $NA_2$, COOH, COA, COOA, $CONH_2$, CONHA, $CONA_2$, CONHAr, $C(R^4R^5)CN$, $NHSO_2A$, $NASO_2A$, NHCOA, NA'COA, NACHO, $NH(CH_2)_pNHCHO$ and/or =O, Ar denotes phenyl which is unsubstituted or mono-, di- or trisubstituted by Hal and/or A, $R^4$, $R^5$ each, independently of one another, denote H or A, $R^4$ and $R^5$ together also denote alkylene having 2-5 C atoms, in which one $CH_2$ group may be replaced by NH, NA', O or S, $Het^3$ denotes a mono- or bicyclic aromatic, unsaturated or saturated heterocycle having 1 to 3 N, O and/or S atoms, which may be unsubstituted or mono- or disubstituted by A, $NH_2$ and/or =O, $Het^4$ denotes a monocyclic aromatic heterocycle having 1 to 3 N, O and/or S atoms, which may be unsubstituted or mono- or disubstituted by A, A denotes unbranched or branched alkyl having 1-10 C atoms, in which 1-7H atoms may be replaced by F and/or in which one or two non-adjacent CH and/or $CH_2$ groups may be replaced by O, NH, NA', S, SO, $SO_2$ and/or by CH═CH groups, or
cyclic alkyl having 3-7 C atoms, A' denotes unbranched or branched alkyl having 1-6 C atoms, Hal denotes F, Cl, Br or I, n denotes 0, 1, 2, 3 or 4, p denotes 1, 2, 3 or 4, and pharmaceutically usable salts, tautomers and stereoisomers thereof, including mixtures thereof in all ratios.

The invention relates to the compounds of the formula I and salts thereof and to a process for the preparation of compounds of the formula I and pharmaceutically usable salts and stereoisomers thereof, characterised in that a) a compound of the formula II

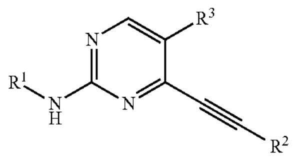

II in which
$R^1$, $R^2$ and $R^3$ have the meanings indicated in Claim 1,
is hydrogenated,
or b) a compound of the formula III

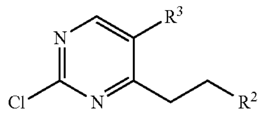

III in which
$R^2$ and $R^3$ have the meanings indicated in Claim 1,
is reacted with a compound of the formula IV $R^1—NH_2$ IV in which $R^1$ has the meaning indicated in claim 1,
and/or
a base or acid of the formula I is converted into one of its salts.

Compounds of the formula I are also taken to mean the hydrates and solvates of these compounds, furthermore pharmaceutically usable derivatives.

The invention also relates to the optically active forms (stereoisomers), the enantiomers, the racemates, the diastereomers and the hydrates and solvates of these compounds. Solvates of the compounds are taken to mean adductions of inert solvent molecules onto the compounds which form owing to their mutual attractive force. Solvates are, for example, monohydrates or dihydrates or alcoholates.

Pharmaceutically usable derivatives are taken to mean, for example, the salts of the compounds according to the invention and also so-called pro-drug compounds.

Prodrug derivatives are taken to mean compounds of the formula I which have been modified by means of, for example, alkyl or acyl groups, sugars or oligopeptides and which are rapidly cleaved in the organism to form the effective compounds according to the invention.

These also include biodegradable polymer derivatives of the compounds according to the invention, as described, for example, in Int. J. Pharm. 115, 61-67 (1995).

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The expression "effective amount" denotes the amount of a medicament or of a pharmaceutical active compound which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:
improved treatment, healing, prevention or elimination of a disease, syndrome, condition, complaint, disorder or side-effects or also the reduction in the advance of a disease, complaint or disorder.

The expression "therapeutically effective amount" also encompasses the amounts which are effective for increasing normal physiological function.

For all radicals which occur more than once, such as, for example, A, their meanings are independent of one another.

A denotes alkyl, is unbranched (linear) or branched and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

A' preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl or benzyl.

OA denotes alkoxy and is preferably, for example, methoxy, ethoxy, propoxy, isopropoxy, butoxy, trifluoromethoxy or cyclopentoxy.

—COA (acyl) preferably denotes acetyl, propionyl, furthermore also butyryl, pentanoyl, hexanoyl or, for example, benzoyl. Hal preferably denotes F, Cl or Br, but also I.

$R^3$ denotes H, Hal, A, $Het^4$ or CN, particularly preferably H, Hal, A or CN, furthermore also $Het^4$.

$Ar^1$ denotes, for example, unsubstituted phenyl, furthermore phenyl which is preferably mono-, di- or trisubstituted, for example by A, fluorine, chlorine, bromine, iodine, hydroxyl, methoxy, ethoxy, propoxy, butoxy, pentyloxy, hexyloxy, nitro, cyano, formyl, acetyl, propionyl, trifluoromethyl, amino, methylamino, ethylamino, dimethylamino, diethylamino, sulfonamido, methylsulfonamido, ethylsulfonamido, propylsulfonamido, butylsulfonamido, dimethylsulfonamido, phenylsulfonamido, carboxyl, methoxycarbonyl, ethoxycarbonyl, aminocarbonyl, $Het^3$ and/or $NHCOHet^3$.

$Ar^1$ particularly preferably denotes phenyl which is mono-, di-, tri-, tetra or pentasubstituted by Hal, $(CH_2)_nCN$, $SO_2A$, $(CH_2)_nCONH_2$, $(CH_2)_nCONHA$, $(CH_2)_nCONA_2$, $Het^3$ and/or $NHCOHet^3$.

$Ar^2$ denotes, for example, unsubstituted phenyl, furthermore preferably phenyl which is mono-, di- or trisubstituted by, for example, A, fluorine, chlorine, bromine, iodine, hydroxyl, methoxy, ethoxy, propoxy, butoxy, pentyloxy, hexyloxy, nitro, cyano, formyl, acetyl, propionyl, trifluoromethyl, amino, methylamino, ethylamino, dimethylamino, diethylamino, benzyloxy, sulfonamido, methylsulfonamido, ethylsulfonamido, propylsulfonamido, butylsulfonamido, dimethylsulfonamido, phenylsulfonamido, carboxyl, methoxycarbonyl, ethoxycarbonyl, aminocarbonyl and/or $C(R^4R^5)CN$.

$Ar^2$ very particularly preferably denotes phenyl which is mono-, di-, tri-tetra- or pentasubstituted by Hal, A, $(CH_2)_nCN$, $SO_2A$, $NHSO_2A$, $NA'SO_2A$ and/or $C(R^4R^5)CN$ $Het^1$, apart from the possible substituents, denotes, for example, 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxan-6-yl, 2,1,3-benzothiadiazol-4- or -5-yl, 2,1,3-benzoxadiazol-5-yl or chromenyl. The heterocyclic radicals may also be partially or fully hydrogenated. $Het^1$ can thus also denote, for example, 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or -6-yl, 2,3-(2-oxomethylenedioxy)phenyl or 3,4-dihydro-2H-1,5-benzodioxepin-6- or -7-yl, furthermore preferably 2,3-dihydrobenzofuranyl or 2,3-dihydro-2-oxofuranyl.

$Het^1$ particularly preferably denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, quinolinyl, quinoxalinyl, quinazolinyl, pyrrolopyridinyl, purinyl, indolyl or indazolyl, tetrahydroquinolyl, dihydrobenzoxazolyl, dihydropyridazinyl, dihydrobenzimidazolyl, dihydrobenzothiazolyl, piperidinyl, pyrrolidinyl, morpholinyl, piperazinyl, imidazolidinyl, oxazolidinyl or tetrahydropyranyl, each of which is unsubstituted or mono-, di- or trisubstituted by A, CN, NHCOA, COA, OAr and/or =O.

$Het^2$ preferably denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, quinolinyl, quinoxalinyl, quinazolinyl, pyrrolopyridinyl, purinyl, indolyl or indazolyl, each of which is mono-, di- or trisubstituted by $C(R^4R^5)CN$, $NHSO_2A$, $NASO_2A$, NHCOA, NA'COA, NACHO, $NH(CH_2)_pNHCHO$ and/or =O.

$Het^3$ preferably denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, quinolinyl, quinoxalinyl, quinazolinyl, pyrrolopyridinyl, purinyl, indolyl or indazolyl, tetrahydroquinolyl, dihydrobenzoxazolyl, dihydropyridazinyl, dihydrobenzimidazolyl, dihydrobenzothiazolyl, piperidinyl, pyrrolidinyl, morpholinyl, piperazinyl, imidazolidinyl, oxazolidinyl or tetrahydropyranyl, each of which is unsubstituted or mono-, di- or trisubstituted by A, $NH_2$ and/or =O.

$Het^4$ denotes a monocyclic aromatic heterocycle having 1 to 3 N, O and/or S atoms, which may be unsubstituted or mono- or disubstituted by A.

$Het^4$ preferably denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl or pyrazinyl, each of which is unsubstituted or mono- or disubstituted by A.

Accordingly, the invention relates, in particular, to the compounds of the formula I in which at least one of the radicals mentioned has one of the preferred meanings indicated above. Some preferred groups of compounds can be expressed by the following sub-formulae Ia to Ig, which correspond to the formula I and in which the radicals not designated in greater detail have the meaning indicated in the case of the formula I, but in which in Ia $Ar^1$ denotes phenyl which is mono-, di-, tri-, tetra or penta-substituted by Hal, $(CH_2)_nCN$, $SO_2A$, $(CH_2)_nCONH_2$, $(CH_2)_nCONHA$, $(CH_2)_nCONA_2$, $Het^3$ and/or $NHCOHet^3$;

in Ib $Ar^2$ denotes phenyl which is mono-, di-, tri-, tetra or penta-substituted by Hal, A, $(CH_2)_nCN$, $SO_2A$, $NHSO_2A$, $NA'SO_2A$ and/or $C(R^4R^5)CN$, in Ic $Het^1$ denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, quinolinyl, quinoxalinyl, quinazolinyl, pyrrolopyridinyl, purinyl, indolyl or indazolyl, tetrahydroquinolyl, dihydro-benzoxazolyl, dihydropyridazinyl, dihydrobenzimidazolyl, dihydrobenzothiazolyl, piperidinyl, pyrrolidinyl, morpholinyl, piperazinyl, imidazolidinyl, oxazolidinyl or tetrahydropyranyl, each of which is unsubstituted or mono-, di- or trisubstituted by A, CN, NHCOA, COA, OAr and/or =O, in Id $Het^2$ denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, quinolinyl, quinoxalinyl, quinazolinyl, pyrrolopyridinyl, purinyl, indolyl or indazolyl, each of which is mono-, di- or trisubstituted by $C(R^4R^5)CN$, $NHSO_2A$, $NASO_2A$, NHCOA, NA'COA, NACHO, $NH(CH_2)_pNHCHO$ and/or =O, in Ie $Het^3$ denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, quinolinyl, quinoxalinyl, quinazolinyl, pyrrolopyridinyl, purinyl, indolyl or indazolyl, tetrahydroquinolyl, dihydro-benzoxazolyl, dihydropyridazinyl, dihydrobenzimidazolyl, dihydrobenzothiazolyl, piperidinyl, pyrrolidinyl, morpholinyl, piperazinyl, imidazolidinyl, oxazolidinyl or tetrahydropyranyl, each of which is un-substituted or mono-, di- or trisubstituted by A, $NH_2$ and/or =O, in If A denotes unbranched or branched alkyl having 1-10 C atoms, in which 1-7H atoms may be replaced by F and/or in which one $CH_2$ group may be replaced by O or NH, in Ig $R^1$ denotes $(CH_2)_nAr^1$ or $(CH_2)_nHet^1$, $R^2$ denotes $Ar^2$ or $Het^2$, $R^3$ denotes H, Hal, A or CN, $Ar^1$ denotes phenyl which is mono-, di-, tri-, tetra or pentasubstituted by Hal, $(CH_2)_nCN$, $SO_2A$, $(CH_2)_nCONH_2$, $(CH_2)_nCONHA$, $(CH_2)_nCONA_2$, $Het^3$ and/or $NHCO-Het^3$, $Ar^2$ denotes phenyl which is mono-, di-, tri-, tetra or pentasubstituted by Hal, A, $(CH_2)_nCN$, $SO_2A$, $NHSO_2A$, $NA'SO_2A$ and/or $C(R^4R^5)CN$, $Het^1$ denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, quinolinyl, quinoxalinyl, quinazolinyl, pyrrolopyridinyl, purinyl, indolyl or indazolyl, tetrahydroquinolyl, dihydrobenzoxazolyl, dihydropyridazinyl, dihydrobenzimidazolyl, dihydrobenzothiazolyl, piperidinyl, pyrrolidinyl, morpholinyl, piperazinyl, imidazolidinyl, oxazolidinyl or tetrahydropyranyl, each of which is un-substituted or mono-, di- or trisubstituted by A, CN, NHCOA, COA, OAr and/or =O, $Het^2$ denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, quinolinyl, quinoxalinyl, quinazolinyl, pyrrolopyridinyl, purinyl, indolyl or indazolyl, each of which is mono-, di- or trisubstituted by $C(R^4R^5)CN$, $NHSO_2A$, $NASO_2A$, NHCOA, NA'COA, NACHO, $NH(CH_2)_pNHCHO$ and/or =O, $Het^3$ denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, quinolinyl, quinoxalinyl, quinazolinyl, pyrrolopyridinyl, purinyl, indolyl or indazolyl, tetrahydroquinolyl, dihydro-benzoxazolyl, dihydropyridazinyl, dihydrobenzimidazolyl, dihydrobenzothiazolyl, piperidinyl, pyrrolidinyl, morpholinyl, piperazinyl, imidazolidinyl, oxazolidinyl or tetrahydropyranyl, each of which is unsubstituted or mono-, di- or trisubstituted by A, $NH_2$ and/or =O, Ar denotes phenyl which is unsubstituted or mono-, di- or trisubstituted by Hal and/or A, $R^4$, $R^5$ each, independently of one another, denote H or A, $R^4$ and $R^5$ together also denote alkylene having 2-5 C atoms, in which one $CH_2$ group may be replaced by NH, NA', O or S, A denotes unbranched or branched alkyl having 1-10 C atoms, in which 1-7H atoms may be replaced by F and/or in which one $CH_2$ group may be replaced by O or NH, A' denotes unbranched or branched alkyl having 1-6 C atoms, Hal denotes F, Cl, Br or I, n denotes 0, 1, 2, 3 or 4, p denotes 1, 2, 3 or 4, and pharmaceutically usable derivatives, solvates, salts and stereoisomers thereof, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use may also be made here of variants known per se which are not mentioned here in greater detail.

If desired, the starting materials can also be formed in situ by not isolating them from the reaction mixture, but instead immediately converting them further into the compounds of the formula I.

The starting compounds of the formulae II, III and IV are generally known. If they are novel, however, they can be prepared by methods known per se.

Compounds of the formula I can preferably be obtained by hydrogenating compounds of the formula II, preferably using hydrogen.

The reaction is carried out by methods which are known to the person skilled in the art. The reaction is carried out in an inert solvent, preferably methanol.

The catalysat used is preferably palladium on active carbon. Depending on the conditions used, the reaction time is between a few minutes and 14 days, the reaction temperature is between about −30° and 140°, normally between −10° and 90°, in particular between about 0° and about 70°.

Compounds of the formula I can furthermore preferably be obtained by reacting compounds of the formula III with compounds of the formula IV. The reaction is carried out in an inert solvent.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents. Particular preference is given n-butanol.

Depending on the conditions used, the reaction time is between a few minutes and 14 days, the reaction temperature is between about −30° and 140°, normally between −10° and 90°, in particular between about 0° and about 70°.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds according to the invention are for the most part prepared by conventional methods. If the compound according to the invention contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline-earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline-earth metal salts calcium and magnesium. Salts of the compounds according to the invention which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; di$(C_1-C_4)$alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl$(C_1-C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds according to the invention are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds according to the invention are formed with metals or amines, such as alkali metals and alkaline-earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active compound which comprises a compound according to the invention in the form of one of its salts, in particular if this salt form imparts improved pharmacokinetic properties on the active compound compared with the free form of the active compound or any other salt form of the active compound used earlier. The pharmaceutically acceptable salt form of the active compound can also provide this active compound for the first time with a desired pharmacokinetic property which it did not have earlier and can even have a positive influence on the pharmacodynamics of this active compound with respect to its therapeutic efficacy in the body.

Compounds according to the invention may be chiral owing to their molecular structure and may accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of the compounds and/or physiologically acceptable salts thereof for the preparation of a medicament (pharmaceutical composition), in particular by non-chemical methods. They can be converted into a suitable dosage form here together with at least one solid, liquid and/or semi-liquid excipient or adjuvant and, if desired, in combination with one or more further active compounds.

The invention furthermore relates to medicaments comprising at least one compound according to the invention and/or pharmaceutically usable derivatives, solvates and stereoisomers thereof, including mixtures thereof in all ratios, and optionally excipients and/or adjuvants.

Pharmaceutical formulations can be administered in the form of dosage units which comprise a predetermined amount of active compound per dosage unit. Such a unit can comprise, for example, 0.1 mg to 3 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active compound per dosage unit. Preferred dosage unit formulations are those which comprise a daily dose or part-dose, as indicated above, or a corresponding fraction thereof of an active compound. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active compound with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a prespecified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds according to the invention and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds according to the invention and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active compound can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active compound can be employed either with a paraffinic or a water-miscible cream base. Alternatively, the active compound can be formulated to give a cream with an oil-in-water cream base or a water-in-oil base.

Pharmaceutical formulations adapted for topical application to the eye include eye drops, in which the active compound is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the present invention depends on a number of factors, including, for example, the age and weight of the human or animal, the precise condition requiring treatment, and its severity, the nature of the formulation and the method of administration, and is ultimately determined by the treating doctor or vet. However, an effective amount of a compound according to the invention for the treatment is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound according to the invention and/or pharmaceutically usable derivatives, solvates and stereoisomers thereof, including mixtures thereof in all ratios, and at least one further medicament active compound.

Further medicament active compounds are preferably chemotherapeutic agents, in particular those which inhibit angiogenesis and thus inhibit the growth and spread of tumour cells; preference is given here to VEGF receptor inhibitors, including robozymes and antisense which are directed to VEGF receptors, and angiostatin and endostatin.

Examples of antineoplastic agents which can be used in combination with the compounds according to the invention generally include alkylating agents, antimetabolites; epidophyllotoxin; an antineoplastic enzyme; a topoisomerase inhibitor; procarbazin; mitoxantron or platinum coordination complexes.

Antineoplastic agents are preferably selected from the following classes: anthracyclins, vinca medicaments, mitomycins, bleomycins, cytotoxic nucleosides, epothilones, discodermolides, pteridines, diynenes and podophyllotoxins.

Particular preference is given in the said classes to, for example, caminomycin, daunorubicin, aminopterin, methotrexate, methopterin, dichloromethotrexate, mitomycin C, porfiromycin, 5-fluorouracil, 6-mercaptopurine, gemcitabine, cytosinarabinoside, podophyllotoxin or podophyllotoxin derivatives, such as, for example, etoposide, etoposide phosphate or teniposide, melphalan, vinblastine, vincristine, leurosidine, vindesine, leurosine and paclitaxel. Other preferred antineoplastic agents are selected from the group estramustine, carboplatin, cyclophosphamide, bleomycin, gemcitabine, ifosamide, melphalan, hexamethylmelamine, thiotepa, cytarabin, idatrexate, trimetrexate, dacarbazine, L-asparaginase, camptothecin, CPT-11, topotecan, arabinosylcytosine, bicalutamide, flutamide, leuprolide, pyridobenzoindole derivatives, interferons and interleukins.

The invention also relates to a set (kit) consisting of separate packs of (a) an effective amount of a compound according to the invention and/or pharmaceutically usable derivatives, solvates and stereoisomers thereof, including mixtures thereof in all ratios, and (b) an effective amount of a further medicament active compound.

The set comprises suitable containers, such as boxes, individual bottles, bags or ampoules. The set may, for example, comprise separate ampoules, each containing an effective amount of a compound according to the invention and/or pharmaceutically usable derivatives, solvates and stereoisomers thereof, including mixtures thereof in all ratios, and an effective amount of a further medicament active compound in dissolved or lyophilised form.

Use

The present compounds are suitable as pharmaceutical active compounds for mammals, especially for humans, in the treatment of tyrosine kinase-induced diseases. These diseases include the proliferation of tumour cells, pathological neovascularisation (or angiogenesis) which promotes the growth of solid tumours, ocular neovascularisation (diabetic retinopathy, age-induced macular degeneration and the like) and inflammation (psoriasis, rheumatoid arthritis and the like).

The present invention encompasses the use of the compounds of the formula I and/or physiologically acceptable salts thereof for the preparation of a medicament for the treatment or prevention of cancer. Preferred carcinomas for the treatment originate from the group cerebral carcinoma, urogenital tract carcinoma, carcinoma of the lymphatic system, stomach carcinoma, laryngeal carcinoma and lung carcinoma. A further group of preferred forms of cancer are monocytic leukaemia, lung adenocarcinoma, small-cell lung carcinomas, pancreatic cancer, glioblastomas and breast carcinoma.

Also encompassed is the use of the compounds according to claim 1 according to the invention and/or physiologically acceptable salts thereof for the preparation of a medicament for the treatment or prevention of a disease in which angiogenesis is implicated.

Such a disease in which angiogenesis is implicated is an ocular disease, such as retinal vascularisation, diabetic retinopathy, age-induced macular degeneration and the like.

The use of compounds of the formula I and/or physiologically acceptable salts and solvates thereof for the preparation of a medicament for the treatment or prevention of inflammatory diseases also falls within the scope of the present invention. Examples of such inflammatory diseases include rheumatoid arthritis, psoriasis, contact dermatitis, delayed hypersensitivity reaction and the like.

Also encompassed is the use of the compounds of the formula I and/or physiologically acceptable salts thereof for the preparation of a medicament for the treatment or prevention of a tyrosine kinase-induced disease or a tyrosine kinase-induced condition in a mammal, in which to this method a therapeutically effective amount of a compound according to the invention is administered to a sick mammal in need of such treatment. The therapeutic amount varies according to the specific disease and can be determined by the person skilled in the art without undue effort.

The present invention also encompasses the use compounds of the formula I and/or physiologically acceptable salts and solvates thereof for the preparation of a medicament for the treatment or prevention of retinal vascularisation.

Methods for the treatment or prevention of ocular diseases, such as diabetic retinopathy and age-induced macular degeneration, are likewise part of the invention. The use for the treatment or prevention of inflammatory diseases, such as rheumatoid arthritis, psoriasis, contact dermatitis and delayed hypersensitivity reaction, as well as the treatment or prevention of bone pathologies from the group osteosarcoma, osteoarthritis and rickets, likewise falls within the scope of the present invention.

The expression "tyrosine kinase-induced diseases or conditions" refers to pathological conditions that depend on the activity of one or more tyrosine kinases. Tyrosine kinases either directly or indirectly participate in the signal transduction pathways of a variety of cellular activities, including proliferation, adhesion and migration and differentiation. Diseases associated with tyrosine kinase activity include proliferation of tumour cells, pathological neovascularisation that promotes the growth of solid tumours, ocular neovascularisation (diabetic retinopathy, age-induced macular degeneration and the like) and inflammation (psoriasis, rheumatoid arthritis and the like).

The compounds of the formula I can be administered to patients for the treatment of cancer, in particular fast-growing tumours.

The invention thus relates to the use of compounds of the formula I, and pharmaceutically usable salts and stereoisomers thereof, including mixtures thereof in all ratios, for the preparation of a medicament for the treatment of diseases in which the inhibition, regulation and/or modulation of kinase signal transduction plays a role.

Preference is given to the use of compounds of the formula I, and pharmaceutically usable salts and stereoisomers thereof, including mixtures thereof in all ratios, for the preparation of a medicament for the treatment of diseases which are influenced by inhibition of tyrosine kinases by the compounds according to Claim 1.

Particular preference is given to the use for the treatment of a disease where the disease is a solid tumour.

The solid tumour is preferably selected from the group of tumours of the lung, squamous epithelium, the bladder, the stomach, the kidneys, of head and neck, the oesophagus, the cervix, the thyroid, the intestine, the liver, the brain, the prostate, the urogenital tract, the lymphatic system, the stomach and/or the larynx.

The solid tumour is furthermore preferably selected from the group lung adenocarcinoma, small-cell lung carcinomas, pancreatic cancer, glioblastomas, colon carcinoma and breast carcinoma.

Preference is furthermore given to the use for the treatment of a tumour of the blood and immune system, preferably for the treatment of a tumour selected from the group of acute myeloid leukaemia, chronic myeloid leukaemia, acute lymphatic leukaemia and/or chronic lymphatic leukaemia.

The disclosed compounds of the formula I can be administered in combination with other known therapeutic agents, including anticancer agents. As used here, the term "anticancer agent" relates to any agent which is administered to a patient with cancer for the purposes of treating the cancer.

The anti-cancer treatment defined herein may be applied as a sole therapy or may involve, in addition to the compound of the invention, conventional surgery or radiotherapy or chemotherapy. Such chemotherapy may include one or more of the following categories of anti-tumour agents:

(i) antiproliferative/antineoplastic/DNA-damaging agents and combinations thereof, as used in medical oncology, such as alkylating agents (for example cis-platin, carboplatin, cyclophosphamide, nitrogen mustard, melphalan, chloroambucil, busulphan and nitrosoureas); antimetabolites (for example antifolates such as fluoropyrimidines like 5-fluorouracil and tegafur, raltitrexed, methotrexate, cytosine arabinoside, hydroxyurea and gemcitabine); antitumour antibiotics (for example anthracyclines, like adriamycin, bleomycin, doxorubicin, daunomycin, epirubicin, idarubicin, mitomycin-C, dactinomycin and mithramycin); antimitotic agents (for example vinca alkaloids, like vincristine, vinblastine, vindesine and vinorelbine, and taxoids, like taxol and taxotere); topoisomerase inhibitors (for example epipodophyllotoxins, like etoposide and teniposide, amsacrine, topotecan, irinotecan and camptothecin) and cell-differentiating agents (for example all-trans-retinoic acid, 13-cis-retinoic acid and fenretinide);

(ii) cytostatic agents, such as antioestrogens (for example tamoxifen, toremifene, raloxifene, droloxifene and iodoxyfene), oestrogen receptor downregulators (for example fulvestrant), antiandrogens (for example bicalutamide, flutamide, nilutamide and cyproterone acetate), LHRH antagonists or LHRH agonists (for example goserelin, leuprorelin and buserelin), progesterones (for example megestrol acetate), aromatase inhibitors (for example as anastrozole, letrozole, vorazole and exemestane) and inhibitors of 5α-reductase, such as finasteride;

(iii) agents which inhibit cancer cell invasion (for example metalloproteinase inhibitors, like marimastat, and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors, such as N-(3-chloro-4-fluorophenyl)-7-methoxy-6-(3-morpholinopropoxy) quinazolin-4-amine (gefitinib, AZD-1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033)), for example inhibitors of the platelet-derived growth factor family and for example inhibitors of the hepatocyte growth factor family;

(v) antiangiogenic agents, such as those which inhibit the effects of vascular endothelial growth factor, (for example the anti-vascular endothelial cell growth factor antibody bevacizumab [Avastin™], compounds such as those disclosed in published international patent applications WO 97/22596, WO 97/30035, WO 97/32856 and WO 98/13354) and compounds that work by other mechanisms (for example linomide, inhibitors of integrin αbβ3 function and angiostatin);

(vi) vessel-damaging agents, such as combretastatin A4 and compounds disclosed in international patent applications WO 99/02166, WO 00/40529, WO 00/41669, WO 01/92224, WO 02/04434 and WO 02/08213;

(vii) antisense therapies, for example those which are directed to the targets listed above, such as ISIS-2503, an anti-Ras antisense;

(viii) gene therapy approaches, including, for example, approaches for replacement of aberrant genes, such as aberrant p53 or aberrant BRCA1 or BRCA2, GDEPT (gene-directed enzyme pro-drug therapy) approaches, such as those using cytosine deaminase, thymidine kinase or a bacterial nitroreductase enzyme, and approaches for increasing patient tolerance to chemotherapy or radiotherapy, such as multi-drug resistance gene therapy; and (ix) immunotherapy approaches, including, for example, ex-vivo and in-vivo approaches for increasing the immunogenicity of patient tumour cells, such as transfection with cytokines, such as interleukin 2, interleukin 4 or granulocyte-macrophage colony stimulating factor, approaches for decreasing T-cell anergy, approaches using transfected immune cells, such as cytokine-transfected dendritic cells, approaches using cytokine-transfected tumour cell lines, and approaches using anti-idiotypic anti-bodies.

The medicaments from Table 1 below are preferably, but not exclusively, combined with the compounds of the formula I.

TABLE 1

| | | |
|---|---|---|
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | Chloroambucil | Temozolomide |
| | Dacarbazine | Semustine |
| | Carmustine | |

TABLE 1-continued

| | | |
|---|---|---|
| Platinum agents | Cisplatin<br>Oxaliplatin<br>Spiroplatin<br>Carboxyphthalatoplatinum<br>Tetraplatin<br>Ormiplatin<br>Iproplatin | Carboplatin<br>ZD-0473 (AnorMED)<br>Lobaplatin (Aetema)<br>Satraplatin (Johnson Matthey)<br>BBR-3464 (Hoffmann-La Roche)<br>SM-11355 (Sumitomo)<br>AP-5280 (Access) |
| Antimetabolites | Azacytidine<br>Gemcitabine<br>Capecitabine<br>5-Fluorouracil<br>Floxuridine<br>2-Chlorodesoxyadenosine<br>6-Mercaptopurine<br>6-Thioguanine<br>Cytarabine<br>2-Fluorodesoxycytidine<br>Methotrexate<br>Idatrexate | Tomudex<br>Trimetrexate<br>Deoxycoformycin<br>Fludarabine<br>Pentostatin<br>Raltitrexed<br>Hydroxyurea<br>Decitabine (SuperGen)<br>Clofarabine (Bioenvision)<br>Irofulven (MGI Pharma)<br>DMDC (Hoffmann-La Roche)<br>Ethynylcytidine (Taiho ) |
| Topoisomerase inhibitors | Amsacrine<br>Epirubicin<br>Etoposide<br>Teniposide or mitoxantrone<br>Irinotecan (CPT-11)<br>7-Ethyl-10-hydroxycamptothecin<br>Topotecan<br>Dexrazoxanet (TopoTarget)<br>Pixantrone (Novuspharrna)<br>Rebeccamycin analogue (Exelixis)<br>BBR-3576 (Novuspharrna) | Rubitecan (SuperGen)<br>Exatecan mesylate (Daiichi)<br>Quinamed (ChemGenex)<br>Gimatecan (Sigma-Tau)<br>Diflomotecan (Beaufour-Ipsen)<br>TAS-103 (Taiho)<br>Elsamitrucin (Spectrum)<br>J-107088 (Merck & Co)<br>BNP-1350 (BioNumerik)<br>CKD-602 (Chong Kun Dang)<br>KW-2170 (Kyowa Hakko) |
| Antitumour antibiotics | Dactinomycin (Actinomycin D)<br>Doxorubicin (Adriamycin)<br>Deoxyrubicin<br>Valrubicin<br>Daunorubicin (Daunomycin)<br>Epirubicin<br>Therarubicin<br>Idarubicin<br>Rubidazon<br>Plicamycinp<br>Porfiromycin<br>Cyanomorpholinodoxorubicin<br>Mitoxantron (Novantron) | Amonafide<br>Azonafide<br>Anthrapyrazole<br>Oxantrazole<br>Losoxantrone<br>Bleomycin sulfate (Blenoxan)<br>Bleomycinic acid<br>Bleomycin A<br>Bleomycin B<br>Mitomycin C<br>MEN-10755 (Menarini)<br>GPX-100 (Gem Pharmaceuticals) |
| Antimitotic agents | Paclitaxel<br>Docetaxel<br>Colchicine<br>Vinblastine<br>Vincristine<br>Vinorelbine<br>Vindesine<br>Dolastatin 10 (NCI)<br>Rhizoxin (Fujisawa)<br>Mivobulin (Warner-Lambert)<br>Cemadotin (BASF)<br>RPR 109881A (Aventis)<br>TXD 258 (Aventis)<br>Epothilone B (Novartis)<br>T 900607 (Tularik)<br>T 138067 (Tularik)<br>Cryptophycin 52 (Eli Lilly)<br>Vinflunine (Fabre)<br>Auristatin PE (Teikoku Hormone)<br>BMS 247550 (BMS)<br>BMS 184476 (BMS)<br>BMS 188797 (BMS)<br>Taxoprexin (Protarga) | SB 408075 (GlaxoSmithKline)<br>E7010 (Abbott)<br>PG-TXL (Cell Therapeutics)<br>IDN 5109 (Bayer)<br>A 105972 (Abbott)<br>A 204197 (Abbott)<br>LU 223651 (BASF)<br>D 24851 (ASTA Medica)<br>ER-86526 (Eisai)<br>Combretastatin A4 (BMS)<br>Isohomohalichondrin-B (PharmaMar)<br>ZD 6126 (AstraZeneca)<br>PEG-Paclitaxel (Enzon)<br>AZ10992 (Asahi)<br>!DN-5109 (Indena)<br>AVLB (Prescient NeuroPharma)<br>Azaepothilon B (BMS)<br>BNP-7787 (BioNumerik)<br>CA-4-prodrug (OXiGENE)<br>Dolastatin-10 (NrH)<br>CA-4 (OXiGENE) |
| Aromatase inhibitors | Aminoglutethimide<br>Letrozole<br>Anastrazole<br>Formestan | Exemestan<br>Atamestan (BioMedicines)<br>YM-511 (Yamanouchi) |
| Thymidylate Synthase inhibitors | Pemetrexed (Eli Lilly)<br>ZD-9331 (BTG) | Nolatrexed (Eximias)<br>CoFactor ™ (BioKeys) |
| DNA antagonists | Trabectedin (PharmaMar)<br>Glufosfamide (Baxter International)<br>Albumin + 32P (Isotope Solutions) | Mafosfamide (Baxter International)<br>Apaziquone (Spectrum Pharmaceuticals)<br>O6-benzylguanine (Paligent) |

TABLE 1-continued

| | | |
|---|---|---|
| | Thymectacin (NewBiotics)<br>Edotreotid (Novartis) | |
| Farnesyl transferase inhibitors | Arglabin (NuOncology Labs)<br>Ionafarnib (Schering-Plough)<br>BAY-43-9006 (Bayer) | Tipifarnib (Johnson & Johnson)<br>Perillyl alcohol (DOR BioPharma) |
| Pump inhibitors | CBT-1 (CBA Pharma)<br>Tariquidar (Xenova)<br>MS-209 (Schering AG) | Zosuquidar trihydrochloride (Eli Lily)<br>Biricodar dicitrate (Vertex) |
| Histone acetyl transferase inhibitors | Tacedinaline (Pfizer)<br>SAHA (Aton Pharma)<br>MS-275 (Schering AG) | Pivaloyloxymethyl butyrate (Titan)<br>Depsipeptide (Fujisawa) |
| Metalloproteinase inhibitors | Neovastat (Aeterna Laboratories)<br>Marimastat (British Biotech) | CMT-3 (CollaGenex)<br>BMS-275291 (Celltech) |
| Ribonucleoside reductase inhibitors | Gallium maltolate (Titan)<br>Triapin (Vion) | Tezacitabine (Aventis)<br>Didox (Molecules for Health) |
| TNF-alpha agonists/antagonists | Virulizin (Lorus Therapeutics)<br>CDC-394 (Celgene) | Revimid (Celgene) |
| Endothelin-A receptor antagonists | Atrasentan (Abbot)<br>ZD-4054 (AstraZeneca) | YM-598 (Yamanouchi) |
| Retinoic acid receptor agonists | Fenretinide (Johnson & Johnson)<br>LGD-1550 (ligand) | Alitretinoin (Ligand) |
| Immunomodulators | Interferon<br>Oncophage (Antigenics)<br>GMK (Progenics)<br>Adenocarcinoma vaccine (Biomira)<br>CTP-37 (AVI BioPharma)<br>JRX-2 (Immuno-Rx)<br>PEP-005 (Peplin Biotech)<br>Synchrovax vaccines (CTL Immuno)<br>Melanoma vaccine (CTL Immuno)<br>p21-RAS vaccine (GemVax) | Dexosome therapy (Anosys)<br>Pentrix (Australian Cancer Technology)<br>JSF-154 (Tragen)<br>Cancer vaccine (Intercell)<br>Norelin (Biostar)<br>BLP-25 (Biomira)<br>MGV (Progenics)<br>!3-Alethin (Dovetail)<br>CLL-Thera (Vasogen) |
| Hormonal and antihormonal agents | Oestrogens<br>Conjugated oestrogens<br>Ethynyloestradiol<br>Chlorotrianisene<br>Idenestrol<br>Hydroxyprogesterone caproate<br>Medroxyprogesterone<br>Testosterone<br>Testosterone propionate<br>Fluoxymesterone<br>Methyltestosterone<br>Diethylstilbestrol<br>Megestrol<br>Tamoxifen<br>Toremofin<br>Dexamethasone | Prednisone<br>Methylprednisolone<br>Prednisolone<br>Aminoglutethimide<br>Leuprolide<br>Goserelin<br>Leuporelin<br>Bicalutamide<br>Flutamide<br>Octreotide<br>Nilutamide<br>Mitotan<br>P-04 (Novogen)<br>2-Methoxyoestradiol (EntreMed)<br>Arzoxifen (Eli Lilly) |
| Photodynamic agents | Talaporfin (Light Sciences)<br>Theralux (Theratechnologies)<br>Motexafin-Gadolinium (Pharmacyclics) | Pd-Bacteriopheophorbid (Yeda)<br>Lutetium-Texaphyrin (Pharmacyclics)<br>Hypericin |
| Tyrosine kinase inhibitors | Imatinib (Novartis)<br>Leflunomide(Sugen/Pharmacia)<br>ZDI839 (AstraZeneca)<br>Erlotinib (Oncogene Science)<br>Canertjnib (Pfizer)<br>Squalamine (Genaera)<br>SU5416 (Pharmacia)<br>SU6668 (Pharmacia)<br>ZD4190 (AstraZeneca)<br>ZD6474 (AstraZeneca)<br>Vatalanib (Novartis)<br>PKI166 (Novartis)<br>GW2016 (GlaxoSmithKline)<br>EKB-509 (Wyeth)<br>EKB-569 (Wyeth) | Kahalide F (PharmaMar)<br>CEP-701 (Cephalon)<br>CEP-751 (Cephalon)<br>MLN518 (Millenium)<br>PKC412 (Novartis)<br>Phenoxodiol O<br>Trastuzumab (Genentech)<br>C225 (ImClone)<br>rhu-Mab (Genentech)<br>MDX-H210 (Medarex)<br>2C4 (Genentech)<br>MDX-447 (Medarex)<br>ABX-EGF (Abgenix)<br>IMC-1C11 (ImClone) |
| Various agents | SR-27897 (CCK-A inhibitor, Sanofi-Synthelabo)<br>Tocladesine (cyclic AMP agonist, Ribapharm)<br>Alvocidib (CDK inhibitor, Aventis)<br>CV-247 (COX-2 inhibitor, Ivy Medical)<br>P54 (COX-2 inhibitor, Phytopharm)<br>CapCell ™ (CYP450 stimulant, Bavarian Nordic) | BCX-1777 (PNP inhibitor, BioCryst)<br>Ranpirnase (ribonuclease stimulant, Alfacell)<br>Galarubicin (RNA synthesis inhibitor, Dong-A)<br>Tirapazamine (reducing agent, SRI International)<br>N-Acetylcysteine (reducing agent, Zambon) |

TABLE 1-continued

| | |
|---|---|
| GCS-IOO (gal3 antagonist, GlycoGenesys) | R-Flurbiprofen (NF-kappaB inhibitor, Encore) |
| G17DT immunogen (gastrin inhibitor, Aphton) | 3CPA (NF-kappaB inhibitor, Active Biotech) |
| Efaproxiral (oxygenator, Allos Therapeutics) | Seocalcitol (vitamin D receptor agonist, Leo) |
| PI-88 (heparanase inhibitor, Progen) | 131-1-TM-601 (DNA antagonist, TransMolecular) |
| Tesmilifen (histamine antagonist, YM BioSciences) | Eflornithin (ODC inhibitor, ILEX Oncology) |
| Histamine (histamine H2 receptor agonist, Maxim) | Minodronic acid (osteoclast inhibitor, Yamanouchi) |
| Tiazofurin (IMPDH inhibitor, Ribapharm) | Indisulam (p53 stimulant, Eisai) |
| Cilengitide (integrin antagonist, Merck KGaA) | Aplidin (PPT inhibitor, PharmaMar) |
| SR-31747 (IL-1 antagonist, Sanofi-Synthelabo) | Rituximab (CD20 antibody, Genentech) |
| CCI-779 (mTOR kinase inhibitor, Wyeth) | Gemtuzumab (CD33 antibody, Wyeth Ayerst) |
| Exisulind (PDE-V inhibitor, Cell Pathways) | PG2 (haematopoiesis promoter, Pharmagenesis) |
| CP-461 (PDE-V inhibitor, Cell Pathways) | Immunol ™ (triclosan mouthwash, Endo) |
| AG-2037 (GART inhibitor, Pfizer) | Triacetyluridine (uridine prodrug, Wellstat) |
| WX-UK1 (plasminogen activator inhibitor, Wilex) | SN-4071 (sarcoma agent, Signature BioScience) |
| PBI-1402 (PMN stimulant, ProMetic LifeSciences) | TransMID-107 ™ (immunotoxin, KS Biomedix) |
| Bortezomib (proteasome inhibitor, Millennium) | PCK-3145 (apoptosis promoter, Procyon) |
| SRL-172 (T-cell stimulant, SR Pharma) | Doranidazole (apoptosis promoter, Pola) |
| TLK-286 (glutathione-S transferase inhibitor, Telik) | CHS-828 (cytotoxic agent, Leo) |
| PT-100 (growth factor agonist, Point Therapeutics) | trans-Retinoic acid (differentiator NIH) |
| Midostaurin (PKC inhibitor, Novartis) | MX6 (apoptosis promoter, MAXIA) |
| Bryostatin-1 (PKC stimulant, GPC Biotech) | Apomine (apoptosis promoter, ILEX Oncology) |
| CDA-II (apoptosis promoter, Everlife) | Urocidin (apoptosis promoter, Bioniche) |
| SDX-101 (apoptosis promoter, Salmedix) | Ro-31-7453 (apoptosis promoter La Roche) |
| Ceflatonin (apoptosis promoter, ChemGenex) | Brostallicin (apoptosis promoter, Pharmacia) |

A combined treatment of this type can be achieved with the aid of simultaneous, consecutive or separate dispensing of the individual components of the treatment. Combination products of this type employ the compounds according to the invention.

The invention relates to compounds of the formula I and pharmaceutically usable salts, tautomers and stereoisomers thereof, including mixtures thereof in all ratios, for use for the treatment of tumours, cancer, tumour formation, growth and spread, arteriosclerosis, eye diseases, such as age-induced macular degeneration, choroidal neovascularisation and diabetic retinopathy, inflammatory diseases, arthritis, thrombosis, fibrosis, glomerulonephritis, neurodegeneration, psoriasis, restenosis, wound healing, transplant rejection, metabolic and diseases of the immune system, autoimmune diseases, cirrhosis, diabetes and diseases of the blood vessels.

Assays

The compounds according to the invention described in the examples were tested by the assays described below and were found to have kinase inhibitory activity. Other assays are known from the literature and could readily be performed by the person skilled in the art (see, for example, Dhanabal et al., *Cancer Res.* 59:189-197; Xin et al., *J. Biol. Chem.* 274:9116-9121; Sheu et al., *Anticancer Res.* 18:4435-4441; Ausprunk et al., *Dev. Biol.* 38:237-248; Gimbrone et al., *J. Natl. Cancer Inst.* 52:413-427; Nicosia et al., *In Vitro* 18:538-549).

FAK Kinase Assay (Autophosphorylation)

The focal adhesion kinase (FAK) assay is carried out either as a 384-well flashplate assay (for example for Topcount measurements) or as a 384-well image flashplate assay (for LEADseeker measurements). 2 nM FAK, 400 nM biotinylated substrate (His-TEV-hsFAK (31 686)(K454R) x biotin) and 1 μM ATP (to which 0.25 Ci of 33P-ATP/well has been added) are incubated at 30° C. for 2 hours with or without test compound in a total volume of 50 μl (60 mM Hepes, 10 mM $MgCl_2$, 1.2 mM dithiothreitol, 0.02% of Brij35, 0.1% of BSA, pH 7.5). The reaction is stopped using 25 μl of 200 mM EDTA. After 30 min at 30° C., the liquid is removed, and each well is washed three times with 100 μl of 0.9% sodium chloride solution. Non-specific reaction is determined in the presence of 1 μM EMD 1076893/0(PF-562271). The radioactivity is measured using Topcount (in the case of the use of flashplates) or using LEADseeker (in the case of the use of image flashplates). Results (for example IC50 values) are calculated using, for example, a Symyx Assay Explorer.

Method for the Cellular Testing of FAK Kinase Inhibitors

For analysis of the cellular activity of FAK, the extent of autophosphorylation of FAK at tyrosine 397 is determined with the aid of a Luminex-based assay in the 96-well format. HT29 cells are sown out with 30,000 cells per well in 100 μl of medium (90% of DMEM/10% of FCS) and incubated on the following day for 30 min with a serial dilution of the test substance (7 concentrations) under serum-free conditions. The cells are subsequently lysed using 90 μl of lysis buffer (20 mM tris/HCl pH 8.0, 150 mM NaCl, 1% of NP40, 10% of glycerol, 1% of phosphatase inhibitor II, 20 mM p-glycerol phosphate, 0.1% of protease inhibitor cocktail III, 0.01% of benzonase) per well, and the lysates are separated off from insoluble cell constituents by means of centrifugation through a 96-well filter plate (0.65 μm). The lysates are incubated at 4° C. overnight with shaking with Luminex beads to which an anti-total FAK antibody is coupled. The detection is carried out on the following day by addition of a P-Y397-FAK antibody and a species-specific PE-labelled secondary antibody. P-Y397-FAK is detected by measurement in the Luminex100 instrument by determination of 100 events per cavity in a measurement time of 60 sec. As pharmacological blank, the signals obtained from cells treated with 30 μM of an FAK reference inhibitor are subtracted from all other batches. The control value used for maximum phosphorylation of FAK at Y397 are the signals from cells treated only with the solvent (0.3% of DMSO). The values of the batches treated with test substance are calculated therefrom as percent of control, and IC50 values are determined by means of Assay Explorer.

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate, evaporated and purified by chromatography on silica gel and/or by crystallisation. Rf values on silica gel; eluent: ethyl acetate/methanol 9:1.

Mass spectrometry (MS): EI (electron impact ionisation) $M^+$

FAB (fast atom bombardment) $(M+H)^+$

ESI (electrospray ionisation) $(M+H)^+$ (unless indicated otherwise)

%

HPLC-MS conditions:

1. Column: Acquity BEH C-18 (2.1×100 mm, 1.7 μm)
2. Mobile phase: A—5 mM ammonium acetate in water B—acetonitrile
3. Flow mode: gradient Time
Point
Flow Rate
(ml/min)

| % | A | % | B |
|---|---|---|---|
| 0.0 | 0.3 | 90 | 10 |
| 1.0 | 0.3 | 90 | 10 |
| 2.0 | 0.3 | 85 | 15 |
| 4.5 | 0.3 | 45 | 55 |
| 6.0 | 0.3 | 10 | 90 |
| 8.0 | 0.3 | 10 | 90 |
| 9.0 | 0.3 | 90 | 10 |
| 10.0 | 0.3 | 90 | 10 |

4. Flow: 0.3 ml/min.
5. UV max.: 254.0 nm
6. Column temperature: 30.0 deg.
7. Sample preparation: acetonitrile+water

*HPLC: La Chrom unit

Chromolite Performance RP18-e 100-4.6 mm

Gradient: ACN/H2O with 0.01% of formic acid

Method: chromolith/chromolith (extended)

Flow rate: 3 ml/min $

Column: XBridge C8, 3.5 μm, 4.6×50 mm;

Solvent A: water+0.1% of TFA;

Solvent B: acetonitrile+0.1% of TFA;

Flow: 2 ml/min;

Gradient: 0 min: 5% of B, 8 min: 100% of B, 8.1 min: 10%; 254 nm

§

NMR spectrum after addition of deuterated trifluoroacetic acid

EXAMPLES

Preparation of N-(2-{2-[2-(4-methanesulfonylphenylamino)pyrimidin-4-yl]ethyl}-phenyl)-N-methyl-methanesulfonamide ("A1")

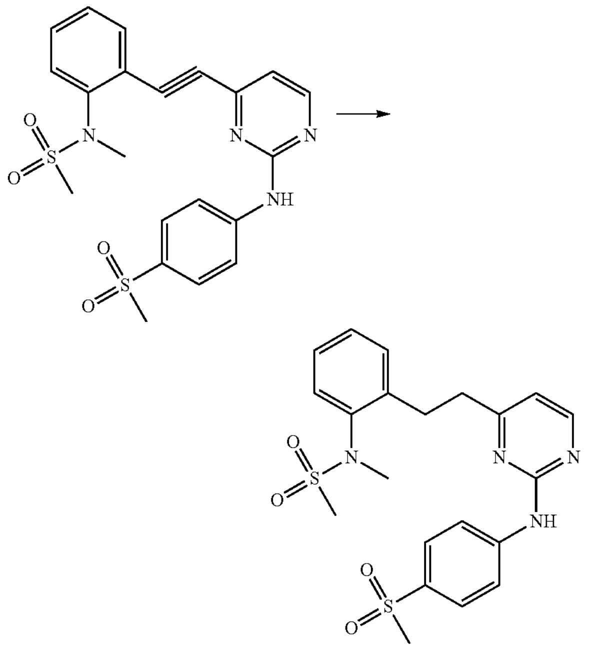

100 mg of N-(2-{2-[2-(4-methanesulfonylphenylamino)pyrimidin-4-yl]ethynyl}-phenyl)-N-methylmethanesulfonamide are dissolved in 1 ml of methanol, and 100 mg of activated carbon (with 10% of Pd) are added. A hydrogen atmosphere is generated, and the suspension is stirred at room temperature for 3 h. The catalyst is subsequently filtered off, and the solvent is removed. The residue is chromatographed on silica gel, giving 50 mg of the title compound as colourless solid;

$^1H$ NMR (500 MHz, DMSO-$d_6$) δ [ppm] J [Hz]:

10.14 (s, 1H), 8.44 (d, J=5.0, 1H), 8.02 (d, J=8.9, 2H), 7.79 (d, J=8.9, 2H), 7.52-7.46 (m, 1H), 7.42-7.36 (m, 1H), 7.36-7.26 (m, 2H), 6.86 (d, J=5.0, 1H), 3.13 (s, 3H), 3.07 (s, 3H), 2.98 (m, 4H).

Preparation of N-methyl-N-(2-{2-[2-(2-oxo-1,2,3,4-tetrahydroquinolin-6-ylamino)pyrimidin-4-yl]ethyl}phenyl)methanesulfonamide ("A2")

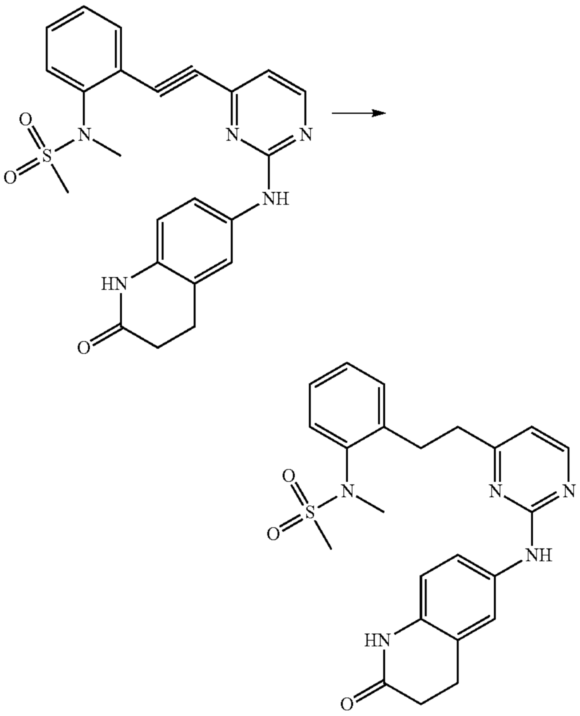

200 mg of N-{2-[2-(2-chloropyrimidin-4-yl)ethyl]phenyl}-N-methylmethanesulfonamide and 70 mg of 6-amino-3,4-dihydroquinolin-2(1H)-one are dissolved in 3 ml of n-butanol and warmed at 120° C. for 12 h in a sealed vessel. After cooling to room temperature, the solvent is removed in vacuo, and the residue is chromatographed on silica gel, giving 50 mg of the title compound as colourless solid;

$^1$H NMR (500 MHz, DMSO-$d_6$) d [ppm] J [Hz]:

9.93 (s, 1H), 9.39 (s, 1H), 8.29 (d, J=5.0, 1H), 7.57 (s, 1H), 7.52-7.45 (m, 2H), 7.40-7.36 (m, 1H), 7.34-7.27 (m, 2H), 6.76 (d, J=8.6, 1H), 6.65 (d, J=5.0, 1H), 3.12 (s, 3H), 3.07 (s, 3H), 2.91 (m, 2H), 2.83 (t, J=7.5, 2H), 2.45-2.38 (m, 2H).

Preparation of 3-(3-{2-[2-(2-oxo-2,3-dihydro-1H-indol-5-ylamino)pyrimidin-4-yl]ethyl}pyridin-2-yl)azetidine-3-carbonitrile ("A16")

1) tert-Butyl 3-cyano-3-(3-iodopyridin-2-yl)azetidine-1-carboxylate

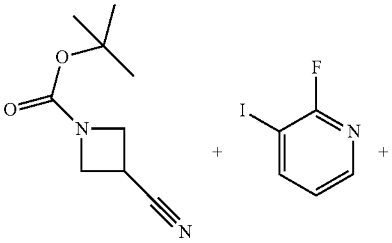

-continued

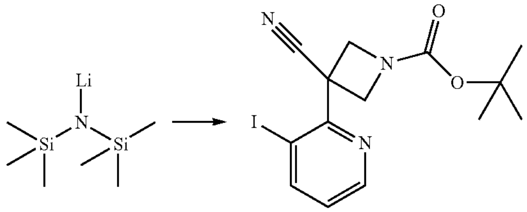

The cyanoazetidine (70 mg, 0.4 mmol) and 2-fluoro-3-iodopyridine (93 mg, 0.4 mmol) is dissolved in dry THF (18 ml) under nitrogen. LiHMDS (lithium hexamethyldisilazide) in THF (0.7 ml, 0.7 mmol) is added to the solution at RT and stirred for a further 45 min. The batch is then added to saturated aqueous ammonium chloride solution and extracted to exhaustion with ethyl acetate. Drying of the organic phase over sodium sulfate and chromatography of the organic residue on silica gel (petroleum ether/ethyl acetate=8:2) gives the product with a yield of 76% (110 mg);

$^1$H NMR (DMSO-$d_6$) δ [ppm] J [Hz]:

ppm 8.65 (dd, 1H) 8.44 (dd, 1H) 7.27 (dd, 1H) 4.63 (d, 2H) 4.49 (d, 2H) 1.39 (s, 9H).

2) tert-Butyl 3-cyano-3-(3-trimethylsilanylethynylpyridin-2-yl)azetidine-1-carboxylate

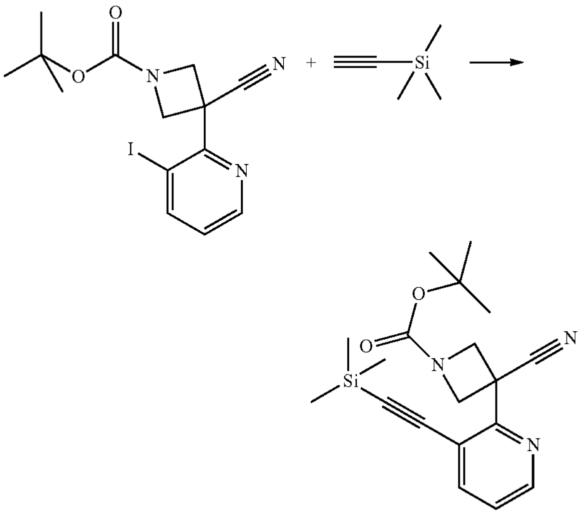

The iodopyridine (790 mg, 2 mmol) is dissolved in 10 ml of acetonitrile under nitrogen, 10 ml of triethlyamine and 40 mg of copper(I) iodide are added. This mixture is degassed for 10 minutes. 72 mg of the catalyst (Pd($PPh_3$)$_2$$Cl_2$) and the alkyne (260 mg, 2.6 mmol) are subsequently added. The batch is stirred at 80° C. for 2 h. The solvent is removed, the residue is taken up with ethyl acetate, and the precipitate formed is separated off by filtration. The organic phase is washed with water and saturated NaCl solution, dried and chromatographed on silica gel with petroleum ether/ethyl acetate=8:2, giving 670 mg of the product (91%);

$^1$H NMR (DMSO-$d_6$) δ [ppm] J [Hz]:

8.63 (dd, 1H), 8.04 (dd, 1H), 7.52 (dd, 1H), 4.64 (d, 2H), 4.44 (d, 2H), 1.39 (s, 9H), 0.29 (s, 9H).

3) tert-Butyl 3-cyano-3-(3-ethynylpyridin-2-yl)azetidine-1-carboxylate

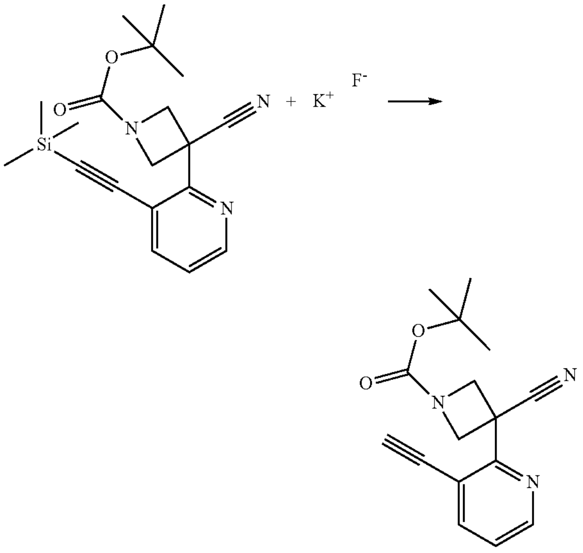

670 mg (1.9 mmol) of the silyl compound are dissolved in 15 ml of methanol, and 220 mg (3.8 mmol) of potassium fluoride are added. After 2 h at RT, the reaction is complete. The solvent is removed in vacuo, and the crude product is chromatographed on silica gel (petroleum ether/ethyl acetate=8:2), giving 500 mg (94%) of the desired product;

$^1$H NMR (DMSO-$d_6$) δ [ppm] J [Hz]: 8.65 (dd, 1H), 8.09 (dd, 1H), 7.54 (dd, 1H), 4.95 (s, 1H), 4.65 (d, 2H), 4.46 (d, 2H), 1.39 (s, 9H).

4) tert-Butyl 3-[3-(2-chloropyrimidin-4-ylethynyl)pyrimidin-2-yl]-3-cyanoazetidine-1-carboxylate

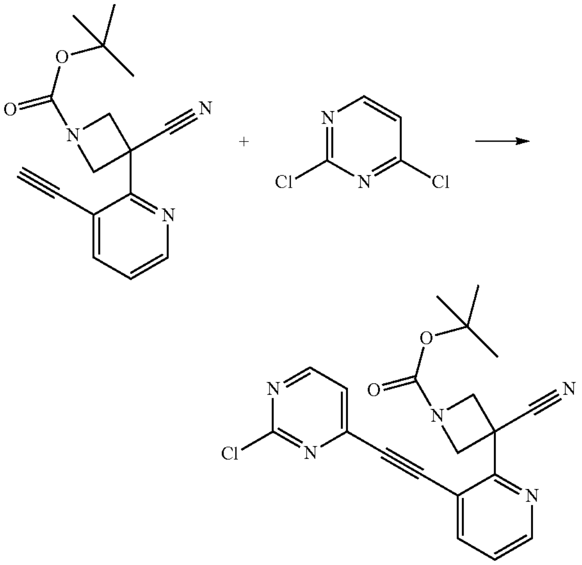

316 mg (2.1 mmol) of 2,4-dichloropyrimidine are dissolved in 5 ml of acetonitrile and 5 ml of triethylamine. After addition of 34 mg of copper(I) iodide, the mixture is degassed for 10 min. 62 mg of $Pd(PPh_3)_2Cl_2$ and 500 mg of the alkyne prepared previously are added, and the mixture is warmed at 80° C. for 2 h. After removal of the solvent in vacuo, the residue is taken up in ethyl acetate, freed from solids, washed with water and saturated NaCl solution, dried and, after re-evaporation, chromatographed on silica gel (petroleum ether/ethyl acetate=6:4), giving 470 mg of the desired product (67%);

$^1$H NMR (DMSO-$d_6$) δ [ppm] J [Hz]:

8.93 (d, 1H), 8.77 (dd, 1H), 8.31 (dd, 1H), 7.86 (d, 1H), 7.66 (dd, 1H), 4.73 (d, 2H), 4.59 (d, 2H), 1.39 (s, 9H)

5) tert-Butyl 3-[3-(2-chloropyrimidin-4-ylethyl)pyrimidin-2-yl]-3-cyanoazetidine-1-carboxylate

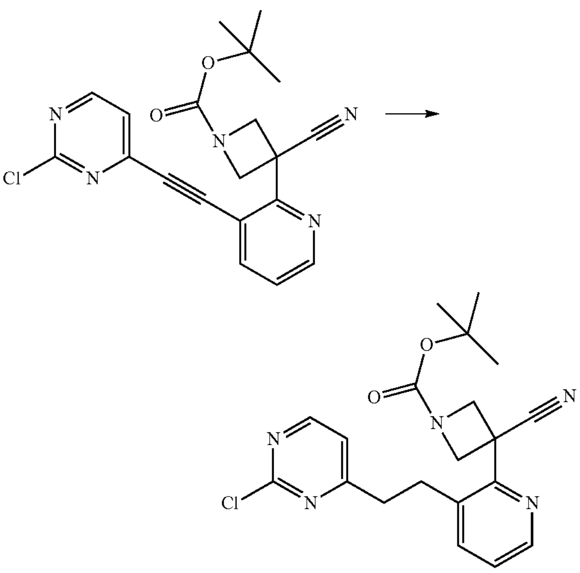

250 mg (0.6 mmol) of the starting material are dissolved in 25 ml of ethyl acetate and hydrogenated at 10 bar with a flow rate of 0.5 ml/min in the H-cube (hydrogenation reactor from Thales Nanotechnology) until the reaction is complete. Removal of the solvent and chromatography on silica gel with petroleum ether/ethyl acetate=6:4 gives 80 mg (31%) of the desired product;

$^1$H NMR (DMSO-$d_6$) δ [ppm] J [Hz]:

8.68 (d, 1H) 8.49 (dd, 1H) 7.91 (dd, 1H) 7.37-7.63 (m, 2H) 4.66 (d, 2H) 4.52 (d, 2H) 3.21 (m, 2H) 2.97 (m, 2H) 1.39 (s, 9H).

6) tert-Butyl 3-cyano-3-(3-{2-[2-(2-oxo-2,3-dihydro-1H-indol-5-ylamino)pyrimidin-4-yl]ethyl}pyridin-2-yl)azetidine-1-carboxylate

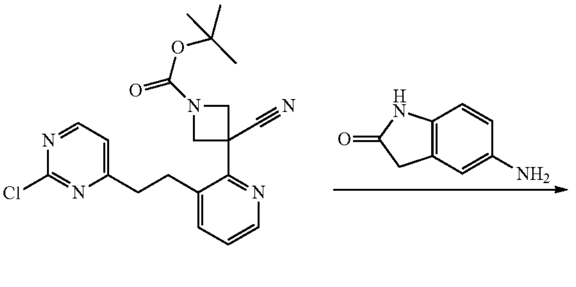

-continued

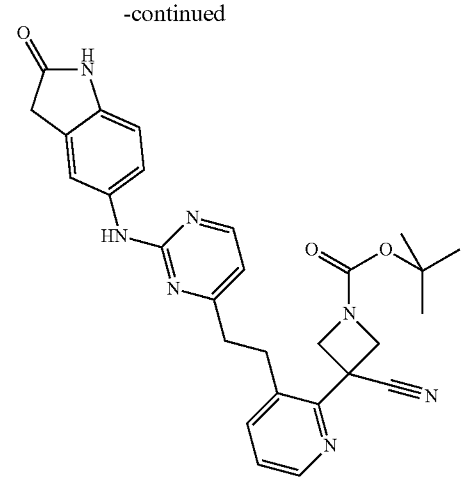

80 mg (0.2 mmol) of the pyrimidine are dissolved in 1 ml of n-butanol, and the oxindol (30 mg, 0.2 mmol) is added. The mixture is then heated at 120° C. for 6 h. After removal of the solvent, the batch is purified by chromatography on silica gel with dichloromethane/methanol=98:2, giving the product in a yield of 18%, and it is employed in the next step without further characterisation.

7) 3-(3-{2-[2-(2-Oxo-2,3-dihydro-1H-indol-5-ylamino)pyrimidin-4-yl]ethyl}-pyridin-2-yl)azetidine-3-carbonitrile ("A16")

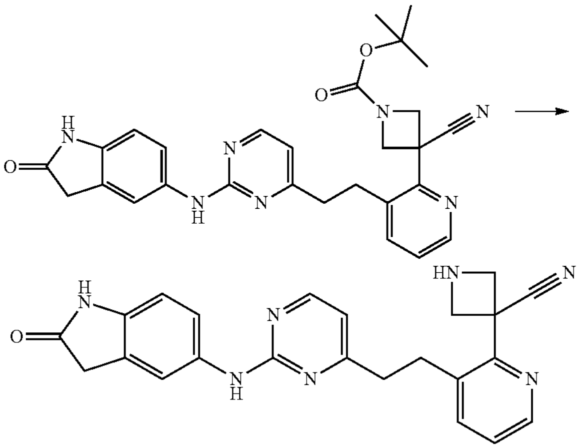

18 mg of the starting compound are dissolved in 0.5 ml of dichloromethane, and 60 mg of trifluoroacetic acid are added. After 8 h at RT, the reaction is complete. The batch is purified on silica gel with dichloromethane/methanol/$NH_4OH$=95/4.5/0.5, giving 8 mg of "A16";

$^1H$ NMR (500 MHz, DMSO-$d_6$) δ [ppm] J [Hz]:

10.20 (s, 1H) 9.73 (br. s., 1H) 9.33 (s, 1H) 9.06 (br. s., 1H) 8.54 (dd, 1H) 8.34 (d, 1H) 7.96 (dd, 1H) 7.65 (d, 1H) 7.42-7.61 (m, 2H) 6.75 (d, 1H) 6.74 (d, 1H) 4.83 (d, 2H) 4.74 (d, 2H) 3.46 (s, 2H) 2.89-3.10 (m, 4H) 3.93 min.

Preparation of (5-fluoro-2-{2-[2-(2-oxo-2,3-dihydro-1H-indol-5-ylamino)pyrimidin-4-yl]ethyl}phenyl)acetonitrile ("A18")

1) 2-(2-((Triethylsilyl)ethynyl)-4-(trifluoromethyl)phenyl)acetonitrile

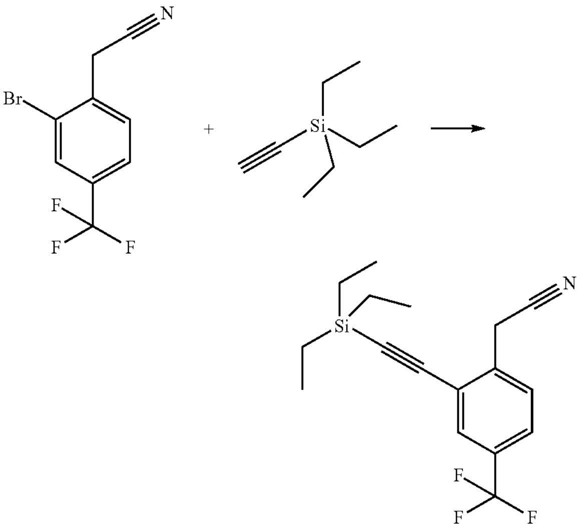

Bis(triphenylphosphine)palladium(II) chloride (0.106 g, 0.151 mmol), copper(I) iodide (0.058 g, 0.303 mmol) and triphenylphospine (0.079 g, 0.303 mmol) are dissolved in a mixture of i-$Pr_2NH$ (11.36 ml)/DMF (3.79 ml) (degassed with $N_2$ for 15 min). 2-(2-Bromo-4-(trifluoromethyl)phenyl)acetonitrile (1.1 g, 3.8 mmol) is added to the resultant orange solution. The mixture is stirred at RT for one hour. Triethyl(ethynyl)silane (1.018 ml, 5.68 mmol) is added dropwise, and the batch is warmed to 80° C. After 1 hour, a saturated, aqueous $NH_4Cl$ solution (50 ml) is added to the strongly dark-coloured batch. After phase separation, the aqueous phase is extracted three times with 50 ml of ethyl acetate each time. The combined organic phases are dried over $Na_2SO_4$ and evaporated to dryness in vacuo. The residue is purified by chromatography on silica gel with a 98:2 mixture of petroleum ether and ethyl acetate, giving 2-(2-((triethylsilyl)ethynyl)-4-(trifluoromethyl)phenyl)acetonitrile (orange oil, 91%, 1.226 g, 3.79 mmol);

$^1H$ NMR (DMSO-$d_6$) δ [ppm] J [Hz]:

7.80-7.89 (m, 2H) 7.73-7.79 (m, 1H) 4.17 (s, 2H) 1.04 (t, 9H) 0.62-0.81 (m, 6H).

2) 2-(2-Ethynyl-5-fluorophenyl)acetonitrile

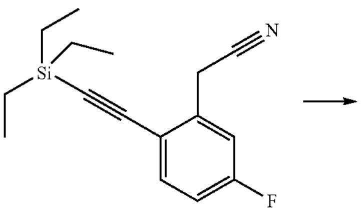

-continued

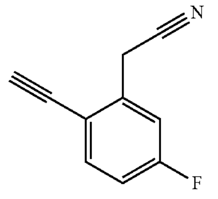

2-(5-Fluoro-2-((triethylsilyl)ethynyl)phenyl)acetonitrile (1.044 g, 3.82 mmol) is dissolved in methanol (38.2 ml), and potassium fluoride (0.887 g, 15.27 mmol) is added. The yellowish solution is stirred at RT for 48 hours. The solvent is subsequently removed in vacuo, and the residue is taken up with water (30 ml). The usual extraction and drying method described under 1) gives 606 mg of the title compound in quantitative yield. (3.81 mmol);

$^{1}$H NMR (DMSO-$d_6$) δ [ppm] J [Hz]:

7.63 (dd, 1H) 7.38 (dd, 1H) 7.26 (td, 1H) 4.58 (s, 1H) 4.09 (s, 2H).

3) 2-(2-((2-Chloropyrimidin-4-yl)ethynyl)-5-fluorophenyl)acetonitrile

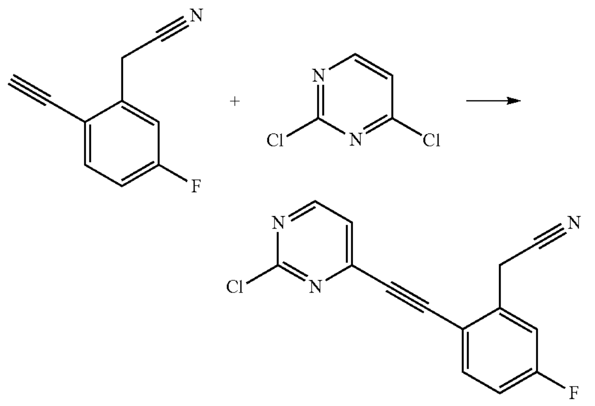

2,4-Dichloropyrimidine (764 mg, 5.13 mmol) is dissolved in degassed acetonitrile (19.700 ml) and triethylamine (19.70 ml). Copper(I) iodide (75 mg, 0.395 mmol) is added, the mixture is degassed again for 10 min., and 2-(2-ethynyl-5-fluorophenyl)acetonitrile (628 mg, 3.95 mmol) and bis(triphenylphosphine)palladium(II) chloride (138 mg, 0.197 mmol) are then added successively to the greenish solution. The reaction phase is warmed at 80° C. for 30 min. The mixture is subsequently worked up, as described above, and the crude mass obtained is purified by chromatography on silica gel (petroleum ether/ethyl acetate=80/20 to 75/25), giving 700 mg of 2-(2-((2-chloropyrimidin-4-yl)ethynyl)-5-fluorophenyl)acetonitrile (2.58 mmol, 65.3% yield) as orange solid;

$^{1}$H NMR (DMSO-$d_6$) δ [ppm] J [Hz]:

8.89 (d, 1H) 7.87 (d, 1H) 7.83-7.90 (m, 1H) 7.48 (dd, 1H) 7.38 (td, 1H) 4.29 (s, 2H).

4) 2-(2-(2-(2-Chloropyrimidin-4-yl)ethyl)-5-fluorophenyl)acetonitrile

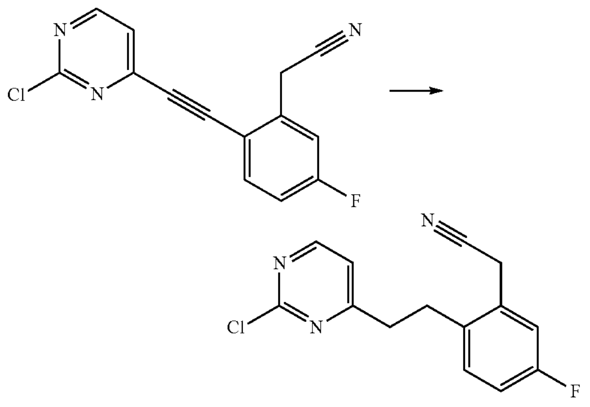

2-(2-((2-Chloropyrimidin-4-yl)ethynyl)-5-fluorophenyl) acetonitrile (0.695 g, 2.56 mmol) is dissolved in ethyl acetate (90 ml), and 10% Pd/C (0.142 g, 0.133 mmol) are added. The suspension is hydrogenated at RT for 24 h under an $H_2$ pressure of 40 psi in a Parr apparatus (hydrogenation apparatus). Since the reaction proceeds very sluggishly, 9 ml of methanol and further catalyst are added (10% Pd/C (0.142 g, 0.133 mmol). Over a further 28 h, 142 mg of catalyst are added three further times until complete conversion is observed. The dark suspension is filtered, washed with ethyl acetate and methanol, and the filtrate is evaporated to dryness in vacuo. Chromatography of the 700 mg of crude product on silica gel with petroleum ether/ethyl acetate=7:3 gives 386 mg of 2-(2-(2-(2-chloropyrimidin-4-yl)ethyl)-5-fluorophenyl)acetonitrile (1.400 mmol, 54.7% yield) as yellowish oil;

$^{1}$H NMR (DMSO-$d_6$) δ [ppm] J [Hz]:

8.66 (d, 1H) 7.49 (d, 1H) 7.31 (dd, 1H) 7.22 (dd, 1H) 7.13 (td, 1H) 4.13 (s, 2H) 2.91-3.18 (m, 4H).

5) "A18"

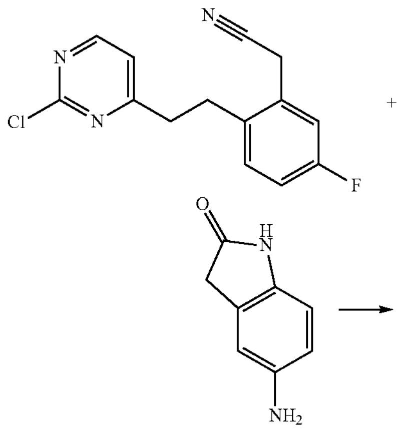

-continued

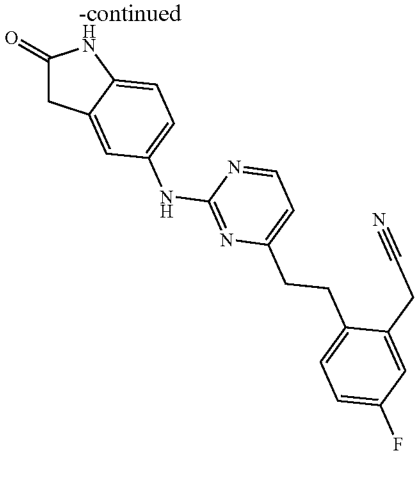

2-(2-(2-(2-Chloropyrimidin-4-yl)ethyl)-5-fluorophenyl) acetonitrile (200 mg, 0.725 mmol) is dissolved in buthanol (6.3 ml), and 5-aminoindolin-2-one (107 mg, 0.725 mmol) is added. The brown suspension is warmed at 120° C. for 6.5 h in a sealed vessel.

After cooling to RT, diethyl ether (15 ml) is added, and the suspension is filtered through a Büchner funnel, and the solid which remains is firstly washed with ether and then purified on silica gel with dichloromethane/methanol=95:5 to 93.7, giving 142 mg of "A18" as yellowish-brown solid. (0.367 mmol, 50.5% yield);

$^1$H NMR (500 MHz, DMSO-$d_6$) δ [ppm] J [Hz]:

10.19 (s, 1H) 9.35 (s, 1H) 8.30 (d, 1H) 7.66 (d, 1H) 7.52 (dd, 1H) 7.31 (dd, 1H) 7.22 (dd, 1H) 7.13 (td, 1H) 6.73 (d, 1H) 6.69 (d, 1H) 4.10 (s, 2H) 3.46 (s, 2H) 2.97-3.09 (m, 2H) 2.83-2.96 (m, 2H).

Preparation of 1-(2-{2-[2-(2-oxo-2,3-dihydro-1H-indol-5-ylamino)pyrimidin-4-yl]ethyl}-4-trifluoromethylphenyl)cyclobutanecarbonitrile ("A19")

1) (4-Trifluoromethylphenyl)cyclobutanecarbonitrile

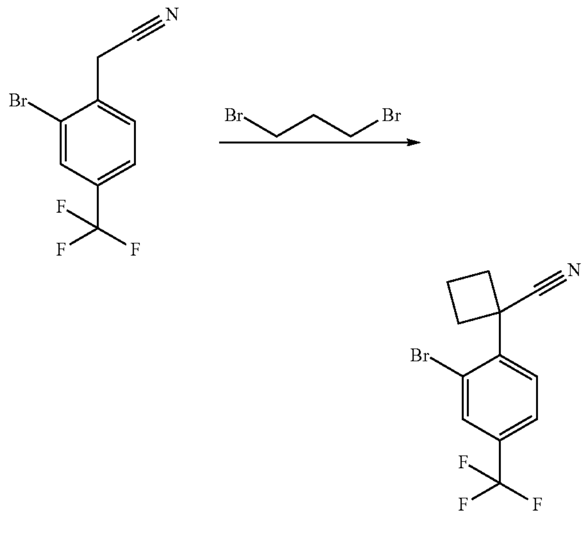

Sodium hydride (380 mg; 9.5 mmol; content 60%) is suspended in 4 ml of DMSO. 1,3-Dibromopropane (920 mg; 4.5 mmol) and (2-bromo-4-trifluoromethylphenyl)carbonitrile are dissolved in 10 ml of DMSO and added dropwise to the sodium hydride suspension. The batch is stirred at RT for 12 h. 10 ml of water are then added, and the mixture is extracted to exhaustion with ethyl acetate. Conventional further work-up and purification on silica gel (petroleum ether/ethyl acetate=95:5) gives (4-trifluoromethylphenyl)cyclobutanecarbonitrile (965 mg, 84%);

$^1$H NMR (DMSO-$d_6$) δ [ppm] J [Hz]:

8.09 (d, 1H), 7.85 (dd, 1H), 7.68 (d, 1H), 2.81-3.03 (m, 2H), 2.65-2.81 (m, 2H), 2.18-2.44 (m, 1H), 1.82-2.00 (m, 1H).

2) 1-(2-Triethylsilanylethynyl-4-trifluoromethylphenyl)cyclobutanecarbonitrile

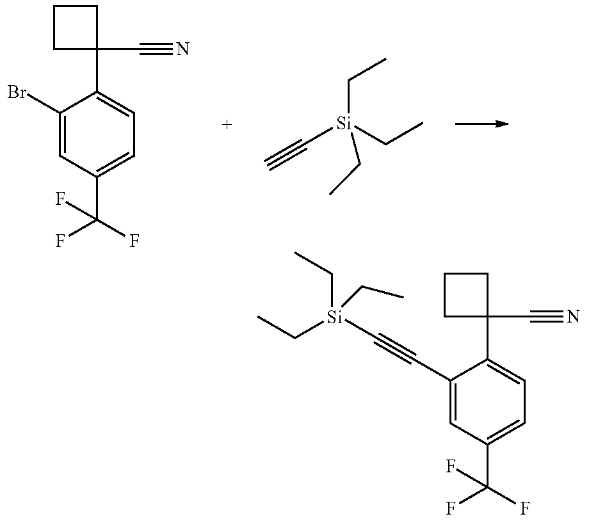

$Pd(PPh_3)_2Cl_2$ (71 mg), copper(I) iodide (38 mg) and $PPh_3$ (52 mg) are suspended in degassed $iPr_2NH$/DMF=3:1. The aryl bromide (750 mg, 2.5 mmol) is added, and, after one hour, 0.7 ml (3.7 mmol) of ethynylsilane is added to the red solution, and the mixture is heated at 80° C. for 18 h. The batch is diluted with 150 ml of ethyl acetate, washed twice with 100 ml of $NH_4Cl$ solution and once with 100 ml of saturated NaCl solution. The organic phase is dried, evaporated, and the residue is purified by chromatography on silica gel (petroleum ether/ethyl acetate=9:1), giving 506 mg of the title compound (56%);

$^1$H NMR (DMSO-$d_6$) δ [ppm] J [Hz]:

7.79-7.87 (m, 2H) 7.66 (d, 1H) 2.63-3.00 (m, 4H) 2.18-2.43 (m, 1H) 1.80-2.07 (m, 1H) 0.94-1.13 (m, 9H) 0.62-0.80 (m, 6H).

3) 1-(Ethynyl-4-trifluoromethylphenyl)cyclobutanecarbonitrile

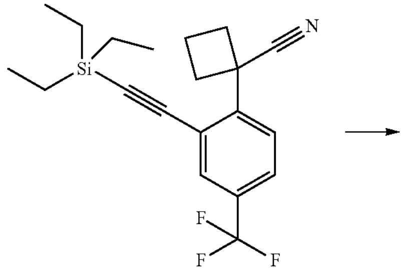

-continued

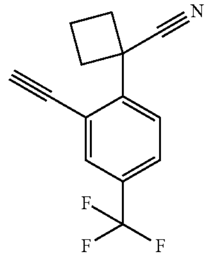

The starting material (500 mg, 1.4 mmol) is dissolved in 5 ml of methanol under nitrogen, and 320 mg (5.7 mmol) of potassium fluoride are added. After 16 h at RT, the solvent is removed, and the residue is dissolved in ethyl acetate (200 ml). After washing with saturated NaCl solution (2*50 ml), the organic phase is dried, and the residue is chromatographed on silica gel with dichloromethane, giving 311 mg (90%) of the desired compound;

$^1$H NMR (DMSO-$d_6$) δ [ppm] J [Hz]:

7.90 (d, 1H) 7.84 (dd, 1H) 7.66 (d, 1H) 4.80 (s, 1H) 2.81-2.94 (m, 2H) 2.66-2.81 (m, 2H) 2.21-2.42 (m, 1H) 1.85-2.02 (m, 1H).

4) 1-[2-(2-Chloropyrimidin-4-ylethynyl)-5-fluorophenyl)-4-trifluoromethylphenyl]cyclobutanecarbonitrile

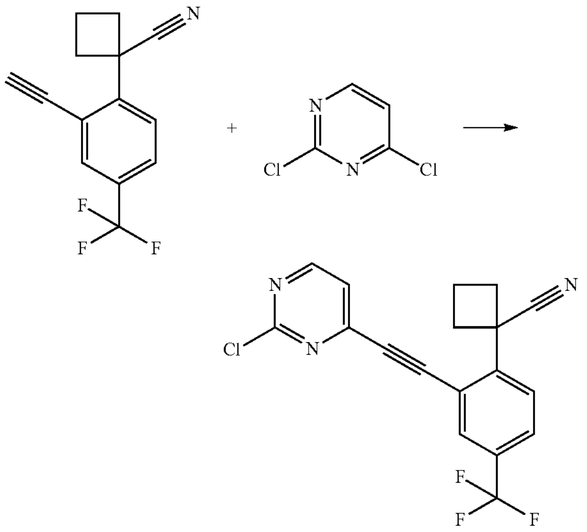

2,4-Dichloropyrimidine (251 mg, 1.7 mmol) is dissolved in degassed acetonitrile (5 ml) and triethylamine (5 ml). Copper(I) iodide (24 mg) is added, the mixture is degassed again for 10 min., and the ethyne (311 mg, 1.2 mmol) and bis(triphenylphosphine)palladium(II) chloride (44 mg) are then added successively to the greenish solution. The reaction phase is warmed at 80° C. for 30 min. The mixture is subsequently worked up, as described above, and the crude mass obtained is purified by chromatography on silica gel (petroleum ether/ethyl acetate=80/20), giving the product as orange solid (256 mg, 0.7 mmol, 57% yield).

$^1$H NMR (DMSO-$d_6$) δ [ppm] J [Hz]:

8.92 (d, 1H) 8.19 (d, 1H) 7.94-8.03 (m, 1H) 7.84 (d, 1H) 7.77 (d, 1H) 2.90-3.09 (m, 2H) 2.75-2.90 (m, 2H) 2.31-2.45 (m, 1H) 1.84-2.08 (m, 1H).

5) 1-[2-(2-Chloropyrimidin-4-ylethyl)-5-fluorophenyl)-4-trifluoromethylphenyl]cyclobutanecarbonitrile

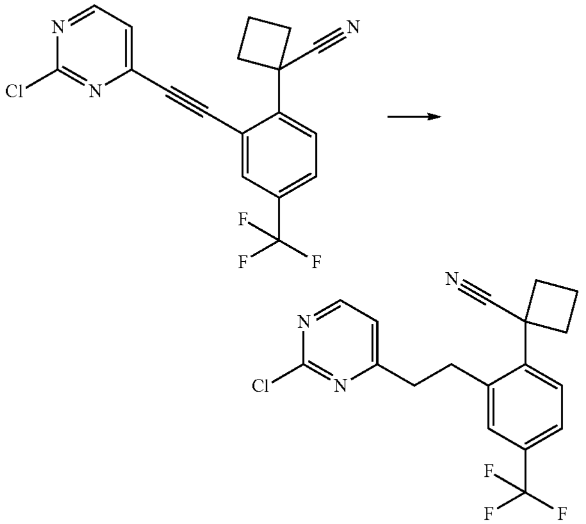

The starting material (256 mg, 0.7 mmol) is dissolved in ethyl acetate (20 ml) and hydrogenated in three runs in the H-cube at 20 bar and 30° C. (flow rate 0.8 ml/min) via a Pd/C (10%) cartridge.

The dark suspension is filtered, washed with ethyl acetate and methanol, and the filtrate is evaporated to dryness in vacuo. Chromatography on silica gel with petroleum ether/ethyl acetate=7:3 gives 202 mg of the title compound (0.5 mmol, 78% yield) as yellowish solid;

$^1$H NMR (DMSO-$d_6$) δ [ppm] J [Hz]:

8.69 (d, 1H) 7.73 (d, 1H) 7.65 (dd, 1H) 7.54 (d, 1H) 7.50 (d, 1H) 3.15-3.23 (m, 2H) 3.03-3.15 (m, 2H) 2.79-2.93 (m, 2H) 2.68-2.79 (m, 2H) 2.29-2.45 (m, 1H) 1.83-2.05 (m, 1H).

6) "A19"

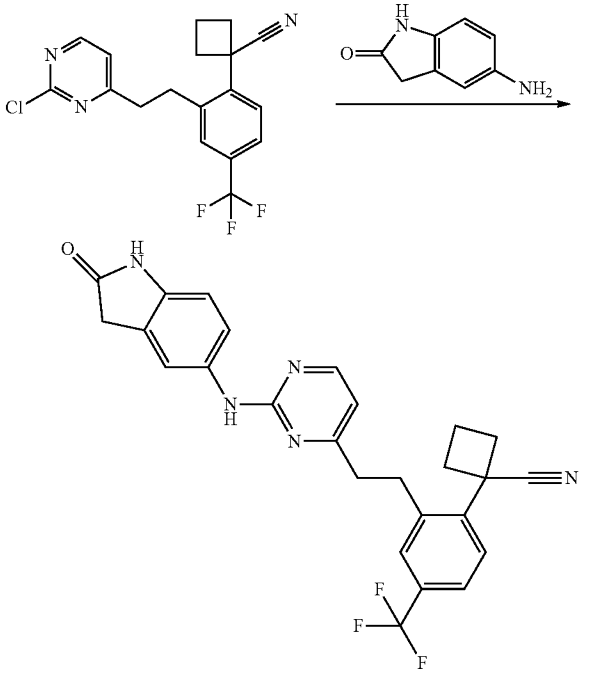

The starting materials are dissolved in 5 ml of n-butanol in a microwave vessel and warmed at 120° C. for 6 h. The batch is subsequently stirred at RT for a further 12 h. Since starting material can still be detected, the mixture is heated again at 120° C. for 3 h. The solvent is subsequently removed in vacuo, and the residue is purified on silica gel (dichloromethane/methanol=99:1). The residue is precipitated using diethyl ether, giving 65 mg of "A19";

$^1$H NMR (500 MHz, DMSO-$d_6$) δ [ppm] J [Hz]:

10.20 (s, 1H) 9.33 (s, 1H) 8.33 (d, 1H) 7.47-7.79 (m, 5H) 6.76 (d, 1H) 6.76 (d, 1H) 3.45 (s, 2H) 2.93-3.19 (m, 4H) 2.65-2.93 (m, 4H) 2.28-2.45 (m, 1 H) 1.79-2.07 (m, 1H).

The following compounds are obtained analogously

| No. | Name/structure | $^1$H NMR (500 MHz, DMSO-$d_6$) δ [ppm] J [Hz] |
|---|---|---|
| "A3" | 6-{4-[2-(3-Methanesulfonylphenyl)ethyl]-pyrimidin-2-ylamino}-3,4-dihydro-1H-quinolin-2-one 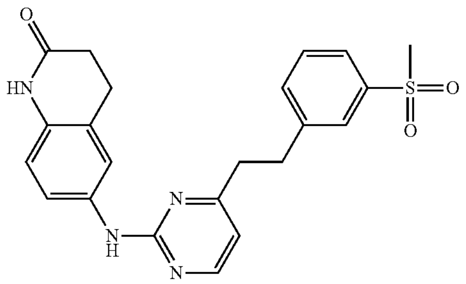 | 9.94 (s, 1H), 9.40 (s, 1H), 8.30 (d, J = 5.0, 1H), 7.80 (s, 1H), 7.75 (d, J = 7.5, 1H), 7.63-7.54 (m, 3H), 7.49 (dd, J = 8.5, 2.3, 1H), 6.75 (d, J = 8.6, 1H), 6.70 (d, J = 5.0, 1H), 3.17 (s, 3H), 3.13 (m, 2H), 2.96 (m, 2H), 2.83 (m, 2H), 2.45-2.38 (m, 2H) |
| "A4" | (4-Methanesulfonylphenyl)-{4-[2-(3-methane-sulfonylphenyl)ethyl]pyrimidin-2-yl}amine 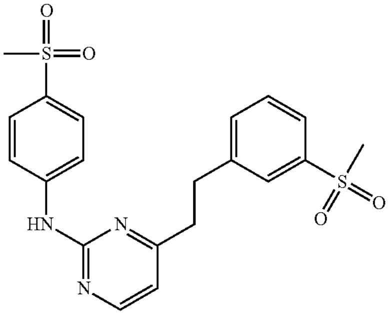 | 10.16 (s, 1H), 8.45 (d, J = 5.0, 1H), 8.01 (d, J = 8.8, 2H), 7.80 (d, J = 9.0, 3H), 7.75 (d, J = 7.5, 1H), 7.59 (m, 2H), 6.90 (d, J = 5.0, 1H), 3.17 (s, 3H), 3.14 (s, 3H), 3.04 (m, 2H) |
| "A5" | N-Methyl-N-(2-{2-[2-(2-oxo-2,3-dihydro-1H-indol-5-ylamino)pyrimidin-4-yl]ethyl}phenyl)-methanesulfonamide 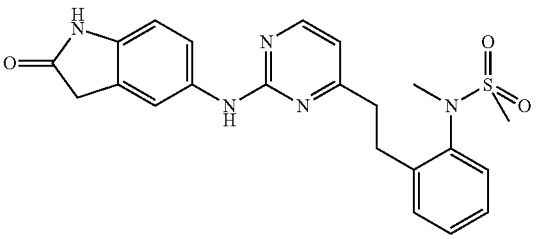 | 10.21 (br. s, 1H), 9.37 (br. s, 1H), 8.29 (d, J = 6.0, 1H), 7.65 (m, 1H), 7.53-7.51 (m, 1H), 7.46 (m, 1H), 7.37 (m, 1H), 7.31-7.29 (m, 2H), 6.72 (d, J = 8.6, 1H), 6.65 (d, J = 6.1, 1H), 3.31 (m, 2H), 3.13 (s, 3H), 3.14 (m, 2H), 3.07 (s, 3H), 2.89 (m, 2H). |

-continued

| No. | Name/structure | $^1$H NMR (500 MHz, DMSO-$d_6$) δ [ppm] J [Hz] |
|---|---|---|
| "A6" | N-Methyl-N-(3-{2-[2-(2-oxo-2,3-dihydro-1H-indol-5-ylamino)pyrimidin-4-yl]ethyl}pyridin-2-yl)-methanesulfonamide 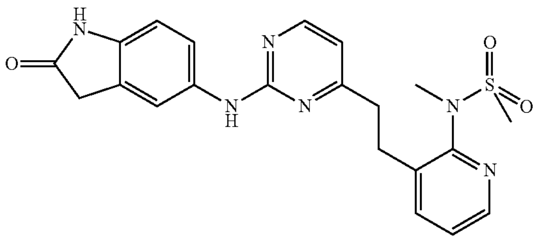 | 10.21 (br. s, 1H), 9.40 (br. s, 1H), 8.39 (dd, J = 1.6, J = 4.4, 1H), 8.29 (d, J = 6.0, 1H), 7.84 (dd, J = 1.6, J = 7.6, 1H), 7.64 (m, 1H), 7.51 (m, 1H), 7.38 (dd, J = 4.8, J = 7.6 1H), 6.71 (d, J = 8.6, 1H), 6.64 (d, J = 6.1, 1H), 3.45 (m, 2H), 3.14 (s, 3H), 3.13-3.12 (m, 2H), 3.11 (s, 3H), 2.92 (m, 2H) |
| "A7" | N-Methyl-N-(3-{2-[2-(2-oxo-1,2,3,4-tetrahydro-quinolin-6-ylamino)pyrimidin-4-yl]ethyl}pyridin-2-yl)methanesulfonamide 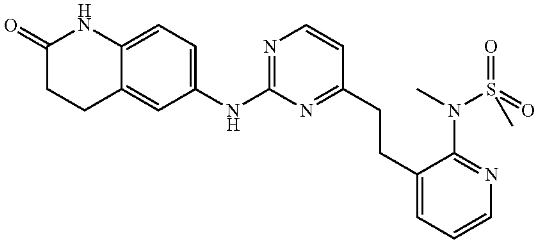 | 9.93 (s, 1H), 9.40 (s, 1H), 8.38 (dd, J = 4.7, 1.8, 1H), 8.29 (d, J = 5.0, 1H), 7.84 (dd, J = 7.7, 1.6, 1H), 7.56 (d, J = 2.0, 1H), 7.47 (dd, J = 8.4, 2.3, 1H), 7.38 (dd, J = 7.7, 4.7, 1H), 6.75 (d, J = 8.5, 1H), 6.65 (d, J = 5.0, 1H), 3.13 (s, 3H), 3.10 (s, 3H), 2.96-2.90 (m, 2H), 2.85-2.80 (m, 2H), 2.44-2.37 (m, 4H) |
| "A8" | N-(3-{2-[2-(4-Methanesulfonylphenylamino)-pyrimidin-4-yl]ethyl}pyridin-2-yl)-N-methyl-methanesulfonamide 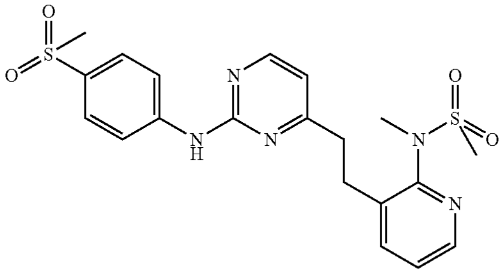 | 10.17 (s, 1H), 8.42 (d, J = 5.0, 2H), 8.01 (m, 2H), 7.79 (d, J = 8.9, 2H), 7.86 (m, 1H), 7.80 (m, 2H), 7.40 (s, 1H), 6.86 (s, 1H), 3.33 (s, 3H), 3.15-3.12 (m, 5H), 3.01 (m, 2H) |
| "A9" | (2-{2-[2-(2-Oxo-2,3-dihydro-1H-indol-5-ylamino)-pyrimidin-4-yl]ethyl}phenyl)acetonitrile 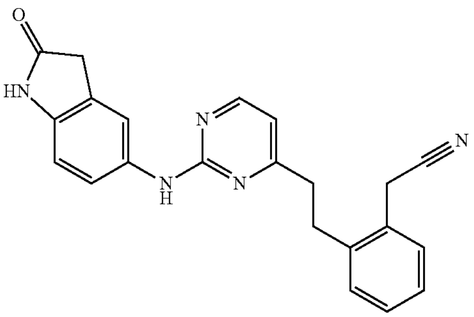 | 10.18 (s, 1 H), 9.35 (s, 1 H), 8.30 (d, 1 H), 7.66 (d, 1 H), 7.53 (dd, 1 H), 7.34-7.41 (m, 1 H), 7.18-7.32 (m, 3 H), 6.73 (d, 1 H), 6.70 (d, 1 H), 4.07 (s, 2 H), 3.46 (s, 2 H), 2.98-3.11 (m, 2 H), 2.82 - 2.97 (m, 2 H) |

-continued

| No. | Name/structure | $^1$H NMR (500 MHz, DMSO-$d_6$) δ [ppm] J [Hz] |
|---|---|---|
| "A10" | N-Methyl-N-(3-{2-[2-(2-oxo-2,3-dihydro-1H-indol-5-ylamino)pyrimidin-4-yl]ethyl}pyridin-2-yl)-acetamide 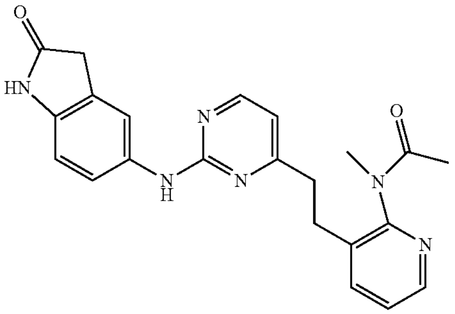 | 10.18 (s, 1H), 9.32 (s, 1H), 8.40 (dd, 1H), 8.29 (d, 1H), 7.95 and 7.74 (dd, 1H), 7.60 (d, 1H), 7.49 (dd, 1H), 7.29 and 7.42 (dd, 1H), 6.73 (d, 1H), 6.68 (d, 1H), 3.46 (s, 2H), 3.05 and 3.22 (s, 3H), 2.87-3.03 (m, 4H), 1.61 and 2.17 (s, 3H) |
| "A11" | (4-Fluoro-2-{2-[2-(2-oxo-2,3-dihydro-1H-indol-5-ylamino)pyrimidin-4-yl]ethyl}phenyl)acetonitrile 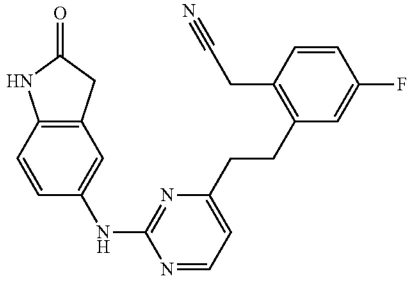 | 10.19 (s, 1 H) 9.35 (s, 1 H) 8.31 (d, 1 H) 7.65 (s, 1 H) 7.33-7.57 (m, 2H) 6.95-7.27 (m, 2 H) 6.58-6.83 (m, 2 H) 4.05 (s, 2 H) 3.46 (s, 2 H) 2.99-3.16 (m, 2 H) 2.80-2.99 (m, 2 H) |
| "A12" | N-Methyl-N-(3-{2-[2-(2-oxo-2,3-dihydro-1H-indol-5-ylamino)pyrimidin-4-yl]ethyl}pyridin-2-yl)-formamide 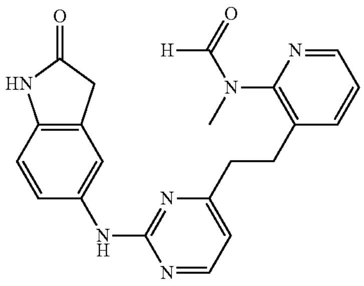 | 10.18 (s, 1 H) 9.18-9.43 (m, 1 H) 8.17-8.48 (m, 3 H) 7.75-8.01 (m, 1H) 7.55-7.71 (m, 1 H) 7.42-7.55 (m, 1 H) 7.23-7.42 (m, 1 H) 6.52-6.86 (m, 2 H) 3.46 (s, 2 H) 3.14 (s, 3 H), 2.96-3.10 (m, 2 H) 2.82-2.96 (m, 2 H) |
| "A13" | 1-(2-{2-[2-(2-Oxo-2,3-dihydro-1H-indol-5-ylamino)pyrimidin-4-yl]ethyl}phenyl)-cyclobutanecarbonitrile 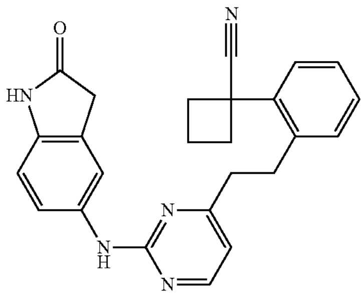 | 10.19 (s, 1 H) 9.34 (s, 1 H) 8.33 (d, 1 H) 7.50-7.71 (m, 2 H) 7.14-7.47 (m, 4 H) 6.77 (s, 1 H) 6.73 (d, 1 H) 3.46 (s, 2 H) 2.87-3.09 (m, 4 H) 2.59-2.87 (m, 4 H) 2.23-2.45 (m, 1 H) 1.83-2.02 (m, 1 H) |

-continued

| No. | Name/structure | $^1$H NMR (500 MHz, DMSO-$d_6$) δ [ppm] J [Hz] |
|---|---|---|
| "A14" | N-[2-(3-{2-[2-(2-Oxo-2,3-dihydro-1H-indol-5-ylamino)pyrimidin-4-yl]ethyl}pyridin-2-ylamino)-ethyl]formamide 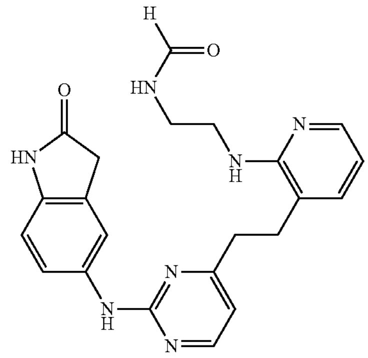 | 10.18 (s, 1 H) 9.31 (s, 1 H) 8.30 (d, 1 H) 8.05-8.10 (m, 1 H) 8.05 (s, 1H) 7.88 (dd, 1 H) 7.63 (d, 1 H) 7.51 (dd, 1 H) 7.20 (dd, 1 H) 6.74 (d, 1 H) 6.71 (d, 1 H) 6.47 (dd, 1 H) 6.07-6.21 (m, 1 H) 3.45 (s, 2 H) 3.38-3.44 (m, 2 H) 3.31-3.37 (m, 2 H) 2.78-2.99 (m, 4 H) |
| "A15" | (2-{2-[2-(2-Oxo-2,3-dihydro-1H-indol-5-ylamino)pyrimidin-4-yl]ethyl}-5-trifluoromethylphenyl)-acetonitrile 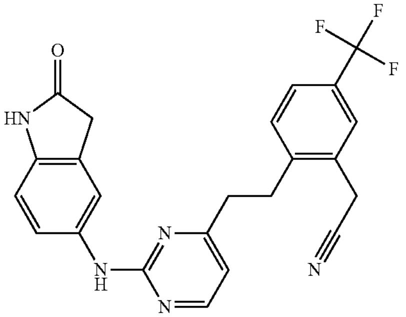 | 10.19 (s, 1 H), 9.35 (s, 1 H), 8.31 (d, 1 H), 7.75 (s, 1 H), 7.59-7.71 (m, 2 H), 7.42-7.58 (m, 2 H), 6.73 (d, 1 H), 6.71 (d, 1 H), 4.21 (s, 2 H), 3.46 (s, 2 H), 3.09-3.20 (m, 2 H), 2.87-3.02 (m, 2 H) |
| "A17" | (2-{2-[2-(2-Oxo-2,3-dihydro-1H-indol-5-ylamino)-pyrimidin-4-yl]ethyl}-4-trifluoromethylphenyl)-acetonitrile 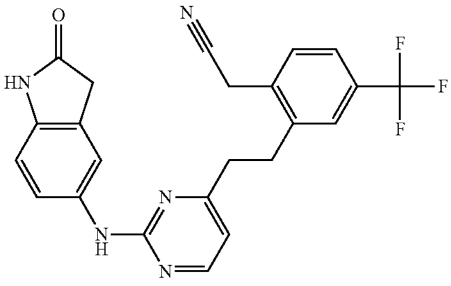 | 10.19 (s, 1 H) 9.34 (s, 1 H) 8.30 (d, 1 H) 7.58-7.72 (m, 4 H) 7.52 (dd, 1H) 6.73 (d, 1 H) 6.70 (d, 1 H) 4.22 (s, 2 H) 3.46 (s, 2H) 3.06-3.21 (m, 2 H) 2.87-3.04 (m, 2 H) |
| "A20" | N-Methyl-N-(3-{2-[2-(2-oxo-2,3-dihydro-benzoxazol-6-ylamino)pyrimidin-4-yl]ethyl}-pyridin-2-yl)methanesulfonamide 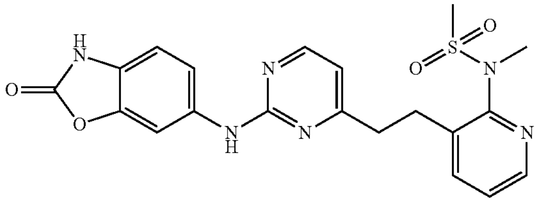 | 11.40 (s, 1H), 9.61 (s, 1H), 8.39 (dd, J = 4.7, 1.8, 1H), 8.35 (d, J = 5.0, 1H), 7.85 (dt, J = 4.5, 2.4, 2H), 7.45 (dd, J = 8.5, 2.0, 1H), 7.39 (dd, J = 7.7, 4.7, 1H), 7.00 (d, J = 8.5, 1H), 6.72 (d, J = 5.0, 1H), 3.18 (m, 2H), 3.15 (s, 4H), 3.13 (s, 3H), 3.01-2.93 (m, 2H) |

-continued

| No. | Name/structure | $^1H$ NMR (500 MHz, DMSO-$d_6$) δ [ppm] J [Hz] |
|---|---|---|
| "A21" | N-Methyl-N-(3-{2-[2-(1-methyl-2-oxo-2,3-dihydro-1H-indol-5-ylamino)pyrimidin-4-yl]ethyl}-pyridin-2-yl)methanesulfonamide 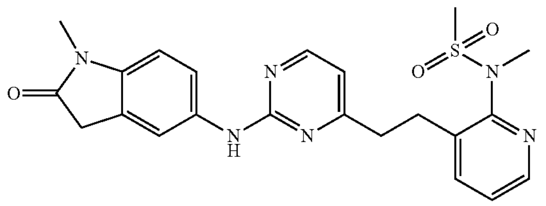 | 9.45 (s, 1H), 8.39 (dd, J = 4.7, 1.8, 1H), 8.30 (d, J = 5.0, 1H), 7.84 (dd, J = 7.7, 1.8, 1H), 7.70 (d, J = 1.8, 1H), 7.60 (dd, J = 8.4, 2.1, 1H), 7.38 (dd, J = 7.7, 4.7, 1H), 6.88 (d, J = 8.5, 1H), 6.67 (d, J = 5.0, 1H), 3.16 (m, 2H), 3.14 (s, 3H), 3.12 (s, 3H), 3.10 (s, 3H), 2.98-2.92 (m, 2H) |
| "A22" | N-(3-{2-[2-(3-Cyanophenylamino)pyrimidin-4-yl]-ethyl}pyridin-2-yl)-N-methylmethanesulfonamide 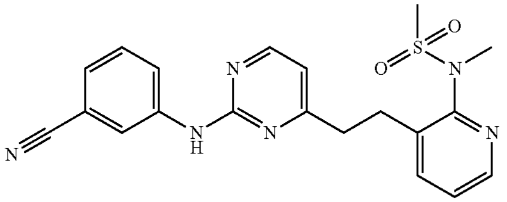 | HPLC-MS; rt; [M+$H^+$]* 2.082 [409.2]* |
| "A23" | N-(3-{2-[2-(3-Cyano-4-fluorophenylamino)-pyrimidin-4-yl]ethyl}pyridin-2-yl)-N-methyl-methanesulfonamide 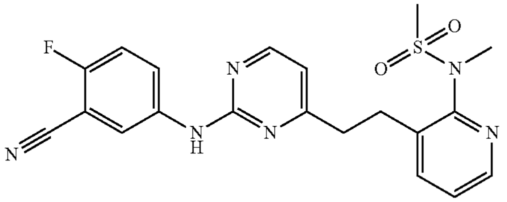 | HPLC-MS; rt; [M+$H^+$]* 2.155 [427.2]* |
| "A24" | N-Methyl-N-[3-(2-{2-[(6-oxo-1,6-dihydro-pyridazin-3-ylmethyl)amino]pyrimidin-4-yl}ethyl)-pyridin-2-yl]methanesulfonamide 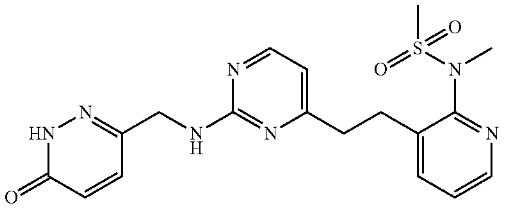 | 12.80 (s, 1H), 8.37 (dd, J = 4.7, 1.8, 1H), 8.18 (d, J = 5.1, 1H), 7.75 (br. m, 2H), 7.37 (d, J = 9.7, 1H), 7.37-7.32 (m, 1H), 6.83 (d, J = 9.7, 1H), 6.54 (d, J = 5.1, 1H), 4.38 (s, 2H), 3.13 (s, 3H), 3.10 (s, 3H), 3.08 (m, 2H), 2.90-2.80 (m, 2H) |
| "A25" | N-(3-{2-[2-(1,3-Dimethyl-2-oxo-2,3-dihydro-1H-benzimidazol-5-ylamino)pyrimidin-4-yl]ethyl}-pyridin-2-yl)-N-methylmethanesulfonamide 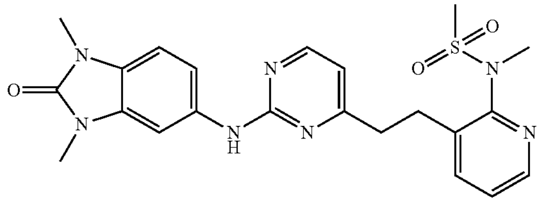 | 9.48 (br. s, 1H), 8.38 (dd, J = 4.7, 1.9, 1H), 8.31 (d, J = 5.0, 1H), 7.85 (dd, J = 7.7, 1.8, 1H), 7.73 (d, J = 1.9, 1H), 7.38 (dd, J = 7.7, 4.7, 1H), 7.33 (dd, J = 8.4, 2.0, 1H), 7.03 (d, J = 8.4, 1H), 6.66 (d, J = 5.0, 1H), 3.30 (s, 3H), 3.29 (s, 3H), 3.21-3.14 (m, 2H), 3.13 (s, 3H), 3.10 (s, 3H), 2.96 (m, 2H) |

-continued

| No. | Name/structure | $^1$H NMR (500 MHz, DMSO-$d_6$) δ [ppm] J [Hz] |
|---|---|---|
| "A26" | N-(3-{[5-Cyano-2-(2-oxo-2,3-dihydrobenzoxazol-6-ylamino)pyrimidin-4-ylamino]methyl}pyridin-2-yl)-N-methylmethanesulfonamide 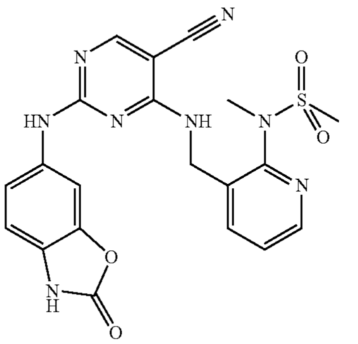 | HPLC-MS; rt; [M+H$^+$]* 1.759 [467.2]* |
| "A27" | N-Methyl-N-(2-{2-[2-(2-oxo-2,3-dihydro-benzoxazol-6-ylamino)pyrimidin-4-yl]ethyl}-phenyl)methanesulfonamide 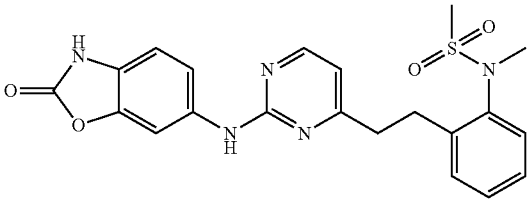 | HPLC-MS; rt; [M+H$^+$]* 1.854 [440.2]* |
| "A28" | N-(2-{2-[2-(3-Cyanophenylamino)pyrimidin-4-yl]-ethyl}phenyl)-N-methylmethanesulfonamide 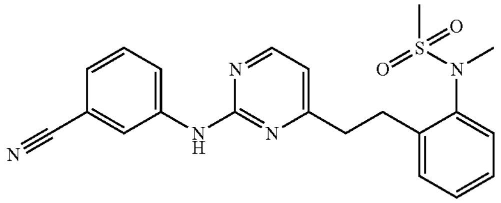 | HPLC-MS; rt; [M+H$^+$]* 2.225 [408.2]* |
| "A29" | N-(2-{2-[2-(3-Cyano-4-fluorophenylamino)-pyrimidin-4-yl]ethyl}phenyl)-N-methyl-methanesulfonamide 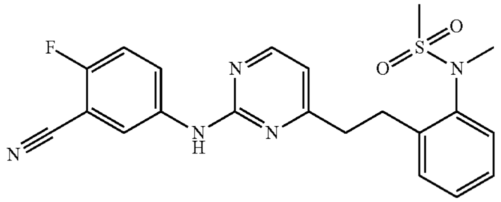 | HPLC-MS; rt; [M+H$^+$]* 2.280 [426.2]* |

-continued

| No. | Name/structure | $^1H$ NMR (500 MHz, DMSO-$d_6$) δ [ppm] J [Hz] |
| --- | --- | --- |
| "A30" | N-Methyl-N-(2-{2-[2-(2-oxo-2,3-dihydro-benzothiazol-5-ylamino)pyrimidin-4-yl]ethyl}-phenyl)methanesulfonamide 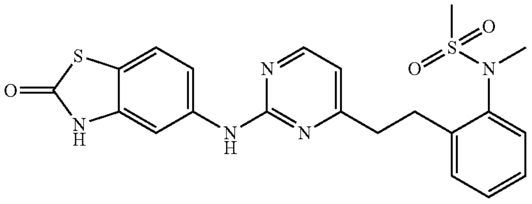 | § 8.41 (d, J = 6.0, 1H), 7.81 (d, J = 1.8, 1 H), 7.53-7.40 (m, 3H), 7.38-7.31 (m, 2H), 7.23 (d, J = 8.6, 1H), 7.04 (d, J = 6.1, 1H), 3.31 (m, 2H), 3.19 (s, 3H), 3.14 (m, 2H), 3.08 (s, 3H) |
| "A31" | N-(2-{2-[2-(1-Acetyl-2,3-dihydro-1H-indol-5-ylamino)pyrimidin-4-yl]ethyl}phenyl)-N-methyl-methanesulfonamide 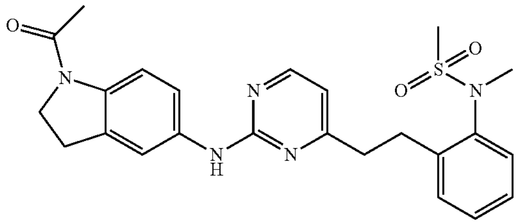 | § 8.39 (d, J = 6.0, 1H), 8.10 (d, J = 8.6, 1H), 7.54-7.46 (m, 2H), 7.42 (dd, J = 5.9, 3.5, 1H), 7.38-7.27 (m, 3H), 7.00 (d, J = 6.0, 1H), 4.14 (m, 2H), 3.21 (m, 5H), 3.21 (m, 2H), 3.12 (s, 3H), 3.08 (s, 3H), 2.18 (s, 3H) |
| "A32" | 2-[3-(4-{2-[2-(Methanesulfonylmethylamino)-phenyl]ethyl}pyrimidin-2-ylamino)phenyl]-N-methylacetamide 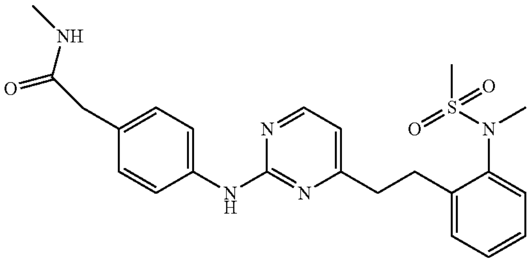 | 9.44 (br. s, 1H), 8.33 (d, J = 5.0, 1H), 7.82 (br. d, J = 4.6, 1H), 7.67 (d, J = 8.6, 2H), 7.51-7.45 (m, 1H), 7.42-7.36 (m, 1H), 7.36-7.23 (m, 2H), 7.14 (d, J = 8.6, 2H), 6.70 (d, J = 5.0, 1H), 3.15 (s, 3H), 3.08 (s, 3H), 2.93 (m, 2H), 2.59 (s, 1H), 2.58 (d, J = 4.6, 3H) |
| "A33" | N-Methyl-N-[2-(2-{2-[4-(3-oxomorpholin-4-yl)-phenylamino]pyrimidin-4-yl}ethyl)phenyl]-methanesulfonamide 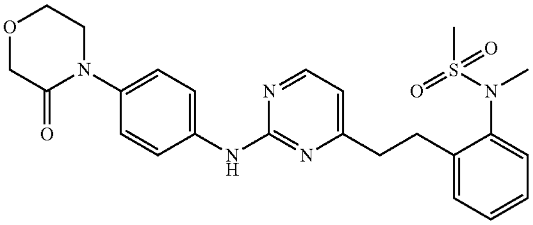 | § 8.48 (d, J = 5.9, 1H), 7.68 (d, J = 8.7, 2H), 7.61-7.55 (m, 1H), 7.51 (m, 1H), 7.47-7.39 (m, 3H), 7.39-7.29 (m, 2H), 7.06 (d, J = 5.9, 1H), 4.20 (m 3H), 4.08-3.97 (m, 3H), 3.78 (dd, J = 9.2, 4.1, 3H), 3.33 (d, J = 9.7, 1H), 3.20 (s, 3H), 3.19-3.11 (m, 4H), 3.07 (s 3H) |

-continued

| No. | Name/structure | $^1$H NMR (500 MHz, DMSO-$d_6$) δ [ppm] J [Hz] |
|---|---|---|
| "A34" | N-[4-(4-{2-[2-(Methanesulfonylmethylamino)-phenyl]ethyl}pyrimidin-2-ylamino)phenyl]-nicotinamide 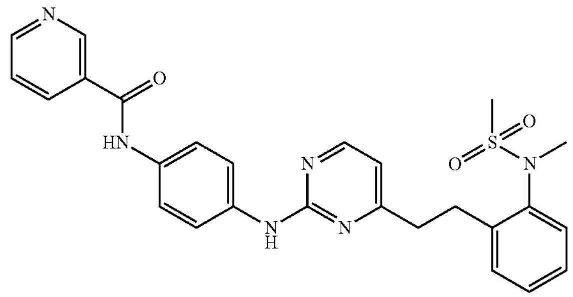 | 10.31 (br. s, 1H), 9.51 (s, 1H), 9.10 (d, J = 1.7, 1H), 8.75 (dd, J = 4.8, 1.6, 1H), 8.34 (d, J = 5.0, 1H), 8.32-8.24 (m, 1H), 7.79-7.72 (m, 2H), 7.64 (d, J = 9.0, 2H), 7.60-7.52 (m, 1H), 7.47 (m, 1H), 7.43-7.36 (m, 1H), 7.36-7.22 (m, 2H), 6.70 (d, J = 5.0, 1H), 3.15 (s, 3H), 3.07 (s, 3H), 3.05 (m, 2H), 2.94 (m, 2H) |
| "A35" | N-Methyl-N-[2-(2-{2-[4-(2-oxopyrrolidin-1-yl)-phenylamino]pyrimidin-4-yl}ethyl)phenyl]-methanesulfonamide 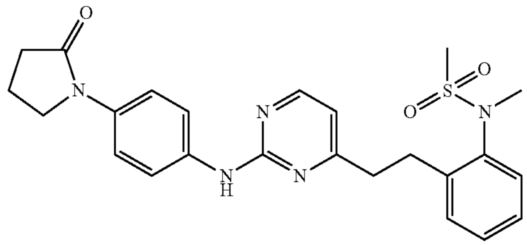 | § 8.35 (d, J = 5.9, 1H), 7.67 (d, J = 9.0, 2H), 7.51 (d, J = 8.9, 2H), 7.41 (m, 1H), 7.35 (dd, J = 6.1, 3.2, 1H), 7.32-7.17 (m, 2H), 6.99 (d, J = 6.2, 1H), 3.81 (m, 2H), 3.28 (m, 2H), 3.12 (s, 3H), 3.08 (m, 2H), 2.99 (s, 3H), 2.46 (m, 2H), 2.12-1.95 (m, 2H) |
| "A36" | N-[2-(2-{2-[3,5-Dichloro-4-(2-oxopyrrolidin-1-yl)-phenylamino]pyrimidin-4-yl}ethyl)phenyl]-N-methylmethanesulfonamide 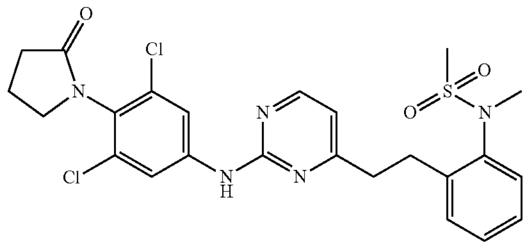 | § 8.48 (d, J = 5.2, 1H), 8.08 (s, 2H), 7.48 (m, 1H), 7.44-7.39 (m, 1H), 7.37-7.27 (m, 2H), 6.92 (d, J = 5.2, 1H), 3.65 (t, J = 6.9, 2H), 3.33 (m, 2H), 3.20 (s, 3H), 3.11 (m, 2H), 3.08 (s, 3H), 2.46 (t, J = 8.0, 2H), 2.29-2.14 (m, 2H) |
| "A37" | N-[2-(2-{2-[3-Cyano-4-(2-oxopiperidin-1-yl)-phenylamino]pyrimidin-4-yl}ethyl)phenyl]-N-methylmethanesulfonamide 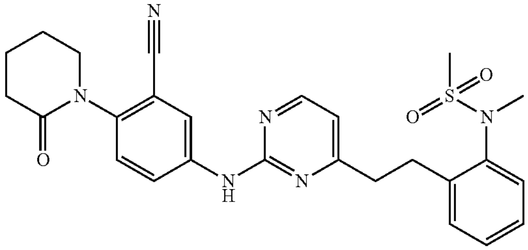 | 10.01 (s, 1H), 8.43 (d, J = 5.0, 1H), 8.26 (d, J = 2.5, 1H), 8.06 (dd, J = 8.9, 2.5, 1H), 7.50-7.45 (m, 1H), 7.41-7.37 (m, 2H), 7.34-7.27 (m, 2H), 6.81 (dd, J = 15.9, 5.0, 1H), 3.61-3.50 (m, 2H), 3.30-3.21 (m, 3H), 3.13 (s, 3H), 3.07 (s, 3H), 3.06-2.88 (m, 3H), 2.41 (m, 2H), 1.95-1.78 (m, 4H) |

-continued

| No. | Name/structure | $^1H$ NMR (500 MHz, DMSO-$d_6$) δ [ppm] J [Hz] |
|---|---|---|
| "A38" | N-[2-(2-{2-[4-(1,3-Dioxo-1,3-dihydroisoindol-2-yl)phenylamino]pyrimidin-4-yl}ethyl)phenyl]-N-methylmethanesulfonamide 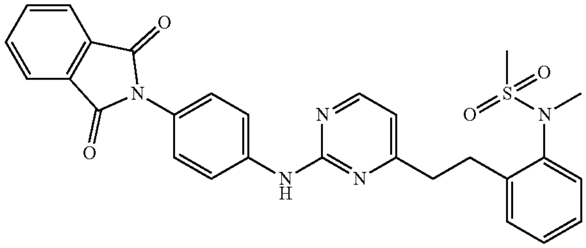 | § 8.51 (d, J = 5.8, 1H), 8.04-7.95 (m, 2H), 7.95-7.87 (m, 2H), 7.83 (d, J = 11.1, 2H), 7.51 (dd, J = 9.2, 2.5, 3H), 7.48-7.41 (m, 1H), 7.41-7.27 (m, 2H), 7.07 (d, J = 5.9, 1H), 3.44-3.28 (m, 1H), 3.20 (s, 3H), 3.19-3.11 (m, 3H), 3.09 (s, 3H) |
| "A39" | N-Methyl-N-[3-(2-{2-[4-(2-oxopyrrolidin-1-yl)-phenylamino]pyrimidin-4-yl}ethyl)pyridin-2-yl]-methanesulfonamide 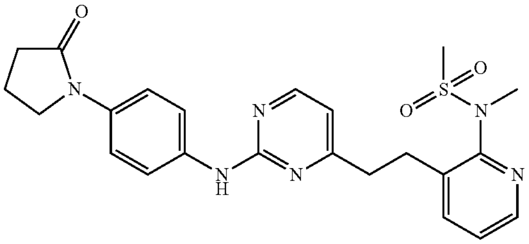 | 9.52 (s, 1H), 8.40 (dd, J = 4.7, 1.8, 1H), 8.34 (d, J = 5.5, 1H), 7.85 (dd, J = 7.7, 1.8, 1H), 7.79-7.69 (m, 2H), 7.60-7.47 (m, 2H), 7.40 (dd, J = 7.7, 4.7, 1H), 6.70 (d, J = 5.0, 1H), 3.81 (t, J = 7.0, 2H), 3.18 (m, 2H), 3.15 (s, 3H), 3.13 (s, 3H), 3.02-2.85 (m, 2H), 2.50-2.39 (m, 2H), 2.15-1.97 (m, 2H) |
| "A40" | N-[4-(4-{2-[2-(Methanesulfonylmethylamino)-pyridin-3-yl]ethyl}pyrimidin-2-ylamino)phenyl]-nicotinamide 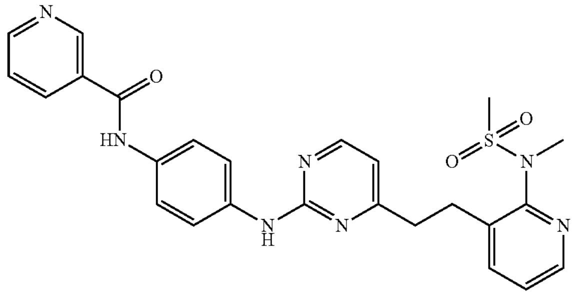 | 9.44 (d, J = 1.7, 1H), 9.12-9.02 (m, 2H), 8.42-8.32 (m, 2H), 8.18 (dd, J = 7.9, 6.0, 1H), 7.86-7.77 (m, 3H), 7.57 (d, J = 8.8, 2H), 7.31 (dd, J = 7.6, 4.8, 1H), 6.98 (d, J = 6.1, 1H), 3.23-3.16 (m, 2H), 3.14 (m, 2H), 3.12 (s, 3H), 3.08 (s, 3H) |
| "A41" | N-Methyl-N-[3-(2-{2-[4-(3-oxomorpholin-4-yl)-phenylamino]pyrimidin-4-yl}ethyl)pyridin-2-yl]-methanesulfonamide 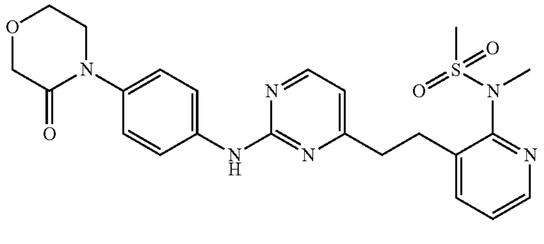 | § 8.38 (dd, J = 18.5, 5.3, 2H), 7.84 (d, J = 7.6, 1H), 7.60 (d, J = 7.5, 1H), 7.42-7.37 (m, 1H), 7.36-7.32 (m, 1H), 6.98 (d, J = 6.0, 1H), 4.18 (s, 1H), 3.97-3.93 (m, 2H), 3.76-3.67 (m, 1H), 3.19 (m, 1H), 3.13 (m, 2H), 3.11 (s, 3H), 3.10 (s, 3H) |

-continued

| No. | Name/structure | $^1H$ NMR (500 MHz, DMSO-$d_6$) δ [ppm] J [Hz] |
|---|---|---|
| "A42" | N-[3-(2-{2-[3-Cyano-4-(2-oxopiperidin-1-yl)-phenylamino]pyrimidin-4-yl}ethyl)pyridin-2-yl]-N-methylmethanesulfonamide 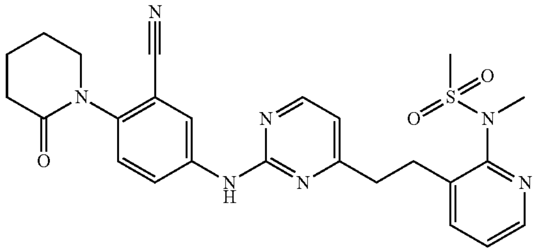 | 10.02 (s, 1H), 8.43 (d, J = 5.0, 1H), 8.42-8.37 (m, 1H), 8.25 (d, J = 2.5, 1H), 8.06 (dd, J = 8.9, 2.5, 1H), 7.86 (dd, J = 7.7, 1.8, 1H), 7.41 (s, 1H), 7.39 (dd, J = 4.6, 3.0, 1H), 6.83 (d, J = 5.0, 1H), 3.57 (m, 2H), 3.50-3.30 (m, 2H), 3.20-3.15 (m, 2 H), 3.15 (s, 3H), 3.12 (s, 3H), 3.04-2.98 (m, 2H), 2.42 (m, 2H), 1.96-1.82 (m, 4H) |
| "A43" | N-[3-(2-{2-[4-(1,3-Dioxo-1,3-dihydroisoindol-2-yl)phenylamino]pyrimidin-4-yl}ethyl)pyridin-2-yl]-N-methylmethanesulfonamide 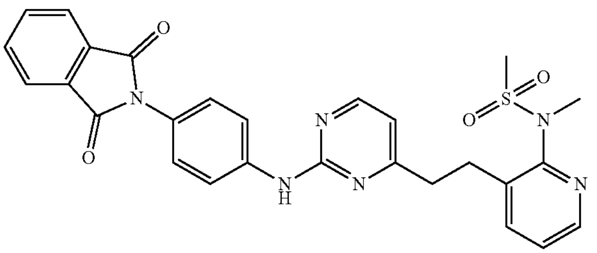 | 9.78 (s, 1H), 8.39 (d, J = 5.0, 2H), 7.98-7.94 (m, 2H), 7.93-7.84 (m, 5H), 7.39 (dd, J = 7.7, 4.7, 1H), 7.34-7.29 (m, 2H), 6.76 (d, J = 5.0, 1H), 3.22-3.16 (m, 2H), 3.14 (s, 3H), 3.12 (s, 3H), 2.99 (m, 2H) |
| "A44" | N-Methyl-N-(5-methyl-3-{2-[2-(2-oxo-2,3 dihydro-1H-indol-5-ylamino)pyrimidin-4-yl]ethyl} pyridin-2-yl)-methanesulfonamide 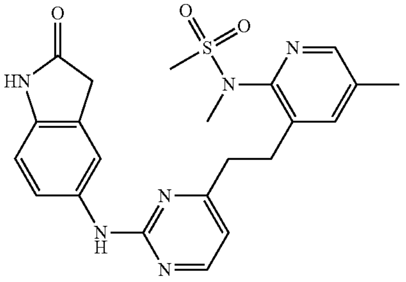 | 10.18 (s, 1 H), 9.36 (s, 1 H), 8.30 (d, 1 H), 8.21 (s, 1 H), 7.59-7.78 (m, 2 H), 7.52 (d, 1 H), 6.73 (d, 1 H), 6.65 (d, 1 H), 3.45 (br. s., 2 H), 3.11 (s, 3 H), 3.09 (s, 3 H), 3.06-3.16 (m, 2 H), 2.91 (t, 2 H), 2.29 (s, 3H) |
| "A45" | 1-(4-Fluoro-2-{2-[2-(2-oxo-2,3-dihydro-1H-indol-5-ylamino)pyrimidin-4-yl]ethyl}phenyl)-cyclobutanecarbonitrile 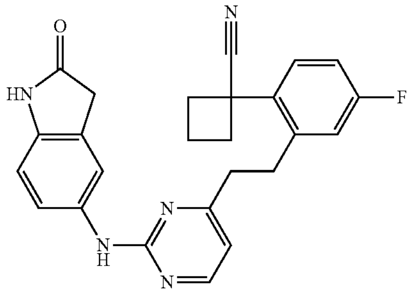 | 10.19 (s, 1 H) 9.33 (s, 1 H) 8.33 (d, 1 H) 7.56-7.64 (m, 2 H) 7.31 (dd, 1H) 7.25 (dd, 1 H) 7.11 (td, 1 H) 6.75 (d, 1 H) 6.74 (d, 1 H) 3.45 (s, 2 H) 2.90-3.14 (m, 4 H) 2.75-2.85 (m, 2H) 2.60-2.71 (m, 2 H) 2.34 (m, 1 H) 1.93 (m, 1 H) |

-continued

| No. | Name/structure | $^1H$ NMR (500 MHz, DMSO-$d_6$) δ [ppm] J [Hz] |
|---|---|---|
| "A46" | 1-(5-Fluoro-2-{2-[2-(2-oxo-2,3-dihydro-1H-indol-5-ylamino)pyrimidin-4-yl]ethyl}phenyl)-cyclobutanecarbonitrile 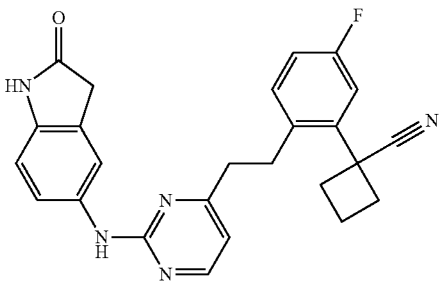 | 10.19 (s, 1 H), 9.34 (s, 1 H), 8.33 (d, 1 H), 7.62 (d, 1 H), 7.58 (dd, 1 H), 7.41 (dd, 1 H), 7.19 (td, 1 H), 7.12 (dd, 1 H), 6.75 (d, 1 H), 6.73 (d, 1 H), 3.45 (s, 2 H), 2.87-3.10 (m, 4 H), 2.61-2.87 (m, 4 H), 2.23-2.40 (m, 1 H), 1.82-2.02 (m, 1 H) |
| "A47" | 1-(2-{2-[2-(2-Oxo-2,3-dihydro-1H-indol-5-yl-amino)pyrimidin-4-yl]ethyl}5-trifluoromethyl-phenyl)cyclobutanecarbonitrile 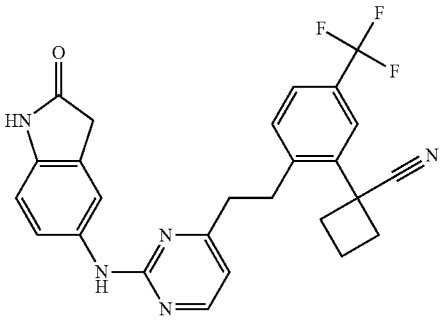 | 10.20 (s, 1 H), 9.34 (s, 1 H), 8.34 (d, 1 H), 7.70-7.75 (m, 1 H), 7.43-7.66 (m, 4 H), 6.75 (d, 1 H), 6.75 (d, 1 H), 3.45 (s, 2 H), 3.06-3.19 (m, 2 H), 2.93-3.06 (m, 2 H), 2.67-2.92 (m, 4 H), 2.29-2.43 (m, 1 H), 1.71-2.07 (m, 1 H) |
| "A48" | (5-Fluoro-4-phenethylpyrimidin-2-yl)phenyl-amine 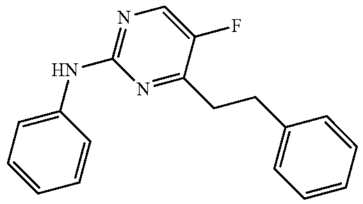 HPLC-MS; rt; [M + $H^+$]* RT: 5.62 min; Mass fould $[M]^+$: 294 | 10.21 (s, 1H), 8.68 (s, 1H), 7.75 (d, J = 7.6, 2H), 7.25 (m, 7H), 7.02 (t, J = 7.4, 1H), 3.06 (m, 4H) |
| "A49" | (5-Methyl-4-phenethylpyrimidin-2-yl)phenyl-amine 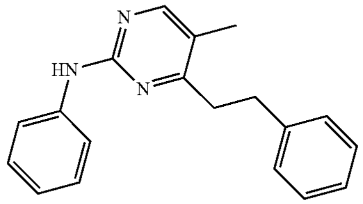 HPLC-MS; rt; [M + $H^+$]* RT: 4.43 min; Mass fould $[M]^+$: 290.3 | 10.20 (s, 1H), 8.66 (s, 1H), 7.75 (d, J = 7.6, 2H), 7.25 (m, 7H), 7.03 (t, J = 7.4, 1H), 3.06 (s, 4H), 2.03 (s, 3H) |

-continued

| No. | Name/structure | $^{1}H$ NMR (500 MHz, DMSO-$d_6$) δ [ppm] J [Hz] |
| --- | --- | --- |
| "A50" | (5-Fluoro-4-phenethylpyrimidin-2-yl)phenyl-amine 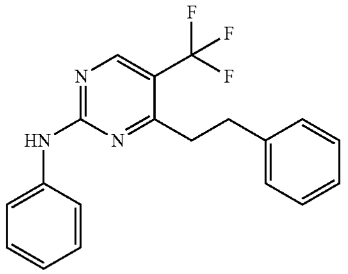 HPLC-MS; rt; [M + $H^+$]* RT: 6.14 min; Mass fould $[M]^+$: 344.0 | 10.22 (s, 1H), 8.67 (s, 1H), 7.74 (d, J = 7.7, 2H), 7.25 (m, 7H), 7.03 (t, J = 7.4, 1H), 3.06 (s, 4H) |
| "A51" | (5-Nitro-4-phenethylpyrimidin-2-yl) phenylamine 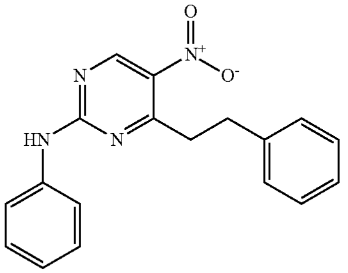 | |
| "A52" | (5-Bromo-4-phenethylpyrimidin-2-yl)phenyl-amine 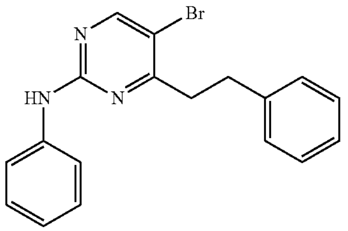 HPLC-MS; rt; [M + $H^+$]* RT: 5.27 min; Mass fould $[M]^+$: 356.0 | 9.73 (s, 1H), 8.35 (d, J = 5.0, 1H), 7.75 (d, J = 8.8, 2H), 7.42 (d, J = 8.8, 2H), 7.31-7.20 (m, 4H), 7.17 (t, J = 6.9, 1H), 6.77 (d, J = 5.0, 1H), 3.05-2.98 (m, 2H), 2.97-2.89 (m, 2H) |
| "A53" | 5-{5-Fluoro-4-[2-(4-fluorophenyl)ethyl]pyrimidin-2-ylamino}-1,3-dihydroindol-2-one 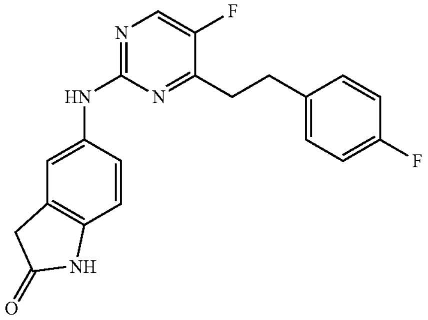 | |

-continued

| No. | Name/structure | $^1$H NMR (500 MHz, DMSO-$d_6$) δ [ppm] J [Hz] |
|---|---|---|
| "A54" | 5-{4-[2-(4-Bromo-2-fluorophenyl)ethyl]-5-fluoro-pyrimidin-2-ylamino}-1,3-dihydroindol-2-one 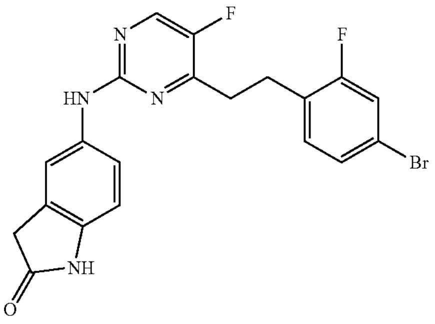 | |
| "A55" | 5-(5-Fluoro-4-{2-[2-(propane-1-sulfonyl)phenyl]-ethyl]pyrimidin-2-ylamino}-1,3-dihydroindol-2-one 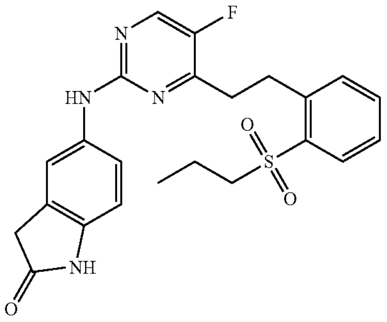 | |
| "A56" | 6-{5-Fluoro-4-[2-(4-fluorophenyl)ethyl]pyrimidin-2-ylamino}-3,4-dihydro-1H-quinolin-2-one 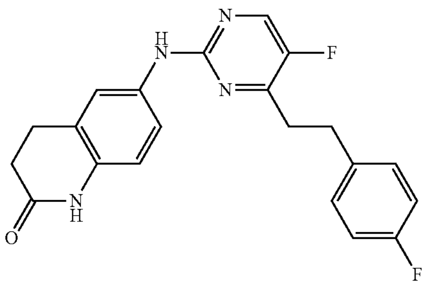 | 9.94 (s, 1H), 9.47 (s, 1H), 8.34 (d, J = 1.7, 1H), 7.51 (s, 1H), 7.42 (dd, J = 8.6, 2.2, 1H), 7.25 (dd, J = 8.5, 5.7, 2H), 7.08 (t, J = 8.9, 2H), 6.74 (d, J = 8.6, 1H), 3.00 (m, 4H), 2.81 (m, 2H), 2.44-2.38 (m, 2H) |

HPLC-MS; rt; [M + H$^+$]*
RT: 4.53 min;
Mass fould [M]$^+$: 381.2

-continued
| No. | Name/structure | $^1$H NMR (500 MHz, DMSO-d$_6$) δ [ppm] J [Hz] |
|---|---|---|
| "A57" | 6-{4-[2-(4-Bromo-2-fluorophenyl)ethyl]-5-fluoro-pyrimidin-2-ylamino}-3,4-dihydro-1H-quinolin-2-one 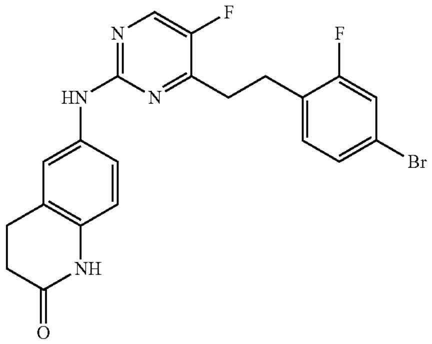 | |
| "A58" | 6-(5-Fluoro-4-{2-[2-(propane-1-sulfonyl)phenyl]-ethyl]pyrimidin-2-ylamino}-3,4-dihydro-1H-quinolin-2-one 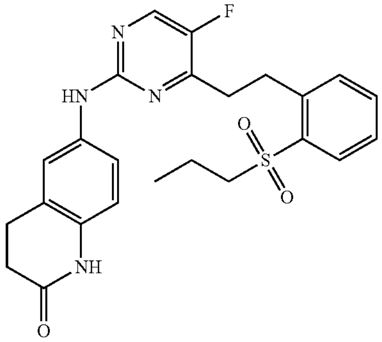 | |
| "A59" | 6-{5-Fluoro-4-[2-(4-fluorophenyl)ethyl]pyrimidin-2-ylamino}-3H-benzoxazol-2-one 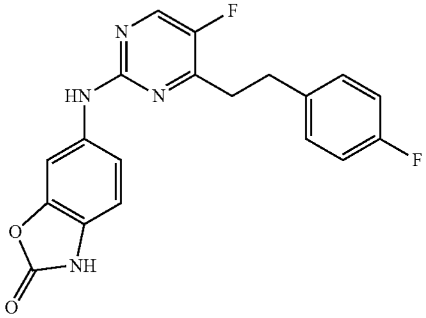 | |

-continued
| No. | Name/structure | $^1H$ NMR (500 MHz, DMSO-$d_6$) δ [ppm] J [Hz] |
|---|---|---|
| "A60" | 6-{4-[2-(4-Bromo-2-fluorophenyl)ethyl]-5-fluoro-pyrimidin-2-ylamino}-3H-benzoxazol-2-one 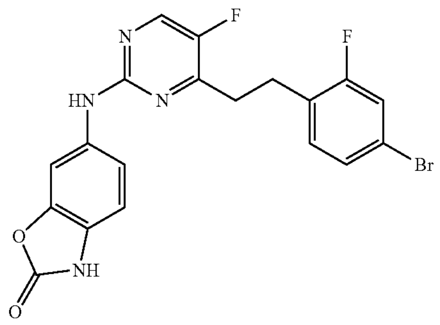 | |
| "A61" | 6-(5-Fluoro-4-{2-[2-(propane-1-sulfonyl)phenyl]-ethyl]pyrimidin-2-ylamino}-3H-benzoxazol-2-one 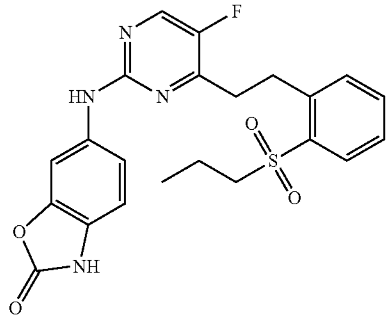 | |
| "A62" | 5-{4-[2-(4-Fluorophenyl)ethyl]-5-methyl-pyrimidin-2-ylamino}-1,3-dihydroindol-2-one 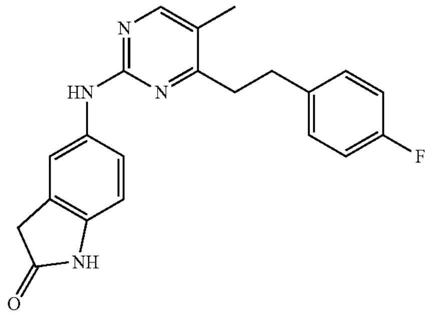 | |

-continued

| No. | Name/structure | $^1H$ NMR (500 MHz, DMSO-$d_6$) δ [ppm] J [Hz] |
|---|---|---|
| "A63" | 5-{4-[2-(4-Bromo-2-fluorophenyl)ethyl]-5-methylpyrimidin-2-ylamino}-1,3-dihydroindol-2-one 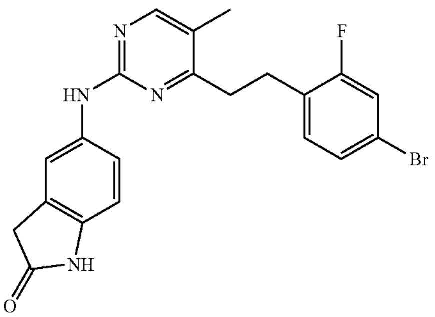 | |
| "A64" | 5-(5-Methyl-4-{2-[2-(propane-1-sulfonyl)phenyl]-ethyl}pyrimidin-2-ylamino}-1,3-dihydroindol-2-one 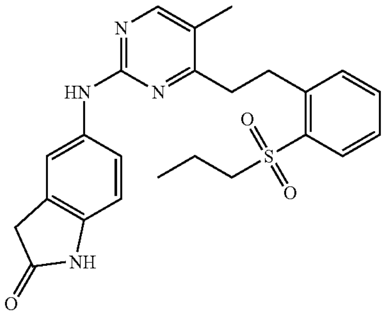 | |
| "A65" | 6-{4-[2-(4-Fluorophenyl)ethyl]-5-methyl-pyrimidin-2-ylamino}-3,4-dihydro-1H-quinolin-2-one 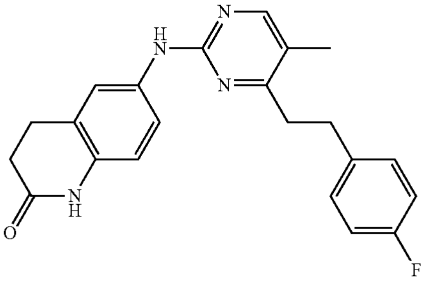 | 9.91 (s, 1H), 9.22 (s, 1H), 8.12 (s, 1H), 7.58 (d, J = 2.2, 1H), 7.47 (dd, J = 8.6, 2.4, 1H), 7.27 (dd, J = 8.6, 5.6, 2H), 7.13-7.05 (m, 2H), 6.73 (d, J = 8.6, 1H), 3.03-2.97 (m, 2H), 2.89 (m, 2H), 2.81 (m, 2H), 2.41 (m, 2H), 2.04 (s, 3H) |

HPLC-MS; rt; [M + $H^+$]*
RT: 3.55 min;
Mass fould $[M]^+$: 377.3

-continued
| No. | Name/structure | $^1H$ NMR (500 MHz, DMSO-$d_6$) δ [ppm] J [Hz] |
|---|---|---|
| "A66" | 6-{4-[2-(4-Bromo-2-fluorophenyl)ethyl]-5-methylpyrimidin-2-ylamino}-3,4-dihydro-1H-quinolin-2-one 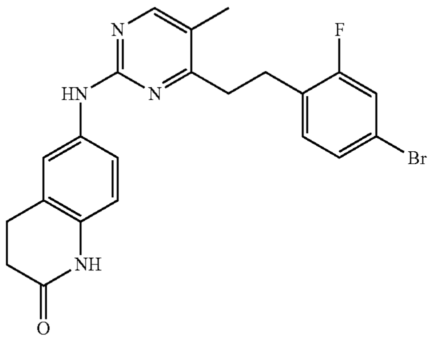 | |
| "A67" | 6-(5-Methyl-4-{2-[2-(propane-1-sulfonyl)phenyl]-ethyl}pyrimidin-2-ylamino}-3,4-dihydro-1H-quinolin-2-one 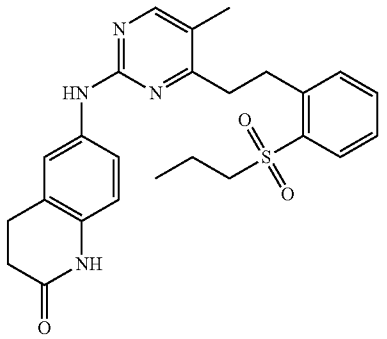 | |
| "A68" | 6-{4-[2-(4-Fluorophenyl)ethyl]-5-methyl-pyrimidin-2-ylamino}-3H-benzoxazol-2-one 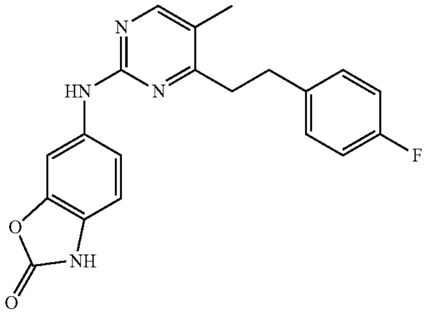 | |

-continued
| No. | Name/structure | $^1H$ NMR (500 MHz, DMSO-$d_6$) δ [ppm] J [Hz] |
|---|---|---|
| "A69" | 6-{4-[2-(4-Bromo-2-fluorophenyl)ethyl]-5-methylpyrimidin-2-ylamino}-3H-benzoxazol-2-one 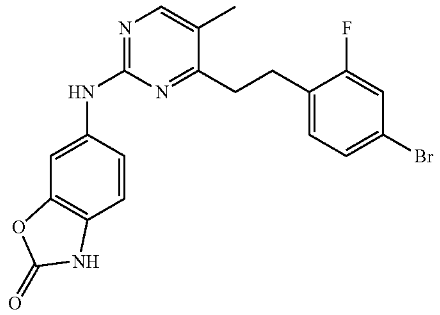 | |
| "A70" | 6-(5-Methyl-4-{2-[2-(propane-1-sulfonyl)phenyl]-ethyl]pyrimidin-2-ylamino}-3H-benzoxazol-2-one 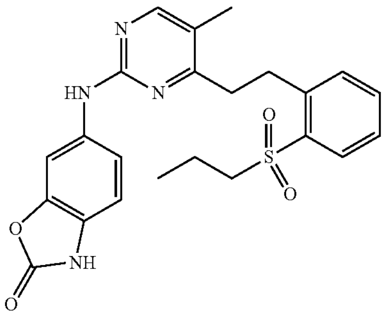 | |
| "A71" | [5-(1-Methyl-1H-pyrazol-4-yl)-4-phenethyl-pyrimidin-2-yl]phenylamine 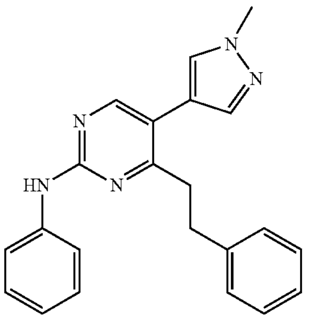 | 9.56 (s, 1H), 8.32 (d, J = 5.0, 1H), 8.01 (s, 1H), 7.78-7.71 (m, 3H), 7.45 (d, J = 8.7, 2H), 7.26 (dd, J = 10.5, 5.8, 4H), 7.17 (t, J = 6.8, 1H), 6.72 (d, J = 5.0, 1H), 3.84 (s, 3H), 3.06-3.00 (m, 2H), 2.96-2.89 (m, 2H) |
HPLC-MS; rt; [M + $H^+$]*
RT: 4.05 min;
Mass fould $[M]^+$: 356.3

-continued
| No. | Name/structure | $^1H$ NMR (500 MHz, DMSO-$d_6$) δ [ppm] J [Hz] |
|---|---|---|
| "A72" | (5-Furan-2-yl-4-phenethylpyrimidin-2-yl]-phenylamine 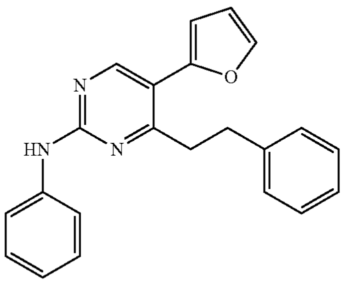 | |
| "A73" | [5-(2-Methylthiazol-4-yl)-4-phenethylpyrimidin-2-yl]phenylamine 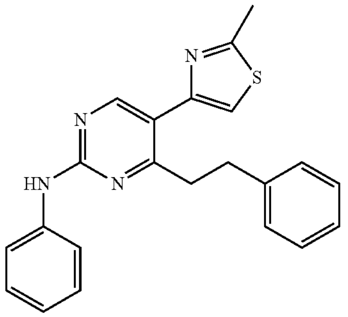 | |
| "A74" | 5-{4-[2-(4-Fluorophenyl)ethyl]-5-trifluoro-methylpyrimidin-2-ylamino}-1,3-dihydroindol-2-one 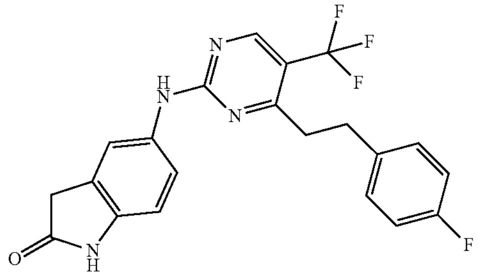 HPLC-MS; rt; [M + H$^+$]* RT: 4.99 min; Mass fould [M]$^+$: 417 | 10.31 (s, 1H), 10.07 (s, 1H), 8.61 (s, 1H), 7.58 (s, 1H), 7.48 (dd, J = 8.4, 2.1, 1H), 7.24 (dd, J = 8.2, 5.8, 2H), 7.10 (t, J = 8.8, 2H), 6.76 (d, J = 8.4, 1H), 3.48 (s, 2H), 3.13-2.93 (m, 4H) |
| "A75" | 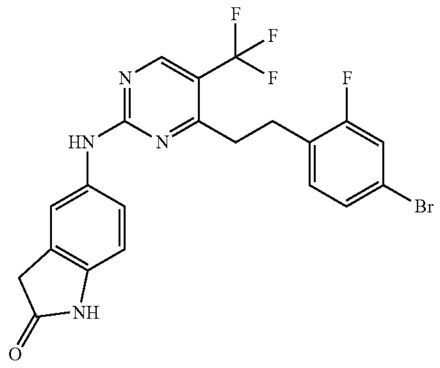 [SMILES: O=C1Cc2cc(Nc3ncc(C(F)(F)F)c(CCc4ccc(Br)cc4F)n3)ccc2N1] | |

-continued
| No. | Name/structure | $^1H$ NMR (500 MHz, DMSO-$d_6$) δ [ppm] J [Hz] |
|---|---|---|
| "A76" | 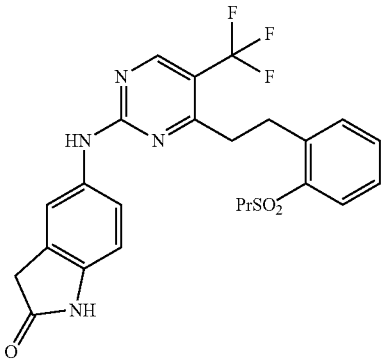 | |
| "A77" | 6-{4-[2-(4-Fluorophenyl)ethyl]-5-trifluoro-methylpyrimidin-2-ylamino}-3,4-dihydro-1H-quinolin-2-one 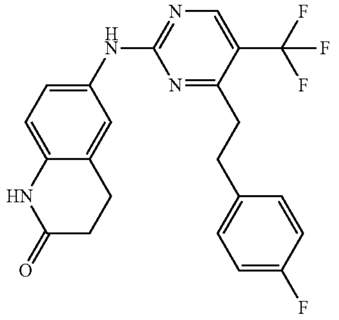 HPLC-MS; rt; [M + H+]* RT: 5.11 min; Mass fould [M]+: 431 | 10.08 (s, 1H), 10.02 (s, 1H), 8.62 (s, 1H), 7.55 (s, 1H), 7.45 (dd, J = 8.6, 2.2, 1H), 7.24 (dd, J = 8.4, 5.6, 2H), 7.09 (t, J = 8.9, 2H), 6.80 (d, J = 8.5, 1H), 3.12-2.96 (m, 4H), 2.84 (t, J = 7.5, 2H), 2.43 (dd, J = 8.4, 6.7, 2H) |
| "A78" | 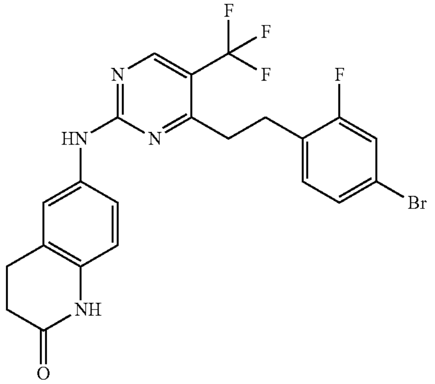 [SMILES: O=C1CCc2cc(Nc3ncc(C(F)(F)F)c(CCc4ccc(Br)cc4F)n3)ccc2N1] | |

-continued
| No. | Name/structure | $^1H$ NMR (500 MHz, DMSO-$d_6$) δ [ppm] J [Hz] |
|---|---|---|
| "A79" | 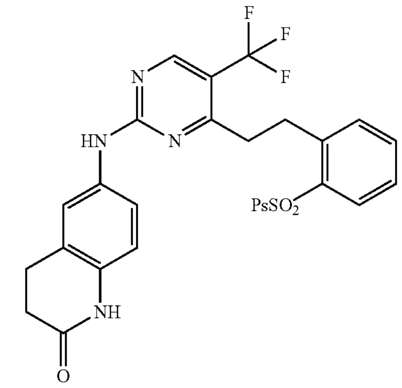 | |
| "A80" | 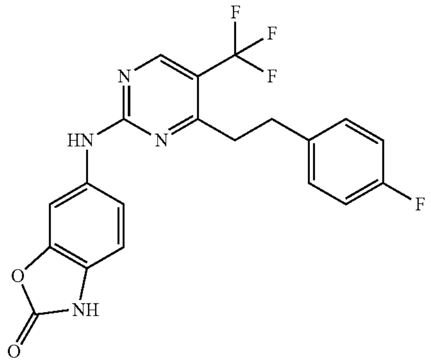 [SMILES: O=c1[nH]c2ccc(Nc3ncc(C(F)(F)F)c(CCc4ccc(F)cc4)n3)cc2o1] | |
| "A81" | 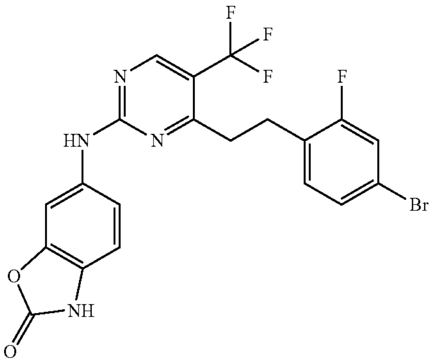 [SMILES: O=c1[nH]c2ccc(Nc3ncc(C(F)(F)F)c(CCc4ccc(Br)cc4F)n3)cc2o1] | |
| "A82" | 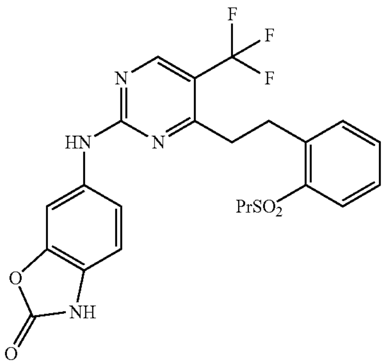 | |

-continued
| No. | Name/structure | $^1H$ NMR (500 MHz, DMSO-$d_6$) δ [ppm] J [Hz] |
|---|---|---|
| "A83" | 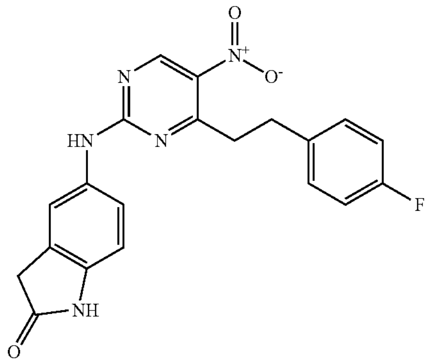 [SMILES: O=C1Cc2cc(Nc3ncc([N+](=O)[O-])c(CCc4ccc(F)cc4)n3)ccc2N1] | |
| "A84" | 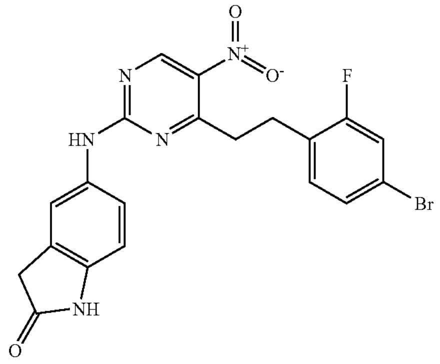 | |
| "A85" | 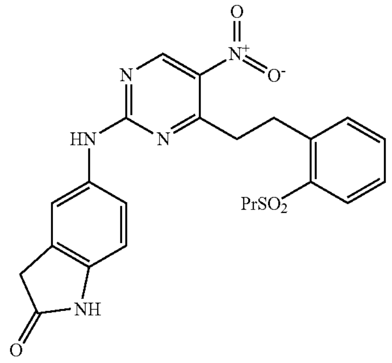 | |
| "A86" | 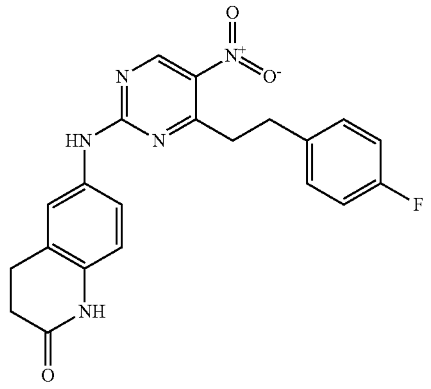 | |

-continued
| No. | Name/structure | $^1$H NMR (500 MHz, DMSO-$d_6$) δ [ppm] J [Hz] |
|---|---|---|
| "A87" | 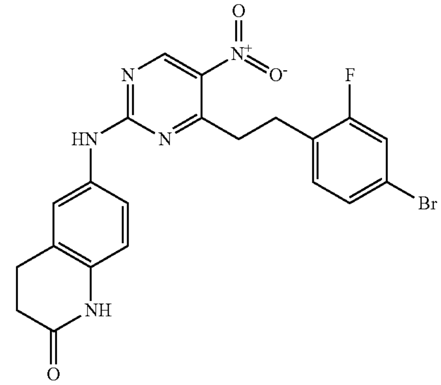 | |
| "A88" | 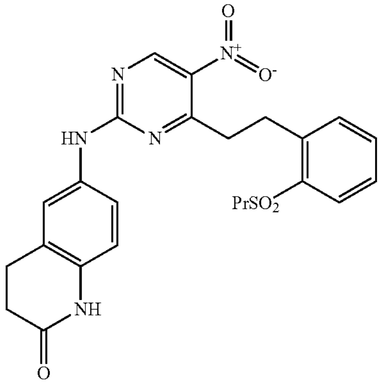 | |
| "A89" | 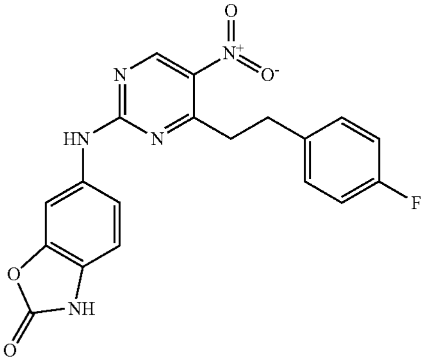 | |
| "A90" | 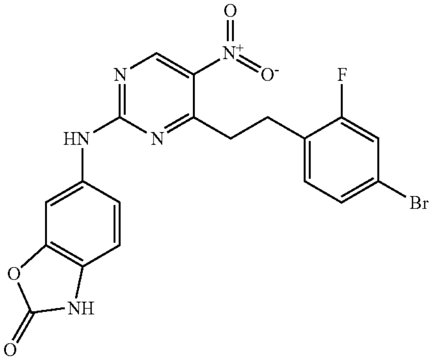 | |

-continued
| No. | Name/structure | $^1$H NMR (500 MHz, DMSO-$d_6$) δ [ppm] J [Hz] |
|---|---|---|
| "A91" | 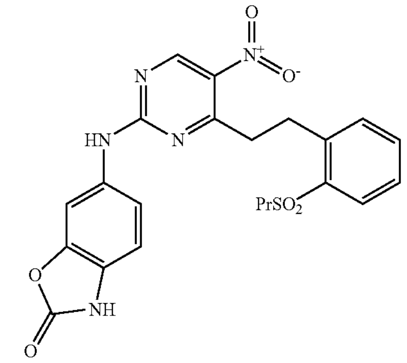 | |
| "A92" | 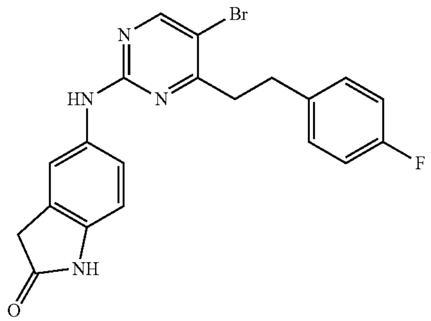 [SMILES: O=C1Cc2cc(Nc3ncc(Br)c(CCc4ccc(F)cc4)n3)ccc2N1] | |
| "A93" | 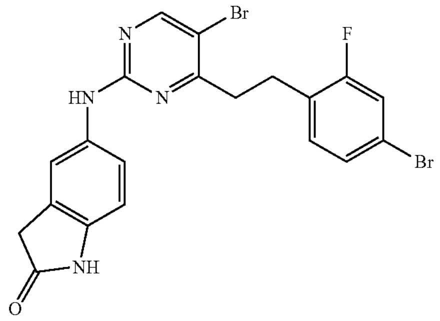 [SMILES: O=C1Cc2cc(Nc3ncc(Br)c(CCc4ccc(Br)cc4F)n3)ccc2N1] | |
| "A94" | 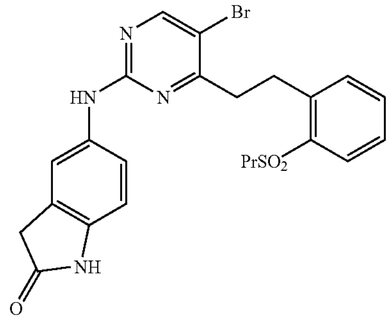 | |

-continued
| No. | Name/structure | $^1$H NMR (500 MHz, DMSO-$d_6$) δ [ppm] J [Hz] |
|---|---|---|
| "A95" | 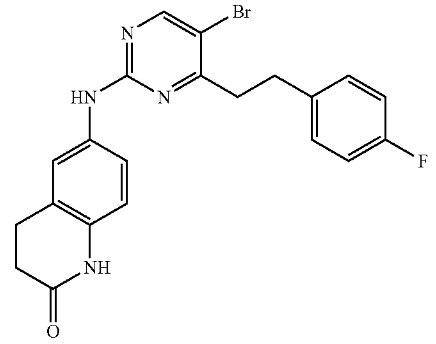 [SMILES: O=C1CCc2cc(Nc3ncc(Br)c(CCc4ccc(F)cc4)n3)ccc2N1] | |
| "A96" | 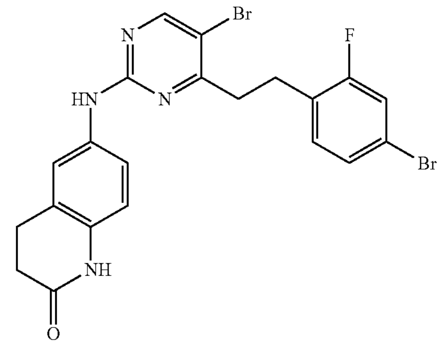 [SMILES: O=C1CCc2cc(Nc3ncc(Br)c(CCc4ccc(Br)cc4F)n3)ccc2N1] | |
| "A97" | 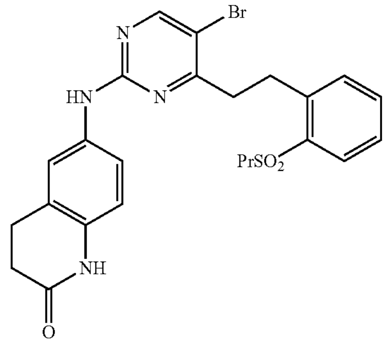 | |
| "A98" | 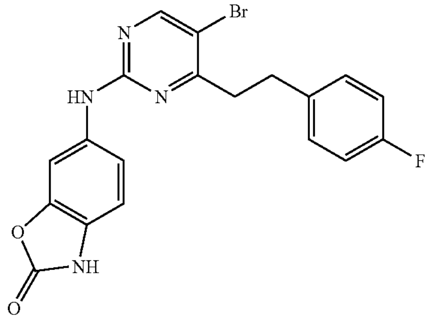 [SMILES: O=c1[nH]c2ccc(Nc3ncc(Br)c(CCc4ccc(F)cc4)n3)cc2o1] | |

-continued
| No. | Name/structure | $^1H$ NMR (500 MHz, DMSO-$d_6$) δ [ppm] J [Hz] |
|---|---|---|
| "A99" | 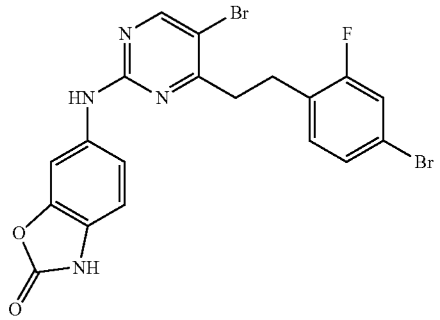 | |
| "A100" | 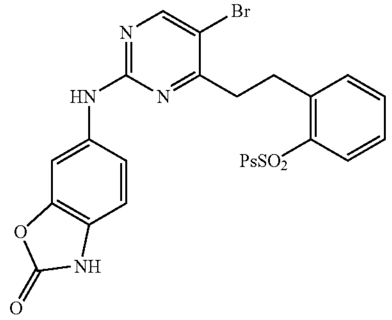 | |
| "A101" | 6-(5-Bromo-4-phenethylpyrimidin-2-ylamino)-3,4-dihydro-1H-quinolin-2-one 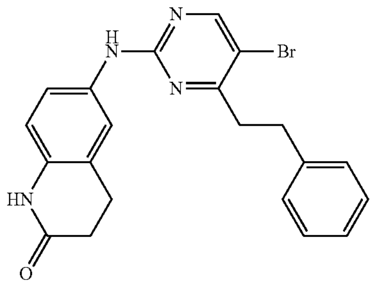 HPLC-MS; rt; [M + H$^+$]* RT: 4.88 min; Mass fould [M]$^+$: 423 | 9.96 (s, 1H), 9.63 (s, 1H), 8.45 (s, 1H), 7.51 (s, 1H), 7.41 (dd, J = 8.6, 2.4, 1H), 7.32-7.17 (m, 6H), 6.76 (d, J = 8.5, 1H), 3.02 (s, 4H), 2.85-2.79 (m, 2H), 2.44-2.39 (m, 2H) |
| "A102" | 5-(4-Phenethyl-5-trifluoromethylpyrimidin-2-ylamino)-1,3-dihydroindol-2-one 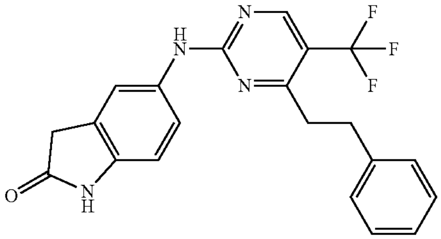 HPLC-MS; rt; [M + H$^+$]* RT: 4.94 min; Mass fould [M]$^+$: 399.3 | 10.31 (s, 1H), 10.07 (s, 1H), 8.61 (s, 1H), 7.58 (s, 1H), 7.48 (d, J = 8.6, 1H), 7.29 (t, J = 7.4, 2H), 7.20 (dd, J = 15.2, 7.1, 3H), 6.76 (d, J = 8.4, 1H), 3.48 (s, 2H), 3.03 (s, 4H) |

-continued

| No. | Name/structure | $^1$H NMR (500 MHz, DMSO-$d_6$) δ [ppm] J [Hz] |
|---|---|---|
| "A103" | 6-(4-Phenethyl-5-trifluoromethylpyrimidin-2-ylamino)-3,4-dihydro-1H-quinolin-2-one 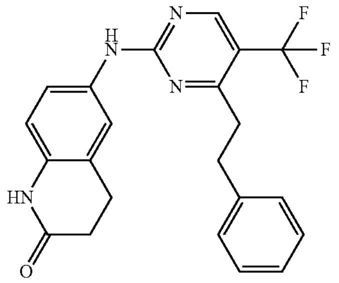 HPLC-MS; rt; [M + H$^+$]* RT: 5.17 min; Mass fould [M]$^+$: 413.3 | 10.09 (s, 1H), 10.02 (s, 1H), 8.62 (s, 1H), 7.56 (s, 1H), 7.45 (dd, J = 8.5, 2.4, 1H), 7.33-7.25 (m, 2H), 7.20 (dd, J = 16.2, 7.4, 3H), 6.80 (d, J = 8.6, 1H), 3.08-3.00 (m, 4H), 2.84 (t, J = 7.5, 2H), 2.45-2.40 (m, 3H) |
| "A104" | 6-(5-Methyl-4-{2-[3-(propane-1-sulfonyl)phenyl]-ethyl]pyrimidin-2-ylamino}-3,4-dihydro-1H-quinolin-2-one 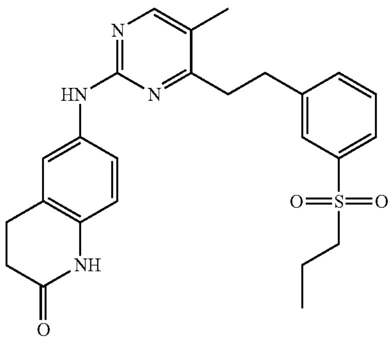 HPLC-MS; rt; [M + H$^+$]* RT: 3.33 min; Mass fould [M]$^+$: 465.2 | 9.91 (s, 1H), 9.21 (s, 1H), 8.12 (s, 1H), 7.68 (d, J = 7.3, 2H), 7.63 (d, J = 7.7, 1H), 7.60-7.52 (m, 2H), 7.45 (dd, J = 8.6, 2.3, 1H), 6.73 (d, J = 8.6, 1H), 3.22-3.11 (m, 4H), 2.97 (t, J = 7.6, 2H), 2.81 (t, J = 7.5, 2H), 2.44-2.38 (m, 2H), 2.03 (s, 3H), 1.45 (m, 2H), 0.85 (t, J = 7.4, 3H) |
| "A105" | 6-(5-Fluoro-4-{2-[3-(propane-1-sulfonyl)phenyl]-ethyl]pyrimidin-2-ylamino}-3,4-dihydro-1H-quinolin-2-one 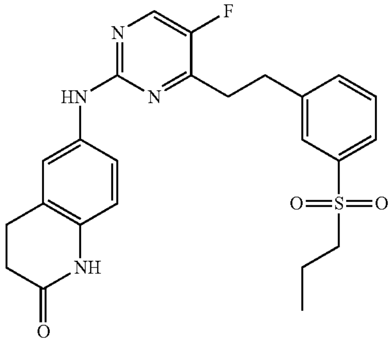 HPLC-MS; rt; [M + H$^+$]* RT: 4.10 min; Mass fould [M]$^+$: 469.3 | 8.14 (d, J = 1.5, 1H), 7.83 (s, 1H), 7.77-7.74 (m, 1H), 7.67 (s, 1H), 7.52-7.48 (m, 2H), 7.43 (s, 1H), 7.37 (dd, J = 8.4, 2.4, 1H), 7.06 (s, 1H), 6.72 (d, J = 8.4, 1H), 3.50 (s, 1H), 3.23-3.16 (m, 2H), 3.12-2.97 (m, 6H), 2.65 (dd, J = 8.4, 6.6, 2H), 1.78-1.66 (m, 2H), 0.99 (t, J = 7.4, 3H) |

-continued

| No. | Name/structure | $^1H$ NMR (500 MHz, DMSO-$d_6$) δ [ppm] J [Hz] |
|---|---|---|
| "A106" | [6-(4-tert-Butylphenoxy)pyridin-3-yl]-(5-fluoro-4-phenethylpyrimidin-2-yl)amine 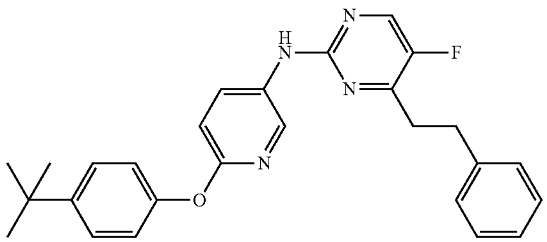 HPLC-MS; rt; [M + H$^+$]* RT: 6.68 min; Mass fould [M]$^+$: 443.2 | 9.73 (s, 1H), 8.44 (d, J = 2.6, 1H), 8.39 (d, J = 1.3, 1H), 8.11 (dd, J = 8.8, 2.7, 1H), 7.39 (d, J = 8.6, 2H), 7.30-7.13 (m, 5H), 6.97 (t, J = 8.4, 3H), 3.01 (s, 4H), 1.28 (s, 9H) |
| "A107" | (5-Fluoro-4-phenethylpyrimidin-2-yl)-(6-trifluoromethylpyridin-3-yl)amine 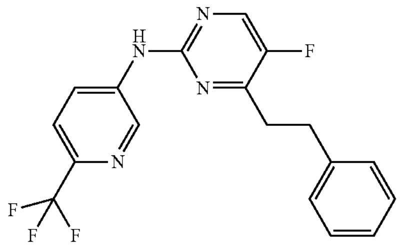 HPLC-MS; rt; [M + H$^+$]* RT: 5.65 min; Mass fould [M]$^+$: 363.3 | 10.35 (s, 1H), 9.00 (d, J = 2.5, 1H), 8.52 (d, J = 1.8, 1H), 8.40 (dd, J = 8.6, 2.3, 1H), 7.81 (d, J = 8.7, 1H), 7.30-7.21 (m, 4H), 7.20-7.15 (m, 1H), 3.04 (m, 4H) |
| "A108" | (5-Fluoro-4-phenethylpyrimidin-2-yl)-(6-fluoropyridin-3-yl)amine 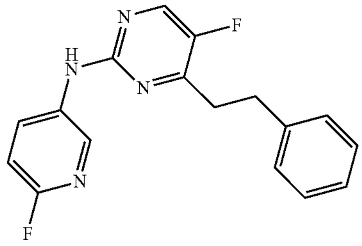 HPLC-MS; rt; [M + H$^+$]* RT: 5.05 min; Mass fould [M]$^+$: 313.3 | 9.90 (s, 1H), 8.54-8.48 (m, 1H), 8.43 (d, J = 1.8, 1H), 8.21 (ddd, J = 8.9, 7.4, 2.9, 1H), 7.27 (dd, J = 10.0, 4.6, 2H), 7.24-7.14 (m, 3H), 7.11 (dd, J = 8.9, 3.3, 1H), 3.03 (s, 4H) |

-continued

| No. | Name/structure | $^1$H NMR (500 MHz, DMSO-$d_6$) δ [ppm] J [Hz] |
|---|---|---|
| "A109" | 5-(5-Fluoro-4-phenethylpyrimidin-2-ylamino)-pyridine-2-carbonitrile 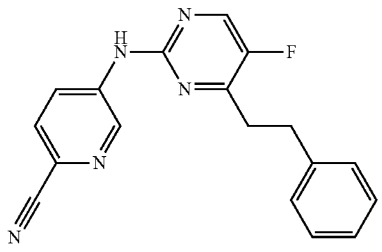 HPLC-MS; rt; [M + H$^+$]* RT: 5.01 min; Mass fould [M]$^+$: 320.3 | 10.50 (s, 1H), 8.96 (d, J = 2.4, 1H), 8.55 (d, J = 1.7, 1H), 8.37 (dd, J = 8.7, 2.6, 1H), 7.92 (d, J = 8.6, 1H), 7.22 (m, 5H), 3.06 (s, 4H) |
| "A110" | N-[5-(5-Fluoro-4-phenethylpyrimidin-2-ylamino)-pyridin-2-yl]acetamide 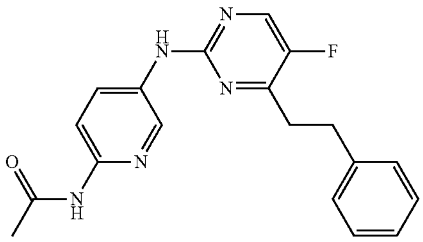 HPLC-MS; rt; [M + H$^+$]* RT: 3.75 min; Mass fould [M]$^+$: 352.3 | 10.33 (s, 1H), 9.73 (s, 1H), 8.61-8.57 (m, 1H), 8.40 (d, J = 1.8, 1H), 8.04 (dd, J = 9.0, 2.7, 1H), 7.97 (d, J = 8.9, 1H), 7.31-7.14 (m, 5H), 3.02 (s, 4H), 2.07 (s, 3H) |
| "A111" | N-Methyl-N-(2-{2-[2-(2-oxo-2,3-dihydro-1H-indol-5-ylamino)-5-trifluoromethylpyrimidin-4-yl]ethyl}phenyl)methanesulfonamide 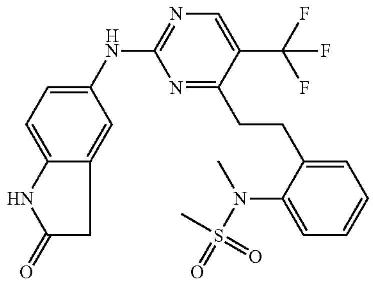 | |

Pharmacological Test Results

TABLE 1

FAK inhibition of some compounds of the formula I according to the invention

| No. | $IC_{50}$ (enzymatic) | $IC_{50}$ (cellular) |
|---|---|---|
| "A1" | C | |
| "A2" | A | C |
| "A3" | C | |
| "A5" | A | |
| "A6" | B | |
| "A7" | B | |

TABLE 1-continued

FAK inhibition of some compounds of the formula I according to the invention

| No. | $IC_{50}$ (enzymatic) | $IC_{50}$ (cellular) |
|---|---|---|
| "A9" | B | |
| "A11" | B | |
| "A13" | B | |
| "A16" | C | |
| "A20" | B | |
| "A21" | B | |
| "A22" | C | |
| "A24" | | C |

TABLE 1-continued

| FAK inhibition of some compounds of the formula I according to the invention | | |
|---|---|---|
| No. | $IC_{50}$ (enzymatic) | $IC_{50}$ (cellular) |
| "A25" | B | C |
| "A26" | | |
| "A27" | B | |
| "A28" | B | |
| "A29" | C | |
| "A30" | B | |
| "A31" | A | C |
| "A32" | B | |
| "A33" | B | |
| "A34" | A | B |
| "A35" | B | |
| "A36" | B | |
| "A37" | | B |
| "A38" | B | |
| "A39" | B | |
| "A40" | B | |
| "A41" | B | |
| "A43" | B | |
| "A44" | A | |
| "A45" | A | |
| "A46" | B | |
| "A101" | B | |
| "A102" | B | |
| "A103" | B | |

$IC_{50}$: <0.3 μM = A 0.3-3 μM = B >3-50 μM = C

The following examples relate to pharmaceutical preparations:

Example A

Injection Vials

A solution of 100 g of an active compound of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active compound.

Example B

Suppositories

A mixture of 20 g of an active compound of the formula I with 100 g of soya lecithin and 1400 g of cocoa butter is melted, poured into moulds and allowed to cool. Each suppository contains 20 mg of active compound.

Example C

Solution

A solution is prepared from 1 g of an active compound of the formula I, 9.38 g of $NaH_2PO_4 \cdot 2\ H_2O$, 28.48 g of $Na_2HPO_4 \cdot 12\ H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

Example D

Ointment 500 mg of an active compound of the formula I are mixed with 99.5 g of Vaseline under aseptic conditions.

Example E

Tablets

A mixture of 1 kg of active compound of the formula I, 4 kg of lactose, 1.2 kg of potato starch, 0.2 kg of talc and 0.1 kg of magnesium stearate is pressed in a conventional manner to give tablets in such a way that each tablet contains 10 mg of active compound.

Example F

Dragees

Tablets are pressed analogously to Example E and subsequently coated in a conventional manner with a coating of sucrose, potato starch, talc, tragacanth and dye.

Example G

Capsules 2 kg of active compound of the formula I are introduced into hard gelatine capsules in a conventional manner in such a way that each capsule contains 20 mg of the active compound.

Example H

Ampoules

A solution of 1 kg of active compound of the formula I in 60 l of bidistilled water is sterile filtered, transferred into ampoules, lyophilised under sterile conditions and sealed under sterile conditions. Each ampoule contains 10 mg of active compound.

The invention claimed is:

1. A compound selected from the the following compounds:

| No. | Name and/or structure |
|---|---|
| "A1" | N-(2-{2-[2-(4-Methanesulfonylphenylamino)pyrimidin-4-yl]-ethyl}phenyl)-N-methylmethanesulfonamide |
| "A2" | N-Methyl-N-(2-{2-[2-(2-oxo-1,2,3,4-tetrahydroquinolin-6-ylamino)pyrimidin-4-yl]ethyl}phenyl)methanesulfonamide |
| "A3" | 6-{4-[2-(3-Methanesulfonylphenyl)ethyl]pyrimidin-2-ylamino}-3,4-dihydro-1H-quinolin-2-one |
| "A4" | (4-Methanesulfonylphenyl)-{4-[2-(3-methanesulfonylphenyl)-ethyl]pyrimidin-2-yl}amine |
| "A5" | N-Methyl-N-(2-{2-[2-(2-oxo-2,3-dihydro-1H-indol-5-ylamino)-pyrimidin-4-yl]ethyl}phenyl)methanesulfonamide |
| "A6" | N-Methyl-N-(3-{2-[2-(2-oxo-2,3-dihydro-1H-indol-5-ylamino)-pyrimidin-4-yl]ethyl}pyridin-2-yl)methanesulfonamide |
| "A7" | N-Methyl-N-(3-{2-[2-(2-oxo-1,2,3,4-tetrahydroquinolin-6-ylamino)pyrimidin-4-yl]ethyl}pyridin-2-yl)methanesulfonamide |
| "A8" | N-(3-{2-[2-(4-Methanesulfonylphenylamino)pyrimidin-4-yl]-ethyl}pyridin-2-yl)-N-methylmethanesulfonamide |
| "A9" | (2-{2-[2-(2-Oxo-2,3-dihydro-1H-indol-5-ylamino)pyrimidin-4-yl]ethyl}phenyl)acetonitrile |
| "A10" | N-Methyl-N-(3-{2-[2-(2-oxo-2,3-dihydro-1H-indol-5-ylamino)-pyrimidin-4-yl]ethyl}pyridin-2-yl)acetamide |
| "A11" | (4-Fluoro-2-{2-[2-(2-oxo-2,3-dihydro-1H-indol-5-ylamino)-pyrimidin-4-yl]ethyl}phenyl)acetonitrile |
| "A12" | N-Methyl-N-(3-{2-[2-(2-oxo-2,3-dihydro-1H-indol-5-ylamino)-pyrimidin-4-yl]ethyl}pyridin-2-yl)formamide |
| "A13" | 1-(2-{2-[2-(2-Oxo-2,3-dihydro-1H-indol-5-ylamino)pyrimidin-4-yl]ethyl}phenyl)cyclobutanecarbonitrile |
| "A14" | N-[2-(3-{2-[2-(2-Oxo-2,3-dihydro-1H-indol-5-ylamino)-pyrimidin-4-yl]ethyl}pyridin-2-ylamino)ethyl] formamide |

-continued

| No. | Name and/or structure |
|---|---|
| "A15" | (2-{2-[2-(2-Oxo-2,3-dihydro-1H-indol-5-ylamino)pyrimidin-4-yl]ethyl}-5-trifluoromethylphenyl)acetonitrile |
| "A16" | 3-(3-{2-[2-(2-Oxo-2,3-dihydro-1H-indol-5-ylamino)pyrimidin-4-yl]ethyl}pyridin-2-yl)azetidine-3-carbonitrile |
| "A17" | (2-{2-[2-(2-Oxo-2,3-dihydro-1H-indol-5-ylamino)pyrimidin-4-yl]ethyl}-4-trifluoromethylphenyl)acetonitrile |
| "A18" | (5-Fluoro-2-{2-[2-(2-oxo-2,3-dihydro-1H-indol-5-ylamino)-pyrimidin-4-yl]ethyl}phenyl)acetonitrile |
| "A19" | 1-(2-{2-[2-(2-Oxo-2,3-dihydro-1H-indol-5-ylamino)pyrimidin-4-yl]ethyl}-4-trifluoromethylphenyl)cyclobutanecarbonitrile |
| "A20" | N-Methyl-N-(3-{2-[2-(2-oxo-2,3-dihydrobenzoxazol-6-ylamino)pyrimidin-4-yl]ethyl}pyridin-2-yl)methanesulfonamide |
| "A21" | N-Methyl-N-(3-{2-[2-(1-methyl-2-oxo-2,3-dihydro-1H-indol-5-ylamino)pyrimidin-4-yl]ethyl}pyridin-2-yl)methanesulfonamide |
| "A22" | N-(3-{2-[2-(3-Cyanophenylamino)pyrimidin-4-yl]ethyl}-pyridin-2-yl)-N-methylmethanesulfonamide |
| "A23" | N-(3-{2-[2-(3-Cyano-4-fluorophenylamino)pyrimidin-4-yl]-ethyl}pyridin-2-yl)-N-methylmethanesulfonamide |
| "A24" | N-Methyl-N-[3-(2-{2-[(6-oxo-1,6-dihydropyridazin-3-ylmethyl)amino]pyrimidin-4-yl}ethyl)pyridin-2-yl]-methanesulfonamide |
| "A25" | N-(3-{2-[2-(1,3-Dimethyl-2-oxo-2,3-dihydro-1H-benzimidazol-5-ylamino)pyrimidin-4-yl]ethyl}pyridin-2-yl)-N-methylmethanesulfonamide |
| "A26" | N-(3-{[5-Cyano-2-(2-oxo-2,3-dihydrobenzoxazol-6-ylamino)-pyrimidin-4-ylamino]methyl}pyridin-2-yl)-N-methylmethanesulfonamide |
| "A27" | N-Methyl-N-(2-{2-[2-(2-oxo-2,3-dihydrobenzoxazol-6-ylamino)pyrimidin-4-yl]ethyl}phenyl)methanesulfonamide |
| "A28" | N-(2-{2-[2-(3-Cyanophenylamino)pyrimidin-4-yl]ethyl}-phenyl)-N-methylmethanesulfonamide |
| "A29" | N-(2-{2-[2-(3-Cyano-4-fluorophenylamino)pyrimidin-4-yl]-ethyl}phenyl)-N-methylmethanesulfonamide |
| "A30" | N-Methyl-N-(2-{2-[2-(2-oxo-2,3-dihydrobenzothiazol-5-ylamino)pyrimidin-4-yl]ethyl}phenyl)methanesulfonamide |
| "A31" | N-(2-{2-[2-(1-Acetyl-2,3-dihydro-1H-indol-5-ylamino)-pyrimidin-4-yl]ethyl}phenyl)-N-methylmethanesulfonamide |
| "A32" | 2-[3-(4-{2-[2-(Methanesulfonylmethylamino)phenyl]ethyl}-pyrimidin-2-ylamino)phenyl]-N-methylacetamide |
| "A33" | N-Methyl-N-[2-(2-{2-[4-(3-oxomorpholin-4-yl)phenylamino]-pyrimidin-4-yl}ethyl)phenyl]methanesulfonamide |
| "A34" | N-[4-(4-{2-[2-(Methanesulfonylmethylamino)phenyl]ethyl}-pyrimidin-2-ylamino)phenyl]nicotinamide |
| "A35" | N-Methyl-N-[2-(2-{2-[4-(2-oxopyrrolidin-1-yl)phenylamino]-pyrimidin-4-yl}ethyl)phenyl]methanesulfonamide |
| "A36" | N-[2-(2-{2-[3,5-Dichloro-4-(2-oxopyrrolidin-1-yl)phenyl-amino]pyrimidin-4-yl}ethyl)phenyl]-N-methylmethane-sulfonamide |
| "A37" | N-[2-(2-{2-[3-Cyano-4-(2-oxopiperidin-1-yl)phenylamino]-pyrimidin-4-yl}ethyl)phenyl]-N-methylmethanesulfonamide |
| "A38" | N-[2-(2-{2-[4-(1,3-Dioxo-1,3-dihydroisoindol-2-yl)phenyl-amino]pyrimidin-4-yl}ethyl)phenyl]-N-methylmethane-sulfonamide |
| "A39" | N-Methyl-N-[3-(2-{2-[4-(2-oxopyrrolidin-1-yl)phenylamino]-pyrimidin-4-yl}ethyl)pyridin-2-yl]methanesulfonamide |
| "A40" | N-[4-(4-{2-[2-(Methanesulfonylmethylamino)pyridin-3-yl]-ethyl}pyrimidin-2-ylamino)phenyl]nicotinamide |
| "A41" | N-Methyl-N-[3-(2-{2-[4-(3-oxomorpholin-4-yl)phenylamino]-pyrimidin-4-yl}ethyl)pyridin-2-yl]methanesulfonamide |
| "A42" | N-[3-(2-{2-[3-Cyano-4-(2-oxopiperidin-1-yl)phenylamino]-pyrimidin-4-yl}ethyl)pyridin-2-yl]-N-methylmethane-sulfonamide |
| "A43" | N-[3-(2-{2-[4-(1,3-Dioxo-1,3-dihydroisoindol-2-yl)-phenylamino]pyrimidin-4-yl}ethyl)pyridin-2-yl]-N-methyl-methanesulfonamide |
| "A44" | N-Methyl-N-(5-methyl-3-{2-[2-(2-oxo-2,3-dihydro-1H-indol-5-ylamino)pyrimidin-4-yl]ethyl}pyridin-2-yl)methanesulfonamide |
| "A45" | 1-(4-Fluoro-2-{2-[2-(2-oxo-2,3-dihydro-1H-indol-5-ylamino)-pyrimidin-4-yl]ethyl}phenyl)cyclobutanecarbonitrile |
| "A46" | 1-(5-Fluoro-2-{2-[2-(2-oxo-2,3-dihydro-1H-indol-5-ylamino)-pyrimidin-4-yl]ethyl}phenyl)cyclobutanecarbonitrile |
| "A47" | 1-(2-{2-[2-(2-Oxo-2,3-dihydro-1H-indol-5-ylamino)pyrimidin-4-yl]ethyl}-5-trifluoromethylphenyl)cyclobutanecarbonitrile |
| "A48" | (5-Fluoro-4-phenethylpyrimidin-2-yl)phenylamine |
| "A49" | (5-Methyl-4-phenethylpyrimidin-2-yl)phenylamine |
| "A50" | (4-Phenethyl-5-trifluoromethylpyrimidin-2-yl)phenylamine |
| "A52" | (5-Bromo-4-phenethylpyrimidin-2-yl)phenylamine |
| "A56" | 6-{5-Fluoro-4-[2-(4-fluorophenyl)ethyl]pyrimidin-2-ylamino}-3,4-dihydro-1H-quinolin-2-one |
| "A65" | 6-{4-[2-(4-Fluorophenyl)ethyl]-5-methylpyrimidin-2-ylamino}-3,4-dihydro-1H-quinolin-2-one |
| "A71" | [5-(1-Methyl-1H-pyrazol-4-yl)-4-phenethylpyrimidin-2-yl]-phenylamine |
| "A74" | 5-{4-[2-(4-Fluorophenyl)ethyl]-5-trifluoromethylpyrimidin-2-ylamino}-1,3-dihydroindol-2-one |
| "A77" | 6-{4-[2-(4-Fluorophenyl)ethyl]-5-trifluoromethylpyrimidin-2-ylamino}-3,4-dihydro-1H-quinolin-2-one |
| "A101" | 6-(5-Bromo-4-phenethylpyrimidin-2-ylamino)-3,4-dihydro-1H-quinolin-2-one |
| "A102" | 5-(4-Phenethyl-5-trifluoromethylpyrimidin-2-ylamino)-1,3-dihydroindol-2-one |
| "A103" | 6-(4-Phenethyl-5-trifluoromethylpyrimidin-2-ylamino)-3,4-dihydro-1H-quinolin-2-one |
| "A104" | 6-(5-Methyl-4-{2-[3-(propane-1-sulfonyl)phenyl]ethyl}-pyrimidin-2-ylamino)-3,4-dihydro-1H-quinolin-2-one |
| "A105" | 6-(5-Fluoro-4-{2-[3-(propane-1-sulfonyl)phenyl]ethyl}-pyrimidin-2-ylamino)-3,4-dihydro-1H-quinolin-2-one |
| "A106" | [6-(4-tert-Butylphenoxy)pyridin-3-yl]-(5-fluoro-4-phenethylpyrimidin-2-yl)amine |
| "A107" | (5-Fluoro-4-phenethylpyrimidin-2-yl)-(6-trifluoromethylpyridin-3-yl)amine |
| "A108" | (5-Fluoro-4-phenethylpyrimidin-2-yl)-(6-fluoropyridin-3-yl)-amine |
| "A109" | 5-(5-Fluoro-4-phenethylpyrimidin-2-ylamino)pyridine-2-carbonitrile |
| "A110" | N-[5-(5-Fluoro-4-phenethylpyrimidin-2-ylamino)pyridin-2-yl]-acetamide |
| "A111" | N-Methyl-N-(2-{2-[2-(2-oxo-2,3-dihydro-1H-indol-5-ylamino)-5-trifluoromethylpyrimidin-4-yl]ethyl}phenyl)-methanesulfonamide |

or a pharmaceutically usable salt, tautomer or stereoisomer thereof, including mixtures thereof in all ratios.

2. A medicament composition comprising at least one compound according to claim 1 or a pharmaceutically usable salt, tautomer or stereoisomer thereof, including mixtures thereof in all ratios, and optionally excipients and/or adjuvants.

3. A method for the treatment of colon cancer which comprises administering to a patient in need thereof at least one compound according to claim 1 or a pharmaceutically usable salt, tautomer or stereoisomer thereof, including mixtures thereof in all ratios.

* * * * *